(12) United States Patent
Li et al.

(10) Patent No.: US 9,632,088 B2
(45) Date of Patent: Apr. 25, 2017

(54) METHODS AND COMPOSITIONS FOR GAMMA-SECRETASE ASSAY

(75) Inventors: Yue-Ming Li, New York, NY (US); De-Ming Chau, Petaling Jaya (MY); Jennifer C. Villa, Philadelphia, PA (US); Christina Crump, Miami, FL (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 25 days.

(21) Appl. No.: 13/821,090

(22) PCT Filed: Sep. 7, 2011

(86) PCT No.: PCT/US2011/050688
§ 371 (c)(1),
(2), (4) Date: Oct. 10, 2013

(87) PCT Pub. No.: WO2012/033831
PCT Pub. Date: Mar. 15, 2012

(65) Prior Publication Data
US 2014/0031247 A1    Jan. 30, 2014

Related U.S. Application Data

(60) Provisional application No. 61/380,587, filed on Sep. 7, 2010.

(51) Int. Cl.
*G01N 33/573* (2006.01)
*C07K 16/28* (2006.01)
(Continued)

(52) U.S. Cl.
CPC ......... *G01N 33/573* (2013.01); *C07K 14/705* (2013.01); *C07K 16/28* (2013.01);
(Continued)

(58) Field of Classification Search
CPC ........ C12Q 1/37; C07K 14/705; C07K 16/28; G01N 33/573; G01N 2500/02; G01N 2500/10
See application file for complete search history.

(56) References Cited

U.S. PATENT DOCUMENTS 4,816,567 A    3/1989  Cabilly et al.
4,873,316 A    10/1989  Meade et al.
(Continued)

FOREIGN PATENT DOCUMENTS

CN    1878865 A    12/2006
EP    0264166 A1    4/1988
(Continued)

OTHER PUBLICATIONS

Placanica et al.( PLoS One 4.4 (2009): e5088; 9 pages).*
(Continued)

*Primary Examiner* — Shafiqul Haq
(74) *Attorney, Agent, or Firm* — Mueting, Raasch & Gebhardt, P.A.

(57) ABSTRACT

Presented herein are polypeptide substrates based on Notch polypeptides, assay methods based on the use of these substrates, and screening methods directed toward identifying inhibitors of γ-secretase activity. The assay methods and the screening methods are adapted for use in high throughput multi-well plate assay apparatuses. In many embodiments the substrate polypeptides are labeled for ease of detection, and/or may bind specific ligands that themselves are labeled. Generally the labels promote high specificity as well as high sensitivity of detection. These features render the assay and screening methods that employ the labeled substrates especially suited for use in high throughput assay formats.

18 Claims, 14 Drawing Sheets

(51) Int. Cl.
  *C12Q 1/37* (2006.01)
  *C07K 14/705* (2006.01)
(52) U.S. Cl.
  CPC ........... *C12Q 1/37* (2013.01); *G01N 2500/02* (2013.01); *G01N 2500/10* (2013.01)

(56) References Cited

U.S. PATENT DOCUMENTS

| | | | |
|---|---|---|---|
| 4,946,778 | A | 8/1990 | Ladner et al. |
| 5,723,584 | A | 3/1998 | Schatz |
| 5,874,239 | A | 2/1999 | Schatz |
| 5,932,433 | A | 8/1999 | Schatz |
| 6,625,546 | B2 | 9/2003 | Sepetov et al. |
| 6,800,444 | B1 | 10/2004 | Cook et al. |
| 6,936,477 | B2 | 8/2005 | Still et al. |
| 7,083,812 | B2 | 8/2006 | Choi et al. |
| 7,378,511 | B2 | 5/2008 | Gurney et al. |
| 7,498,324 | B2 | 3/2009 | Han et al. |
| 2002/0098173 | A1 | 7/2002 | Findeis et al. |
| 2002/0115717 | A1 | 8/2002 | Gervais et al. |
| 2004/0121411 | A1 | 6/2004 | Roberts et al. |
| 2004/0132114 | A1 | 7/2004 | Beher |
| 2005/0169925 | A1 | 8/2005 | Bardroff et al. |
| 2006/0036077 | A1 | 2/2006 | Li et al. |
| 2006/0194265 | A1* | 8/2006 | Morris et al. ............... 435/7.23 |
| 2006/0275856 | A1* | 12/2006 | Okochi .................. C12Q 1/37 435/23 |
| 2007/0260058 | A1 | 11/2007 | Cheng et al. |
| 2007/0287666 | A1 | 12/2007 | Fraser et al. |
| 2008/0021056 | A1 | 1/2008 | Konradi et al. |
| 2008/0076752 | A1 | 3/2008 | Becker et al. |
| 2008/0085894 | A1 | 4/2008 | Parker et al. |
| 2008/0274476 | A1* | 11/2008 | Beher et al. ................ 435/7.4 |
| 2008/0317764 | A1 | 12/2008 | Huber et al. |
| 2008/0317834 | A1 | 12/2008 | Green et al. |
| 2009/0005256 | A1 | 1/2009 | Bittker et al. |
| 2009/0163594 | A1* | 6/2009 | Shapiro et al. ............... 514/601 |
| 2009/0209041 | A1 | 8/2009 | Gazit |
| 2010/0285988 | A1 | 11/2010 | Shelton et al. |
| 2011/0098227 | A1* | 4/2011 | Sharma ................ C07K 14/245 514/17.8 |
| 2011/0257027 | A2 | 10/2011 | Shelton et al. |

FOREIGN PATENT DOCUMENTS

| | | |
|---|---|---|
| WO | 01/83811 A1 | 11/2001 |
| WO | 03/008635 A2 | 1/2003 |
| WO | 2006/102542 A2 | 9/2006 |
| WO | 2006/102542 A3 | 4/2009 |

OTHER PUBLICATIONS

Adams et al., "The c-myc oncogene driven by immunoglobulin enhancers induces lymphoid malignancy in transgenic mice," Dec. 12, 1985, *Nature*, 318:533-538.
Alexander et al., "Expression of the c-myc oncogene under control of an immunoglobulin enhancer in E mu-myc transgenic mice," Apr. 1987 *Mol. Cell. Biol.* 7:1436-1444.
Altschul et al, "Basic local alignment search tool," J. Molec. Biol., 1990; 215: 403-410.
Amann et al., "Tightly regulated *tac* promoter vectors useful for the expression of unfused and fused proteins in *Escherichia coli*," *Gene*, Sep. 1988; 69:301-315.
Amtul et al., "A Presenilin 1 Mutation Associated with Familial Frontotemporal Dementia Inhibits γ-Secretase Cleavage of APP and Notch," *Neurobiology of Disease*, 2002; 9(2):269-273.
Antczak et al., "High-throughput identification of inhibitors of human mitochondrial peptide deformylase," Jun. 2007 *J. Biomol. Scrn.* 12(4):521-535. Available online on Apr. 13, 2007.
Antczak et al., "Development and validation of a high-density fluorescence polarization-based assay for the trypanosoma RNA triphosphatase TbCet1," Mar. 2009 *Comb. Chem. High Throughput Scrn.* 12:258-268.

Artavanis-Tsakonas et al., "Notch Signaling: Cell Fate Control and Signal Integration in Development," *Science*, 1999; 284 (5415): 770-776.
Ausubel et al. (eds.), *Current Protocols in Molecular Biology*. John Wiley & Sons: city, state; copyright 2002. Cover page, publisher's page, and table of contents; 14 pages.
Baldari et al. "A novel leader peptide which allows efficient secretion of a fragment of human interleukin 1 beta in Saccharomyces cerevisiae," *EMBO J.*, Jan. 1987; 6:229-234.
Banerji et al., "A lymphocyte-specific cellular enhancer is located downstream of the joining region in immunoglobulin heavy chain genes," *Cell*, Jul. 1983; 33:729-740.
Beel et al., "Substrate Specificity of γ-Secretase and Other Intramembrane Proteases," *Cell Mol Life Sci*, May 2008; 65(9): 1311-1334.
Beher et al., "Pharmacological knock-down of the presenilin 1 heterodimer by a novel gamma-secretase inhibitor: implications for presenilin biology," Nov. 30, 2001 *J. Biol. Chem.* 276(48):45394-45402. Available online on Sep. 26, 2001.
Benda et al., "Differentiated rat glial cell strain in tissue culture," Jul. 26, 1968 *Science* 161:370-371.
Benoist et al., "In vivo sequence requirements of the SV40 early promotor region," Mar. 26, 1981 *Nature* 290:304-310.
Bentahir et al., "Presenilin clinical mutations can affect γ-secretase activity by different mechanisms," *Journal of Neurochemistry*, 2006; 96: 732-742.
Berezovska et al., "The Alzheimer-related gene presenilin 1 facilitates notch 1 in primary mammalian neurons," *Molecular Brain Research*, 1999; 69(2):273-280.
Bitter et al., "[33] Expression and secretion vectors for yeast," in *Methods in Enzymology vol. 153 Recombinant DNA Part D*. Academic Press, Inc.: Burlington, MA; Copyright 1987. Title page and pp. 516-544.
Blackburn et al., "Electrochemiluminescence Detection for Development of Immunoassays and DNA Probe Assays for Clinical Diagnostics," 1991 *Clin. Chem.* 37(9):1534-1539.
Bolin et al., "Survey of cell lines in the American Type Culture Collection for bovine viral diarrhea virus," Jul. 1994 *J. Virol. Meth.* 48:211-221.
Borchelt et al., "Familial Alzheimer's Disease—Linked Presenilin 1 Variants Elevate Aβ1-42/1-40 Ratio In Vitro and In Vivo," *Neuron*, 1996; 17:1005-1013.
Brinster et al., "Regulation of metallothionein—thymidine kinase fusion plasmids injected into mouse eggs," Mar. 4, 1982 *Nature* 296:39-42.
Brou et al., "A Novel Proteolytic Cleavage Involved in Notch Signaling," *Mol. Cell*, 2000; 5(2):207-216.
Brown et al., "Regulated intramembrane proteolysis: a control mechanism conserved from bacteria to humans," Feb. 18, 2000 *Cell* 100:391-398.
Brodeur et al., *Monoclonal antibody Production Techniques and Applications*, Marcel Dekker, Inc., New York, NY, 1987: 51-63.
Buonassisi et al., "Hormone-producing cultures of adrenal and pituitary tumor origin," Jul. 15, 1962 *Proc. Natl. Acad. Sci. USA* 48:1184-1190.
Buxbaum et al., "Evidence that tumor necrosis factor alpha converting enzyme is involved in regulated alpha-secretase cleavage of the Alzheimer amyloid protein precursor," Oct. 23, 1998 *J. Biol. Chem.* 273(43):27765-27767.
Byrne et al., "Multiplex gene regulation: A two-tiered approach to transgene regulation in transgenic mice," *PNAS USA*, Jul. 1989; 86:5473-5477.
Calame et al., "Transcriptional Controlling Elements in the Immunoglobulin and T Cell Receptor Loci," *Advances in Immunology*, 1988; 43:235-275.
Camper et al., "Postnatal repression of the alpha-fetoprotein gene is enhancer independent," *Genes & Development*,1989; 3:537-546.
Carrillo et al., "The Multiple Sequence Alignment Problem in Biology," *SIAM J. Applied Math.*, 1988; 48(5):1073.
Chan et al., "Roles for Proteolysis and Trafficking in Notch Maturation and Signal Transduction," *Cell*, 1998; 94:423-426.

(56) References Cited

OTHER PUBLICATIONS

Chau et al., "Familial Alzheimer's disease Presenilin-1 mutations alter the active site conformation of γ-secretase," *J. Biol. Chem.*, May 2012; 287:17288-17296.

Chen et al., "Protein Synthesis Post-Translation Modification and Degradation," *Journal of Biological Chemistry*, 2002; 277: 36521-36526.

Chen et al., "TMP21 is a presenilin complex component that modulates gamma-secretase but not epsilon-secretase activity," Apr. 27, 2006 *Nature* 440:1208-1212.

Chun et al., "Stereoselective Synthesis of Photoreactive Peptidomimetic γ-Secretase Inhibitors," *Journal of Organic Chemistry*, 2004; 69:7344-7347.

Colbère-Garapin et al., "A new dominant hybrid selective marker for higher eukaryotic cells," Jul. 25, 1981 *J. Mol. Biol.* 150:1-14.

Cooper et al., "Designed chemical libraries for hit/lead optimization," Jun. 2000 *Innovations in Pharmaceutical Technology*; pp. 46, 48, 50, and 52-53. Available online only at: www.iptonline.com/articles/public/IPTFIVE46NP.pdf; 5 pgs.

Cravatt et al., "Activity-Based Protein Profiling: From Enzyme Chemistry to Proteomic Chemistry," *Annual Review of Biochemistry*, 2008; 77:383-414.

DeBoer et al., "A flow- and time-dependent index of ischemic injury after experimental coronary occlusion and reperfusion," Sep. 1983 *Proc. Natl. Acad. Sci. USA* 80:5784-5788.

DeJonghe et al., "Flemish and Dutch mutations in amyloid beta precursor protein have different effects on amyloid beta secretion," Oct. 5, 1998 *Neurobiol. Dis.* 5:281-286.

Deng et al., "Deletion of presenilin 1 hydrophilic loop sequence leads to impaired gamma-secretase activity and exacerbated amyloid pathology," Apr. 5, 2006 *J. Neurosci.* 26(14):3845-3854.

DeStrooper, "Aph-1, Pen-2, and Nicastrin with Presenilin generate an active gamma-Secretase complex," Apr. 10, 2003 *Neuron* 38:9-12.

Devereux et al., "A comprehensive set of sequence analysis programs for the VAX," *Nucleic Acids Research*, 1984: 12(1): 387-395.

Duff et al., "Increased amyloid-β42(43) in brains of mice expressing mutant presenilin 1," *Nature*, 1996; 383:710-713.

Edlund et al., "Cell-specific expression of the rat insulin gene: evidence for role of two distinct 5' flanking elements," *Science*, Nov. 1985; 230(4728):912-916.

Esler et al. "Transition-state analogue inhibitors of gamma-secretase bind directly to presenilin-1," Jul. 2000 *Nat. Cell Biol.* 2:428-434.

Esler et al., "Activity-dependent isolation of the presenilin—γ-secretase complex reveals nicastrin and a γsubstrate," *PNAS*, 2002; 99(5): 2720-2725.

Fan et al., "Notch pathway inhibition depletes stem-like cells and blocks engraftment in embryonal brain tumors," Aug. 1, 2006 *Cancer Res.* 66(15):7445-7452.

Foster et al., "Glucocorticoids increase the responsiveness of cells in culture to prostaglandin $E_1$," Nov. 1977 *Proc. Natl. Acad. Sci. USA* 74(11):4816-4820.

Frame et al., "Interrelationship between differentiation and malignancy-associated properties in glioma," Mar. 1984 *Br. J. Cancer* 49:269-280.

Gandy et al., "Alzheimer's presenilin 1 modulates sorting of APP and its carboxyl-terminal fragments in cerebral neurons in vivo," *Journal of Neurochemistry*, 2007; 102(3):619-626.

Gao et al., "A dimeric Smac/diablo peptide directly relieves caspase-3 inhibition by XIAP. Dynamic and cooperative regulation of XIAP by Smac/Diablo," Oct. 19, 2007 *J. Biol. Chem.* 282(42):30718-30727. Available online on Aug. 27, 2007.

Gardner et al., "The complete nucleotide sequence of an infectious clone of cauliflower mosaic virus by M13mp7 shotgun sequencing," Jun. 25, 1981 *Nucleic Acid Res.* 9(12):2871-2888.

Gilbert et al., "Useful proteins from recombinant bacteria," 1980 *Scientific American* 242(4):74-94.

Gilbert et al., "Characterization and partial purification of the plasminogen activator from human neuroblastoma cell line, SK-N-SH. A comparison with human urokinase," Jun. 24, 1982 *Biochim. Biophys. Acta* 704:450-460.

Goding, *Monoclonal Antibodies: Principles and Practice*, Academic Press; 1986:59-103.

Goeddel, *Gene Expression Technology: Methods in Enzymology 185*, Academic Press, San Diego, CA, 1990.

Golde et al., "Avoiding Unintended Toxicity," *Science*, May 2009; 324:603-604.

Gomes et al., "Glial fibrillary acidic protein (GFAP): modulation by growth factors and its implication in astrocyte differentiation," May 1999 *Braz. J. Med. Biol. Res.* 32:619-631.

Gossen et al., "Tight control of gene expression in mammalian cells by tetracycline-responsive promoters," Jun. 15, 1992 *Proc. Natl. Acad. Sci. USA* 89:5547-5551.

Gottesman, *Gene Expression Technology: Methods in Enzymology 185*, Academic Press, San Diego, CA, 1990:119-128.

Gribskov et al., eds, *Sequence Analysis Primer*, M Stockton Press, New York; 1991.

Griffin and Griffin, eds., *Computer Analysis of Sequence Data*, Part I., Humana Press, New Jersey, 1994.

Grosschedl et al., "Introduction of a μ immunoglobulin gene into the mouse germ line: specific expression in lymphoid cells and synthesis of functional antibody," Oct. 1984 *Cell* 38:647-658.

Haapala et al., "Isolation from cats of an endogenous type C virus with a novel envelope glycoprotein," Mar. 1985 *J. Virol.* 53(3):827-833.

Haass et al., "Mutations associated with a locus for familial Alzheimer's disease result in alternative processing of amyloid beta-protein precursor," Jul. 1, 1994 *J. Biol. Chem.* 269(26):17741-17748.

Hammer et al., "Diversity of alpha-fetoprotein gene expression in mice is generated by a combination of separate enhancer elements," Jan. 2, 1987 *Science* 235:53-58.

Hanahan, "Heritable formation of pancreatic beta-cell tumours in transgenic mice expressing recombinant insulin/simian virus 40 oncogenes," May 9, 1985 *Nature* 315:115-122.

Hardy et al., "The amyloid hypothesis of Alzheimer's disease: progress and problems on the road to therapeutics," Jul. 19, 2002 *Science* 297:353-356 and one page Erratum dated Sep. 27, 2002.

He et al., "Expression of $O^6$-methylguanine-DNA methyltransferase in six human medulloblastoma cell lines," Mar. 1, 1992 *Cancer Res.* 52:1144-1148.

He et al., "Notch and BCR signaling synergistically promote the proliferation of Raji B-lymphoma cells," Jun. 2009 *Leuk. Res.* 33:798-802. Available online on Oct. 19, 2008.

Henikoff, "Amino acid substitution matrices from protein blocks," *PNAS USA*, Nov. 1992; 89:10915-10919.

Herrera-Estrella et al., "Expression of chimaeric genes transferred into plant cells using a Ti-plasmid-derived vector," May 19, 1983 *Nature* 303:209-213.

Herrera-Estrella et al., "Light-inducible and chloroplast-associated expression of a chimaeric gene introduced into *Nicotiana tabacum* using a Ti plasmid vector," Jul. 12, 1984 *Nature* 310:115-120.

Hopp et al., "Prediction of protein antigenic determinants from amino acid sequences," *PNAS*, 1981; 78:3824-3828.

Hubmann et al., "Notch2 is involved in the overexpression of CD23 in B-cell chronic lymphocytic leukemia," May 15, 2002 *Blood* 99:3742-3747.

Huse et al., "Generation of a large combinatorial library of the immunoglobulin repertoire in phage lambda," *Nature*, Dec. 1989; 1275-1281.

Ida et al., "Analysis of heterogeneous βA4 peptides in human cerebrospinal fluid and blood by a newly developed sensitive Western blot assay," Sep. 13, 1996 *J. Biol. Chem.* 271(37):22908-22914.

Ikeuchi et al., "The Notch ligands Delta1 and Jagged2 are substrates for presenilin-dependent 'gamma-secretase' cleavage," Mar. 7, 2003 *J. Biol. Chem.* 278(10):7751-7754. Available online on Jan. 24, 2003.

(56) References Cited

OTHER PUBLICATIONS

International Preliminary Report on Patentability issued Mar. 12, 2013, in Switzerland for International Patent Application No. PCT/US2011/050688, filed Sep. 7, 2011.
International Search Report mailed Jun. 29, 2012, in Korea for International Patent Application No. PCT/US2011/050688, filed Sep. 7, 2011.
Jarrett et al., "The carboxy terminus of the beta amyloid protein is critical for the seeding of amyloid formation: implications for the pathogenesis of Alzheimer's disease," May 11, 1993 *Biochem.* 32(18):4693-4697.
Kang et al., "The precursor of Alzheimer's disease amyloid A4 protein resembles a cell-surface receptor," Feb. 19, 1987 *Nature* 325:733-736.
Kaufman et al., "Translational efficiency of polycistronic mRNAs and their utilization to express heterologous genes in mammalian cells," *EMBO J.*, 1987; 6:187-193.
Keller et al., "A Faster Migrating Variant Masquerades as NICD When Performing in Vitro γ-Secretase Assays with Bacterially Expressed Notch Substrates," *Biochemistry*, 2006; 45:5351-5358.
Kelsey et al., "Species- and tissue-specific expression of human alpha$_1$-antitrypsin in transgenic mice," Apr. 1987 *Genes Dev.* 1:161-171.
Kessel et al., "Murine developmental control genes," *Science*, Jul. 1990; 249:374-379.
Khorkova et al., "Modulation of amyloid precursor protein processing by compounds with various mechanisms of action: detection by liquid phase electrochemiluminescent system," Aug. 1, 1998 *J. Neurosci. Meth.* 82:159-166.
Kitaguchi et al., "Novel precursor of Alzheimer's disease amyloid protein shows protease inhibitory activity," Feb. 11, 1988 *Nature* 331:530-532.
Kogoshi et al., "Gamma-secretase inhibitors suppress the growth of leukemia and lymphoma cells," Jul. 2007 *Oncol. Rep.* 18:77-80.
Kohler et al., "Continuous cultures of fused cells secreting antibody of predefined specificity," *Nature*, 1975; 256:495-497.
Kojro et al., "The non-amyloidogenic pathway: structure and function of alpha-secretases," 2005 *Subcell. Biochem.* 38:105-127.
Kollias et al., "Regulated expression of human $^A$gamma-, beta-, and hybrid gamma/beta-globin genes in transgenic mice: manipulation of the developmental expression patterns," Jul. 4, 1986 *Cell* 46:89-94.
Kopan et al., "Signal transduction by activated mNotch: Importance of proteolytic processing and its regulation by the extracellular domain," *PNAS*, 1996; 93:1683-1688.
Kopan et al., "A common enzyme connects Notch signaling and Alzheimer's disease," Nov. 15, 2000 *Genes. Dev.* 14:2799-2806.
Kounnas et al., "Modulation of gamma-secretase reduces beta-amyloid deposition in a transgenic mouse model of Alzheimer's disease," Sep. 9, 2010 *Neuron* 67:769-780.
Kozbor, "A human hybrid myeloma for production of human monoclonal antibodies," *J Immunol.*, 1984; 133:3001-5.
Krumlauf et al., "Developmental regulation of alpha-fetoprotein genes in transgenic mice," Jul. 1985 *Mol. Cell. Biol.* 5(7):1639-1648.
Kruse et al., "Characterization of a continuous human glioma cell line DBTRG-05MG: growth kinetics, karyotype, receptor expression, and tumor suppressor gene analyses," Sep.-Oct. 1992 *In Vitro Cell. Dev. Biol.* 28A:609-614.
Kuo et al., "Water-soluble Abeta (N-40, N-42) oligomers in normal and Alzheimer disease brains," Feb. 23, 1996 *J. Biol. Chem.* 271(8):4077-4081.
Kurjan et al. "Structure of a yeast pheromone gene (*MFα*): A putative α-factor precursor contains four tandem copies of mature α-factor," *Cell*, Oct. 1982; 30:933-943.
Kyte et al., "A simple method for displaying the hydropathic character of a protein," *Journal of Molecular Biology*, May 1982; 157:105-132.

Lai et al., "Presenilin-1 and presenilin-2 exhibit distinct yet overlapping gamma-secretase activities," Jun. 20, 2003 *J. Biol. Chem.* 278(25):22475-22481. Available online on Apr. 8, 2003.
Lammich et al., "Presenilin-dependent intramembrane proteolysis of CD44 leads to the liberation of its intracellular domain and the secretion of an Abeta-like peptide," Nov. 22, 2002 *J. Biol. Chem.* 277(47):44754-44759. Available online on Sep. 9, 2002.
Lee et al. "Hyperaccumulation of FAD-linked presenilin 1 variants in vivo," *Nature Medicine*, 1997; 3:756-760.
Leder et al., "Consequences of widespread deregulation of the c-myc gene in transgenic mice: multiple neoplasms and normal development," May 23, 1986 *Cell* 45:485-495.
Lei et al., "Soluble oligomers of the intramembrane serine protease YqgP are catalytically active in the absence of detergents," Nov. 18, 2008 *Biochem.* 47:11920-11929. Available online on Oct. 21, 2008.
Lesk, A.M., ed., *Computational Molecular Biology*, Oxford University Press; New York, NY, 1988.
Levy-Lahad et al., "Candidate gene for the chromosome 1 familial Alzheimer's disease locus," *Science*, 1995; 269:973-977.
Li et al., "Photoactivated γ-secretase inhibitors directed to the active site covalently label presenilin 1," Jun. 8, 2000 *Nature* 405:689-694.
Li et al., "Presenilin 1 is linked with γ-secretase activity in the detergent solubilized state," May 23, 2000 *Proc. Natl. Acad. Sci. USA* 97(11):6183-6143.
Li, Yueming, "Regulation and Function of Gamma-Secretase," Grant Abstract, Grant No. AG026660 [online]. National Institute on Aging, National Institutes of Health, project dates Aug. 1, 2005 to Jul. 31, 2011 [retrieved on Jan. 7, 2011]. Retrieved from the Internet: <http://projectreporter.nih.gov/pr_Prj_info_desc_dtls.cfm?aid=7663911&icde=6610158&print=yes>; 2 pgs.
Lichtenthaler et al., "Mutations in the transmembrane domain of APP altering γ-secretase specificity," Dec. 9, 1997 *Biochem.* 36:15396-15403.
Lichtenthaler et al., "A novel substrate for analyzing Alzheimer's disease gamma-secretase," Jun. 25, 1999 *FEBS Lett.* 453:288-292.
Logan et al., "Adenovirus tripartite leader sequence enhances translation of mRNAs late after infection," Jun. 1984 *Proc. Natl. Acad. Sci. USA* 81:3655-3659.
Lowy et al., "Isolation of transforming DNA: cloning the hamster aprt gene," Dec. 1980 *Cell* 22:817-823.
Luckow et al, "High level expression of nonfused foreign genes with *Autographa californica* nuclear polyhedrosis virus expression vectors," *Virology*, May 1989; 170:31-39.
MacDonald, "Expression of the pancreatic elastase I gene in transgenic mice," Jan.-Feb. 1987 *Hepatology* 7(1):42S-51S.
Magram et al., "Developmental regulation of a cloned adult β-globin gene in transgenic mice," May 23, 1985 *Nature* 315:338-340.
Marambaud et al., "A presenilin-1/-secretase cleavage releases the E-cadherin intracellular domain and regulates disassembly of adherens junctions," *The EMBO Journal*, 2002; 21:1948-1956.
Marambaud et al., "A CBP Binding Transcriptional Repressor Produced by the PS1/∉-Cleavage of N-Cadherin Is Inhibited by PS1 FAD Mutations," *Cell*, 2003; 114: 635-645.
Marciniszyn et al., "Mode of inhibition of acid proteases by pepstatin," Nov. 25, 1976 *J. Biol. Chem.* 251(22):7088-7094.
Mason et al., "The hypogonadal mouse: reproductive functions restored by gene therapy," Dec. 12, 1986 *Science* 234:1372-1378.
McCafferty et al., "Mutational Analysis of Potential Zinc-Binding Residues in the Active Site of the Enterococcal D-Ala-D-Ala Dipeptidase VanX," Aug. 26, 1997 *Biochem.* 36:10498-10505.
Moehlmann et al., "Presenilin-1 mutations of leucine 166 equally affect the generation of the Notch and APP intracellular domains independent of their effect on Aβ42 production," *PNAS;* 2002; 99:8025-8030.
Morelli et al., "Neuronal and glial cell type-specific promoters within adenovirus recombinants restrict the expression of the apoptosis-inducing molecule Fas ligand to predetermined brain cell types, and abolish peripheral liver toxicity," Mar. 1999 *J. Gen. Virol.* 80:571-583.
Morrison, "Success in Specification," *Nature*, Apr. 1994; 368:812-813.

(56) References Cited

OTHER PUBLICATIONS

Müller et al., "Physiological Functions of APP Family Proteins," *Cold Spring Harbor Perspectives in Medicine*, Feb. 2012; 2(2): a006288.
Mulligan et al., "Selection for animal cells that express the *Escherichia coli* gene coding for xanthine-guanine phosphoribosyltransferase," Apr. 1981 *Proc. Natl. Acad. Sci. USA* 78(4):2072-2076.
Munson et al., "LIGAND: A versatile computerized approach for characterization of ligan-binding systems," *Analytical Biochemistry*, 1980; 107:220-239.
Murayama et al., "Twenty-nine missense mutations linked with familial Alzheimer's disease alter the processing of presenilin 1," *Progress in Neuro-Psychopharmacology and Biological Psychiatry*, 1999; 23(5): 905-913.
Nakajima et al., "Notch-1 activation by familial Alzheimer's disease (FAD)-linked mutant forms of presenilin-1," *Journal of Neuroscience Research*, 2000; 62:311-317.
Neet et al., "Thematic Minireview Series on the Molecular Basis of Alzheimer Disease," *The Journal of Biological Chemistry*, Oct. 2008; 283(44): 29613-29614.
National Center for Biotechnology Information, National Library of Medicine, National Institutes of Health, GenBank Locus AAC83813, Accession No. AAC83813, "maltose binding protein [Expression vector pMBP-parallel1]," [online]. Bethesda, MD [retrieved on Jan. 10, 2011]. Retrieved from the Internet: < http://www.ncbi.nlm.nih.gov/protein/3983122>; 1 pg.
National Center for Biotechnology Information, National Library of Medicine, National Institutes of Health, GenBank Locus AF308602, Accession No. AF308602, "Homo sapiens NOTCH 1 (N1) mRNA, complete cds," [online]. Bethesda, MD [retrieved on Aug. 2, 2013]. Retrieved from the Internet: <http://www.ncbi.nlm.nih.gov/nuccore/af308602>; 3 pgs.
National Center for Biotechnology Information, National Library of Medicine, National Institutes of Health, GenBank Locus NM_003183, Accession No. NM_003183, "Homo sapiens ADAM metallopeptidase domain 17 (ADAM17), mRNA," [online]. Bethesda, MD [retrieved on Jan. 10, 2011]. Retrieved from the Internet: < http://www.ncbi.nlm.nih.gov/nuccore/73747888>; 5 pgs.
National Center for Biotechnology Information, National Library of Medicine, National Institutes of Health, GenBank Locus XP_002810439, Accession No. XP_002810439, "PREDICTED: synaptonemal complex protein 1 isoform 2 [Pongo abelii]," [online]. Bethesda, MD [retrieved on Aug. 2, 2013]. Retrieved from the Internet: <http://www.ncbi.nlm.nih.gov/protein/XP_002810439.1>; 1 pg.
National Center for Biotechnology Information, National Library of Medicine, National Institutes of Health, GenBank Locus Y00264, Accession No. Y00264, "Human mRNA for amyloid A4 precursor of Alzheimer's disease," [online]. Bethesda, MD [retrieved on Jan. 7, 2011]. Retrieved from the Internet: <http://www.ncbi.nlm.nih.gov/nuccore/28525>; 2 pgs.
Needleman et al., "Needleman-Wunsch Algorithm for Sequence Similarity Searches," *J. Mol. Biol.*, 1970; 48: 443-453.
Neet et al., "Thematic Minireview Series on the Molecular Basis of alzheimer Disease," *The Journal of Biological Chemistry*, Oct. 2008; 283(44):29613-29614.
Nilsberth et al., "The 'Arctic' APP mutation (E693G) causes Alzheimer's disease by enhanced Abeta protofibril formation," Sep. 2001 *Nat. Neurosci.* 4(9):887-893.
Nitsch et al., "Release of Alzheimer amyloid precursor derivatives stimulated by activation of muscarinic acetylcholine receptors," Oct. 9, 1992 *Science* 258:304-307.
O'Hare et al., "Transformation of mouse fibroblasts to methotrexate resistance by a recombinant plasmid expressing a prokaryotic dihydrofolate reductase," Mar. 1981 *Proc. Natl. Acad. Sci. USA* 78(3):1527-1531.
Olmsted et al., "Isolation of microtubule protein from cultured mouse neuroblastoma cells," Jan. 1970 *Proc. Natl. Acad. Sci. USA* 65(1):129-136.

Olopade et al., "Molecular analysis of deletions of the short arm of chromosome 9 in human gliomas," May 1, 1992 *Cancer Res.* 52:2523-2529.
Ornitz et al., "Elastase I promoter directs expression of human growth hormone and SV40 T antigen genes to pancreatic acinar cells in transgenic mice," 1985 *Cold Spring Harbor Symp. Quant. Biol.* 50:399-409.
Pinkert et al., "An albumin enhancer located 10 kb upstream functions along with its promoter to direct efficient, liver-specific expression in transgenic mice," May 1987 *Genes Dev.* 1:268-276.
Placanica et al., "Pen2 and presenilin-1 modulate the dynamic equilibrium of presenilin-1 and presenilin-2 gamma-secretase complexes," Jan. 30, 2009 *J. Biol. Chem.* 284(5):2967-2977. Available online on Nov. 25, 2008.
Placanica et al., "Gender- and age-dependent gamma-secretase activity in mouse brain and its implication in sporadic Alzheimer disease," 2009 *PloS One* 4(4):e5088; 9 pgs. Available online on Apr. 7, 2009.
Placanica et al., "Characterization of an Atypical γ-Secretase Complex from Hematopoietic Origin," Apr. 6, 2010 *Biochem.* 49:2796-2804. Available online on Feb. 23, 2010.
Ponte et al., "A new A4 amyloid mRNA contains a domain homologous to serine proteinase inhibitors," Feb. 11, 1988 *Nature* 331:525-527.
Pontén et al., "Long term culture of normal and neoplastic human glia," 1968 *Acta Pathol. Microbiol. Scand.* 74:465-486.
Postina et al., "A disintegrin-metalloproteinase prevents amyloid plaque formation and hippocampal defects in an Alzheimer disease mouse model," May 2004 *J. Clin .Invest.* 113(10):1456-1464.
Postina et al., "Erratum: A disintegrin-metalloproteinase prevents amyloid plaque formation and hippocampal defects in an Alzheimer disease mouse model," Aug. 2004 *J. Clin .Invest.* 114(4):598-599.
Queen et al., "Immunoglobulin gene transcription is activated by downstream sequence elements," *Cell*, Jul. 1983; 33:741-748.
Radany et al., "Directed establishment of rat brain cell lines with the phenotypic characteristics of type 1 astrocytes," Jul. 15, 1992 *Proc. Natl. Acad. Sci. USA* 89:6467-6471.
Readhead et al., "Expression of a myelin basic protein gene in transgenic shiverer mice: correction of the dysmyelinating phenotype," Feb. 27, 1987 *Cell* 48:703-712.
Redmond et al., "Nuclear Notch1 signaling and the regulation of dendritic development," *Nature Neuroscience*, 2000; 3:30-40.
Reed, "Molecular biology of chronic lymphocytic leukemia," Feb. 1998 *Semin. Oncol.* 25(1):11-18.
Sambrook et al., *Molecular Cloning: A Laboratory Manual*, 2$^{nd}$ Ed., Cold Spring Harbor Laboratory, Cold Spring Harbor Laboratory Press, Cold Spring Harbor, NY, 1989, Chapters 16 and 17.
Santerre et al., "Expression of prokaryotic genes for hygromycin B and G418 resistance as dominant-selection markers in mouse L cells," Oct. 1984 *Gene* 30:147-156.
Sato et al., "Enzyme Catalysis and Regulation," *Journal of Biological Chemistry*, 2003; 278:24294-24301.
Schatz, "Use of Peptide Libraries to Map the Substrate Specificity of a Peptide-Modifying Enzyme: A 13 Residue Consensus Peptide Specifies Biotinylation in *Escherichia coli*," Oct. 1993 *Nat. Biotechnol.* 11:1138-1143.
Schechter et al., "On the size of the active site in proteases. I. Papain," *Biochemical and Biophysical Research Communications*, 1967; 27(2):157-162.
Schultz et al., "Expression and secretion in yeast of a 400-kda envelope glycoprotein derived from epstein-barr virus," *Gene* 1987; 54:113-123.
Seed, "An LFA-3 cDNA encodes a phospholipid-linked membrane protein homologous to its receptor CD2," *Nature*, Oct. 1987; 329:840-842.
Seiffert et al., "Presenilin-1 and -2 are molecular targets for gamma-secretase inhibitors," Nov. 3, 2000 *J. Biol. Chem.* 275(44):34086-34091.
Selkoe, "The cell biology of beta-amyloid precursor protein and presenilin in Alzheimer's disease," Nov. 1998 *Trends Cell Bio.* 8:447-453.
Selkoe, "Translating cell biology into therapeutic advances in Alzheimer's disease," Jun. 24, 1999 *Nature* 399:A23-A31.

(56) References Cited

OTHER PUBLICATIONS

Selkoe et al., "In search of gamma-secretase: presenilin at the cutting edge," May 23, 2000 *Proc. Natl. Acad. Sci. USA* 97:5690-5692.
Selkoe, "Alzheimer's disease: genes, proteins, and therapy," Apr. 2001 *Physiol. Rev.* 81(2):741-766.
Selkoe et al., "Notch and Presenilin: regulated intramembrane proteolysis links development and degeneration," 2003 *Ann. Rev. Neurosci.* 26:565-597. Available online on Apr. 18, 2003.
Serneels et al., "γ-Secretase Heterogeneity in the aph1 Subunit: Relevance for Alzheimer's Disease," *Science*, May 2009; 324:639-642.
Shah et al., "Nicastrin functions as a gamma-secretase-substrate receptor," Aug. 12, 2005 *Cell* 122:435-447.
Shani, "Tissue-specific expression of rat myosin light-chain 2 gene in transgenic mice," Mar. 21, 1985 *Nature* 314:283-286.
Shearman et al., "L-685,458, an aspartyl protease transition state mimic, is a potent inhibitor of amyloid β-protein precursor γ-secretase activity," Aug. 1, 2000 *Biochem.* 39:8698-8704. Available online on Jul. 6, 2000.
Shelton et al., "An exo-cell assay for examining real-time γ-secretase activity and inhibition," *Molecular Neurodegeneration*, 2009; 4:22.
Shelton et al., "A miniaturized 1536-well format gamma-secretase assay," Oct. 2009 *Assay Drug Dev. Technol.* 7(5):461-470.
Shelton et al., "Modulation of gamma-secretase specificity using small molecule allosteric inhibitors," Dec. 1, 2009 *Proc. Natl. Acad. Sci. USA* 106(48):20228-20233. Available online on Nov. 11, 2009.
Sherrington et al., "Cloning of a gene bearing missense mutations in early-onset familial Alzheimer's disease," *Nature*, 1995; 375:754-760.
Six et al., "The Notch ligand Delta1 is sequentially cleaved by an ADAM protease and gamma-secretase," Jun. 24, 2003 *Proc. Natl. Acad. Sci. USA* 100:7638-7643. Available online on Jun. 6, 2003.
Skovronsky et al., "Protein kinase C-dependent alpha-secretase competes with beta-secretase for cleavage of amyloid-beta precursor protein in the trans-golgi network," Jan. 28, 2000 *J. Biol. Chem.* 275(4):2568-2575.
Smith et al., "Production of Human Beta Interferon in Insect Cells Infected with a Caculovirus Expression Vector," *Mol Cell Biol*, 1983; 3:2156-2165.
Smith et al., "Single-step purification of polypeptides expressed in *Escherichia coli* as fusions with glutathione S-transferase," *Gene*, Jul. 1988: 67:31-40.
Smith, D. W., ed., *Biocomputing: Informatics and Genome Projects*, Academic Press, New York, NY, 1993.
Song et al., "Proteolytic release and nuclear translocation of Notch-1 are induced by presenilin-1 and impaired by pathogenic presenilin-1 mutations," *PNAS*, 1999; 96 (12): 6959-6963.
Steinhilb et al., "ELISA analysis of beta-secretase cleavage of the Swedish amyloid precursor protein in the secretory and endocytic pathways," Mar. 2002 *J. Neurochem.* 80:1019-1028.
Stephens et al., "Metabolites of the beta-amyloid precursor protein generated by beta-secretase localise to the trans-Golgi network and late endosome in 293 cells," Oct. 15, 1996 *J. Neurosci. Res.* 46:211-225.
Struhl et al., "Requirements for presenilin-dependent cleavage of notch and other transmembrane proteins," *Mol. Cell.*, Sep. 2000; 6:625-636.
Studier et al., *Gene Expression Technology: Methods in Enzymology 185*, Academic Press, San Diego, CA, 1990:60-89.
Sugimoto et al., "Determination of cell surface membrane antigens common to both human neuroblastoma and leukemia-lymphoma cell lines by a panel of 38 monoclonal antibodies," Jul. 1984 *J. Natl. Can. Inst.* 73(1):51-57.
Swift et al., "Tissue-specific expression of the rat pancreatic elastase I gene in transgenic mice," Oct. 1984 *Cell* 38:639-646.
Szybalska et al., "Genetics of human cell lines, IV. DNA-mediated heritable transformation of a biochemical trait," Dec. 15, 1962 *Proc. Natl. Acad. Sci. USA* 48:2026-2034.

Tabuchi et al., "Inducibility of BDNF gene promoter I detected by calcium-phosphate-mediated DNA transfection is confined to neuronal but not to glial cells," Dec. 30, 1998 *Biochem. Biophys. Res. Comm.* 253:818-823.
Takami et al., "γ-Secretase: Successive Tripeptide and Tetrapeptide Release from the Transmembrane Domain of β-Carboxyl Terminal Fragment," *Journal of Neuroscience*, 2009; 29(41):13042-13052.
Thinakaran et al., "Amyloid precursor protein trafficking, processing, and function," Oct. 31, 2008 *J. Biol. Chem.* 283(44):29615-29619. Available online on Jul. 23, 2008.
Tian et al., "An APP inhibitory domain containing the Flemish mutation residue modulates gamma-secretase activity for Abeta production," Feb. 2010 *Nat. Struct. Mol. Biol.* 17(2):151-158. Available online on Jan. 10, 2010.
Tian et al., "Dual role of alpha-secretase cleavage in the regulation of gamma-secretase activity for amyloid production," Oct. 15, 2010 *J. Biol. Chem.* 285(42):32549-32556. Available online on Jul. 30, 2010.
Trowbridge et al., "Establishment and characterization of ferret cells in culture," Nov. 1982 *In Vitro* 18(11):952-960.
Tumilowicz et al., "Definition of a continuous human cell line derived from neuroblastoma," Aug. 1970 *Cancer Res.* 30:2110-2118.
Universal Protein Resource (UniProt) Consortium, UniProt Knowledgebase (UniProtKB), UniProtKB/Swiss-Prot Ref. P05067 (A4_HUMAN), "Amyloid beta A4 protein," [online]. Washington, D.C. [retrieved on Jan. 7, 2011]. Retrieved from the Internet: <http://www.uniprot.org/uniprot/P05067>; 44 pgs.
van Tetering et al., "Metalloprotease ADAM10 Is Required for Notch 1 Site 2 Cleavage," *J. Biol. Chem.*, 2009; 284(45): 31018-31027.
Vassar et al., "β-secretase cleavage of Alzheimer's amyloid precursor protein by the transmembrane aspartic protease BACE," Oct. 22, 1999 *Science* 286:735-741.
Vetrivel et al., "Evidence that CD147 modulation of beta-amyloid (Abeta) levels is mediated by extracellular degradation of secreted Abeta," Jul. 11, 2008 *J. Biol. Chem.* 283(28):19489-19498. Available online on May 1, 2008.
Villa-Kamaroff et al., "A bacterial clone synthesizing proinsulin," Aug. 1978 *Proc. Natl. Acad. Sci. USA* 75(8):3727-3731.
Voet et al., *Biochemistry*, John Wiley & Sons: New York, NY; copyright 1990. Cover page, publisher's page, and p. 66-71.
von Heijne, G., *Sequence Analysis in Molecular Biology*, Academic Press, New York, 1987.
Wada et al., "Codon usage tabulated from the GenBank genetic sequence data," *Nucleic Acids Research*, May 1992; 20(Suppl):2111-2118.
Wagner et al., "Nucleotide sequence of the thymidine kinase gene of herpes simplex virus type 1," Mar. 1981 *Proc. Natl. Acad. Sci. USA* 78(3):1441-1445.
Wang et al., "Presenilin 1 familial Alzheimer's disease mutation leads to defective associative learning and impaired adult neurogenesis," *Neuroscience*, 2004; 126(2):305-312.
Wang et al., "Wild-type Presenilin 1 Protects against Alzheimer Disease Mutation-induced Amyloid Pathology," *J. Biol. Chem.*, 2006; 281:15330-15336.
Weng et al., "Activating mutations of NOTCH1 in human T cell acute lymphoblastic leukemia," Oct. 2004 *Science* 306:269-271.
Wigler et al., "Transfer of purified herpes virus thymidine kinase gene to cultured mouse cells," May 1977 *Cell* 11:223-232.
Wigler et al., "Transformation of mammalian cells with an amplifiable dominant-acting gene," Jun. 1980 *Proc. Natl. Acad. Sci. USA* 77(6):3567-3570.
Wilkinson, "Ultimate Abs," *The Scientist*, Apr. 2000; 14(8): pp. 25-28.
Winoto et al., "A novel, inducible and T cell-specific enhancer located at the 3' end of the T cell receptor α locus," *EMBO J.*, 1989; 8(3):729-733.
Wolfe et al., "Two transmembrane aspartates in presenilin-1 required for presenilin endoproteolysis and γ-secretase activity," Apr. 8, 1999 *Nature* 398:513-517.
Written Opinion mailed Jun. 29, 2012, in Korea for International Patent Application No. PCT/US2011/050688, filed Sep. 7, 2011.

(56) References Cited

OTHER PUBLICATIONS

Yamamoto et al., "Identification of a functional promoter in the long terminal repeat of Rous sarcoma virus," Dec. 1980 *Cell* 22:787-797.
Yang et al., "Electrochemiluminescence: A new diagnostic and research tool," Feb. 1994 *Nat. Biotechnol.* 12:193-194.
Yang et al., "Stereo-controlled synthesis of novel photoreactive γ-secretase inhibitors," Feb. 1, 2009 *Bioorg. Med. Chem. Lett.* 19:922-925.
Yang et al., "In vivo manifestation of Notch related phenotypes in zebrafish treated with Alzheimer's amyloid reducing γ-secretase inhibitors," Jun. 2010 *J. Neurochem.* 113:1200-1209. Available online on Mar. 12, 2010.
Yin et al., "γ- Secretase Substrate Concentration Modulates the Abeta42/Abeta40 Ratio: Implications for Alzheimer Disease," Aug. 10, 2007 *J. Biol. Chem.* 282(32):23639-23644. Available online on Jun. 7, 2007.
Zhang et al., "A simple statistical parameter for use in evaluation and validation of high throughput screening assays," Apr. 1999 *J. Biomol. Scrn.* 4(2):67-73.
Zheng et al., "The amyloid precursor protein: beyond amyloid," *Molecular Neurodegeneration*, Jul. 2006; 1:5.
Zhou et al., "CD147 is a regulatory subunit of the gamma-secretase complex in Alzheimer's disease amyloid beta-peptide production," May 24, 2005 *Proc. Natl. Acad. Sci. USA* 102(21):7499-7504. Available online on May 12, 2005.
Wagner et al. "Tuning *Escherichia coli* for membrane protein overexpresson", PNAS. 2008. 105:38:14371-14376.
Zoonens et al. "Expression of Membrane Proteins at the *Escherichia coli* Membrane for Structural Studies", *Heterologous Expression of Membrane Proteins*, 2010. 610:49-66.
Chapter 11—pp. 200-201, "Protein Biological Pesticide" in *Protein Bio-Pesticides*. Qui (Ed.) 2010. (English translation from Chinese).
Chapter 11—pp. 200-201, "Protein Biological Pesticide" in *Protein Bio-Pesticides*. Qui (Ed.) 2010. (Chinese).
Mizutani et al. "Conservation of the biochemical mechanisms of signal transduction among mammalian Notch family members," May 30, 2001, *PNAS*, 98(6):9026-9031.

* cited by examiner

Figure 4

```
TGGCGAATGGGACGCGCCCTGTAGCGGCGCATTAAGCGCGGCGGGTGTGGTGGTTACGCGCAGCGTG
ACCGCTACACTTGCCAGCGCCCTAGCGCCCGCTCCTTTCGCTTTCTTCCCTTCCTTTCTCGCCACGT
TCGCCGGCTTTCCCCGTCAAGCTCTAAATCGGGGGCTCCCTTTAGGGTTCCGATTTAGTGCTTTACG
GCACCTCGACCCCAAAAAACTTGATTAGGGTGATGGTTCACGTAGTGGGCCATCGCCCTGATAGACG
GTTTTTCGCCCTTTGACGTTGGAGTCCACGTTCTTTAATAGTGGACTCTTGTTCCAAACTGGAACAA
CACTCAACCCTATCTCGGTCTATTCTTTTGATTTATAAGGGATTTTGCCGATTTCGGCCTATTGGTT
AAAAAATGAGCTGATTTAACAAAAATTTAACGCGAATTTTAACAAAATATTAACGTTTACAATTTCA
GGTGGCACTTTTCGGGGAAATGTGCGCGGAACCCCTATTTGTTTATTTTTCTAAATACATTCAAATA
TGTATCCGCTCATGAATTAATTCTTAGAAAAACTCATCGAGCATCAAATGAAACTGCAATTTATTCA
TATCAGGATTATCAATACCATATTTTTGAAAAAGCCGTTTCTGTAATGAAGGAGAAAACTCACCGAG
GCAGTTCCATAGGATGGCAAGATCCTGGTATCGGTCTGCGATTCCGACTCGTCCAACATCAATACAA
CCTATTAATTTCCCCTCGTCAAAAATAAGGTTATCAAGTGAGAAATCACCATGAGTGACGACTGAAT
CCGGTGAGAATGGCAAAAGTTTATGCATTTCTTTCCAGACTTGTTCAACAGGCCAGCCATTACGCTC
GTCATCAAAATCACTCGCATCAACCAAACCGTTATTCATTCGTGATTGCGCCTGAGCGAGACGAAAT
ACGCGATCGCTGTTAAAAGGACAATTACAAACAGGAATCGAATGCAACCGGCGCAGGAACACTGCCA
GCGCATCAACAATATTTTCACCTGAATCAGGATATTCTTCTAATACCTGGAATGCTGTTTTCCCGGG
GATCGCAGTGGTGAGTAACCATGCATCATCAGGAGTACGGATAAAATGCTTGATGGTCGGAAGAGGC
ATAAATTCCGTCAGCCAGTTTAGTCTGACCATCTCATCTGTAACATCATTGGCAACGCTACCTTTGC
CATGTTTCAGAAACAACTCTGGCGCATCGGGCTTCCCATACAATCGATAGATTGTCGCACCTGATTG
CCCGACATTATCGCGAGCCCATTTATACCCATATAAATCAGCATCCATGTTGGAATTTAATCGCGGC
CTAGAGCAAGACGTTTCCCGTTGAATATGGCTCATAACACCCCTTGTATIACTGTTTATGTAAGCAG
ACAGTTTTATTGTTCATGACCAAAATCCCTTAACGTCAGTTTTCGTTCCACTGAGCGTCAGACCCCG
TAGAAAAGATCAAAGGATCTTCTTGAGATCCTTTTTTTCTGCGCGTAATCTGCTGCTTGCAAACAAA
AAAACCACCGCTACCAGCGGTGGTTTGTTTGCCGGATCAAGAGCTACCAACTCTTTTTCCGAAGGTA
ACTGGCTTCAGCAGAGCGCAGATACCAAATACTGTCCTTCTAGTGTAGCCGTAGTTAGGCCACCACT
TCAAGAACTCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGCAGCGGTCG
GGCTGAACGGGGGGTTCGTGCACACAGCCCAGCTTGCAGCGAACGACCTACACCGAACTGAGATACC
TACAGCGTGAGCTATGAGAAAGCGCCACGCTTCCCGAAGGGAGAAAGGCGGACAGGTATCCGGTAAG
CGGCAGGGTCGGAACAGGAGAGCGCACGAGGGAGCTTCCAGGGGGAAACGCCTGGTATCTTTATAGT
CCTGTCGGGTTTCGCCACCTCTGACTTGAGCGTCGATTTTTGTGATGCTCGTCAGGGGGCGGAGCC
TATGGAAAAACGCCAGCAACGCGGCCTTTTTACGGTTCCTGGCCTTTTGCTGGCCTTTTGCTCACAT
GTTCTTTCCTGCGTTATCCCCTGATTCTGTGGATAACCGTATTACCGCCTTTGAGTGAGCTGATACC
GCTCGCCGCAGCCGAACGACCGAGCGCAGCGAGTCAGTGAGCGAGGAAGCGGAAGAGCGCCTGATGC
GGTATTTTCTCCTTACGCATCTGTGCGGTATTTCACACCGCATATATGGTGCACTCTCAGTACAATC
TGCTCTGATGCCGCATAGTTAAGCCAGTATACACTCCGCTATCGCTACGTGACTGGGTCATGGCTGC
GCCCCGACACCCGCCAACACCCGCTGACGCGCCCTGACGGGCTTGTCTGCTCCCGGCATCCGCTTAC
AGACAAGCTGTGACCGTCTCCGGGAGCTGCATGTGTCAGAGGTTTTCACCGTCATCACCGAAACGCG
CGAGGCAGCTGCGGTAAAGCTCATCAGCGTGGTCGTGAAGCGATTCACAGATGTCTGC
```

Figure 4 (Continue)

```
CTGTTCATCCGCGTCCAGCTCGTTGAGTTTCTCCAGAAGCGTTAATGTCTGGCTTCTGATAAAGCGG
GCCATGTTAAGGGCGGTTTTTTCCTGTTTGGTCACTGATGCCTCCGTGTAAGGGGGATTTCTGTTCA
TGGGGGTAATGATACCGATGAAACGAGAGAGGATGCTCACGATACGGGTTACTGATGATGAACATGC
CCGGTTACTGGAACGTTGTGAGGGTAAACAACTGGCGGTATGGATGCGGCGGGACCAGAGAAAAATC
ACTCAGGGTCAATGCCAGCGCTTCGTTAATACAGATGTAGGTGTTCCACAGGGTAGCCAGCAGCATC
CTGCGATGCAGATCCGGAACATAATGGTGCAGGGCGCTGACTTCCGCGTTCCAGACTTTACGAAAC
ACGGAAACCGAAGACCATTCATGTTGTTGCTCAGGTCGCAGACGTTTTGCAGCAGCAGTCGCTTCAC
GTTCGCTCGCGTATCGGTGATTCATTCTGCTAACCAGTAAGGCAACCCCGCCAGCCTAGCCGGGTCC
TCAACGACAGGAGCACGATCATGCGCACCCGTGGGGCCGCCATGCCGGCGATAATGGCCTGCTTCTC
GCCGAAACGTTTGGTGGCGGGACCAGTGACGAAGGCTTGAGCGAGGGCGTGCAAGATTCCGAATACC
GCAAGCGACAGGCCGATCATCGTCGCGCTCCAGCGAAAGCGGTCCTCGCCGAAAATGACCCAGAGCG
CTGCCGGCACCTGTCCTACGAGTTGCATGATAAAGAAGACAGTCATAAGTGCGGCGACGATAGTCAT
GCCCCGCGCCACCGGAAGGAGCTGACTGGGTTGAAGCTCTCAAGGGCATCGGTCGAGATCCCGGT
GCCTAATGAGTGAGCTAACTTACATTAATTGCGTTGCGCTCACTGCCCGCTTTCCAGTCGGGAAACC
TGTCGTGCCAGCTGCATTAATGAATCGGCCAACGCGCGGGGAGAGGCGGTTTGCGTATTGGGCGCCA
GGGTGGTTTTTCTTTTCACCAGTGAGACGGGCAACAGCTGATTGCCCTTCACCGCCTGGCCCTGAGA
GAGTTGCAGCAAGCGGTCCACGCTGGTTTGCCCCAGCAGGCGAAAATCCTGTTTGATGGTGGTTAAC
GGCGGGATATAACATGAGCTGTCTTCGGTATCGTCGTATCCCACTACCGAGATATCCGCACCAACGC
GCAGCCCGGACTCGGTAATGGCGCGCATTGCGCCCAGCGCCATCTGATCGTTGGCAACCAGCATCGC
AGTGGGAACGATGCCCTCATTCAGCATTTGCATGGTTTGTTGAAAACCGGACATGGCACTCCAGTCG
CCTTCCCGTTCCGCTATCGGCTGAATTTGATTGCGAGTGAGATATTTATGCCAGCCAGCCAGACGCA
GACGCGCCGAGACAGAACTTAATGGGCCCGCTAACAGCGCGATTTGCTGGTGACCCAATGCGACCAG
ATGCTCCACGCCCAGTCGCGTACCGTCTTCATGGGAGAAAATAATACTGTTGATGGGTGTCTGGTCA
GAGACATCAAGAAATAACGCCGGAACATTAGTGCAGGCAGCTTCCACAGCAATGGCATCCTGGTCAT
CCAGCGGATAGTTAATGATCAGCCCACTGACGCGTTGCGCGAGAAGATTGTGCACCGCCGCTTTACA
GGCTTCGACGCCGCTTCGTTCTACCATCGACACCACCACGCTGGCACCCAGTTGATCGGCGCGAGAT
TTAATCGCCGCGACAATTTGCGACGGCGCGTGCAGGGCCAGACTGGAGGTGGCAACGCCAATCAGCA
ACGACTGTTTGCCCGCCAGTTGTTGTGCCACGCGGTTGGGAATGTAATTCAGCTCCGCCATCGCCGC
TTCCACTTTTTCCCGCGTTTTCGCAGAAACGTGGCTGGCCTGGTTCACCACGCGGGAAACGGTCTGA
TAAGAGACACCGGCATACTCTGCGACATCGTATAACGTTACTGGTTTCACATTCACCACCCTGAATT
GACTCTCTTCCGGGCGCTATCATGCCATACCGCGAAAGGTTTTGCGCCATTCGATGGTGTCCGGGAT
CTCGACGCTCTCCCTTATGCGACTCCTGCATTAGGAAGCAGCCCAGTAGTAGGTTGAGGCCGTTGAG
CACCGCCGCCGCAAGGAATGGTGCATGCAAGGAGATGGCGCCCAACAGTCCCCGGCCACGGGGCCT
GCCACCATACCCACGCCGAAACAAGCGCTCATGAGCCCGAAGTGGCGAGCCCGATCTTCCCCATCGG
TGATGTCGGCGATATAGGCGCCAGCAACCGCACCTGTGGCGCCGGTGATGCCGGCCACGATGCGTCC
GGCGTAGAGGATCGAGATCTCGATCCCGCGAAATTAATACGACTCACTATAGGGGAATTGTGAGCGG
ATAACAATTCCCCTCTAGAAATAATTTTGTTTAACTTTAAGAAGGAGATATACCATGGGAATCGAAG
AAGGTAAACTGGTAATCTGGATTAACGGCGATAAAGGCTATAACGGTCTCGCTGAAGTCGGTAAGAA
ATTCGAGAAAGATACCGGAATTAAAGTCACCGTTGAGCATCCGGATAAACTGGAAGAGAAATTCCCA
CAGGTTGCGGCAACTGGCGATGGCCCTGACATTATCTTCTGGGCACACGACCG
```

Figure 4 (Continue)

```
CTTTGGTGGCTACGCTCAATCTGGCCTGTTGGCTGAAATCACCCCGGACAAAGCGTTCCAGGACAAG
CTGTATCCGTTTACCTGGGATGCCGTACGTTACAACGGCAAGCTGATTGCTTACCCGATCGCTGTTG
AAGCGTTATCGCTGATTTATAACAAAGATCTGCTGCCGAACCCGCCAAAAACCTGGGAAGAGATCCC
GGCGCTGGATAAAGAACTGAAAGCGAAAGGTAAGAGCGCGCTGATGTTCAACCTGCAAGAACCGTAC
TTCACCTGGCCGCTGATTGCTGCTGACGGGGGTTATGCGTTCAAGTATGAAAACGGCAAGTACGACA
TTAAAGACGTGGGCGTGGATAACGCTGGCGCGAAAGCGGGTCTGACCTTCCTGGTTGACCTGATTAA
AAACAAACACATGAATGCAGACACCGATTACTCCATCGCAGAAGCTGCCTTTAATAAAGGCGAAACA
GCGATGACCATCAACGGCCCGTGGGCATGGTCCAACATCGACACCAGCAAAGTGAATTATGGTGTAA
CGGTACTGCCGACCTTCAAGGGTCAACCATCCAAACCGTTCGTTGGCGTGCTGAGCGCAGGTATTAA
CGCCGCCAGTCCGAACAAAGAGCTGGCAAAAGAGTTCCTCGAAAACTATCTGCTGACTGATGAAGGT
CTGGAAGCGGTTAATAAAGACAAACCGCTGGGTGCCGTAGCGCTGAAGTCTTACGAGGAAGAGTTGG
CGAAAGATCCACGTATTGCCGCCACAATGGAAAACGCCCAGAAAGGTGAAATCATGCCGAACATCCC
GCAGATGTCCGCTTTCTGGTATGCCGTGCGTACTGCGGTGATCAACGCCGCCAGCGGTCGTCAGACT
GTCGATGAAGCCCTGAAAGACGCGCAGACTAATTCGAGCTCGAACAACAACAACAATAACAATAACA
ACAACCTCGGGAGCAGCGGACTGGTTCCACGAGGATCCCATATGGCTAGCGCGCAGCTGCACTTCAT
GTACGTGGCGGCGGCCGCCTTTGTGCTTCTGTTCTTCGTGGGCTGCGGGGTGCTGCTGTCCCGCAAG
CGCCGGCGGCAGCATGGCCAGCTCTGGTTCCCTGAGGGCTTCAAAGTGTCTGAGGCCAGCAAGAAGA
AGCGGCGGGAGCCCCTCGGCGAGGACTCCGTGGGCCTCAAGCCCCTGAAGAACGCTTCAGACGGTGC
CCTCATGGACGACAACCAGAATGAGGAAGCTTGCTTGGGTGGCGGTCTGAACGACATCTTCGAGGCT
CAGAAAATCGAATGGCACGAATAACTCGAGCACCACCACCACCACTGAGATCCGGCTGCTAACA
AAGCCCGAAAGGAAGCTGAGTTGGCTGCTGCCACCGCTGAGCAATAACTAGCATAACCCCTTGGGGC
CTCTAAACGGGTCTTGAGGGGTTTTTTGCTGAAAGGAGGAACTATATCCGGAT
```

METHODS AND COMPOSITIONS FOR GAMMA-SECRETASE ASSAY

This application is the §371 U.S. National Stage of International Application No. PCT/US2011/050688, filed 7 Sep. 2011, which claims the benefit of U.S. Provisional Application Ser. No. 61/380,587, filed Sep. 7, 2010, each of which are incorporated by reference herein.

FIELD OF THE INVENTION

The present invention includes, but is not limited to, compositions and methods for measuring gamma-secretase ("γ-secretase") activity and assays for identifying modulators of γ-secretase activity. For instance, this disclosure describes newly designed substrates derived from the Notch cell surface receptor for use in high sensitivity assays for γ-secretase activity. In addition, the γ-secretase substrates identified herein are useful in assays to identify modulators of γ-secretase activity.

BACKGROUND OF THE INVENTION

γ-Secretase processes a variety of substrates including the amyloid precursor protein (APP) and Notch proteins. γ-Secretase cleaves APP to release Aβ peptides, which are widely considered to play a causative role in Alzheimer disease (AD).

The Notch signaling pathway is a highly conserved cell signaling system present in most multicellular organisms (Artavanis-Tsakonas et al., 1999, Science 284 (5415): 770-776). Notch protein family members are present in all metazoans, and mammals possess four different Notch receptors, referred to as NOTCH1, NOTCH2, NOTCH3, and NOTCH4. The Notch receptor is a single-pass transmembrane receptor protein. The ligands that bind Notch proteins and initiate signaling are bound to neighboring cells. Notch is a hetero-oligomer composed of a large extracellular portion, which associates in a calcium-dependent, non-covalent interaction with a smaller piece of the Notch protein composed of a short extracellular region, a single transmembrane-pass, and a small intracellular region (Brou et al., 2000, Mol. Cell. 5 (2): 207-16).

In addition to acting on APP, γ-secretase processes Notch and other type I membrane proteins. Notch is also cleaved by multiple proteases. Notch signaling is controlled by ligand binding, which exposes a negative control region that is susceptible to proteolytic cleavage of the receptor. The GenBank Accession Number for human Notch1 cDNA is AF'308602.1, and for the corresponding polypeptide gene product it is AAG33848.1. Human Notch1 has 2556 amino acid residues. In processing Notch1, first, a membrane-proximal cleavage is executed at site S2 (between residues Ala1710 and Val1711 (see Supplementary Figure S1A of van Tetering et al., 2009, J. Biol. Chem., 284:31018-31027) by an ADAM (A Disintegrin And Metalloprotease) metalloprotease, removing the extracellular domain to generate the membrane-anchored Notch extracellular truncation fragment (NEXT). (The ADAM family includes proteins containing disintegrin-like and metalloprotease-like domains. ADAMs are involved in diverse cellular processes such as development, cell-cell interactions and protein ectodomain.) NEXT is subsequently cleaved by γ-secretase at site S3 (see Supplementary Figure S1A of van Tetering et al., 2009, J. Biol. Chem., 284:31018-31027) to generate Notch Intracellular Domain (NICD) which translocates into the nucleus where it modulates expression of target genes that are involved in cell fate decisions during embryogenesis, hematopoeisis, and stem cell differentiation (Chan et al., 1998, Cell, 94, 423-426, Berezovska et al., 1999, Brain Res Mol Brain Res., 69:273-280, and Redmond et al., 2000, Nat. Neurosci., 3:30-40).

γ-Secretase is a membrane-bound aspartyl protease consisting of at least four subunits, which are Presenilin (PS, either PS1 or PS2), Aph-1, Nicastrin (Nct) and Pen-2. PS is believed to be the catalytic subunit of γ-secretase and mutations in PS1 and PS2 have been linked to Familial Alzheimer's Disease (FAD) (Sherrington et al., 1995, Nature, 375:754-760, Levy Lahad et al., 1995, Science, 269:973-977). Although the precise pathological mechanism of these FAD mutations is unknown, it has been postulated that they alter the specificity of γ-secretase and lead to an increase in the ratio of Aβ42 to Aβ40 peptide (Borchelt et al., 1996, Neuron, 17:1005-1013, Duff et al., 1996, Nature, 383:710-713, and Bentahir et al., 2006, J. Neurochem., 96:732-742) Aβ42 is more prone to form insoluble aggregates than is Aβ40, so that FAD mutations are deleterious. In addition, FAD mutations also reduce γ-secretase activity for Notch and E-cadherin processing (Song et al., 1999, Proc. Nat. Acad. Sci. USA, 96:6959-6963, Marambaud et al., 2002, EMBO J., 21:1948-1956, and Marambaud et al., 2003, Cell, 114:635-645). Several studies have shown that FAD mutations of PS1 affect Notch cleavage (Bentahir et al., 2006, J. Neurochem., 96:732-742), Song et al., 1999, Proc. Nat. Acad. Sci. USA, 96:6959-6963, Nakajima et al., 2000, J Neurosci Res., 62:311-317, Amtul et al., 2002, Neurobiol Dis., 9:269-273, Chen et al., 2002, J. Biol. Chem., 277: 36521-36526).

It is presently unclear whether the differential cellular effects of PS1 mutations on Notch1 cleavage are attributed to cellular factors such as the maturation of the γ-secretase complex, trafficking of substrates or modulation of γ-secretase itself. Although a cell-free Notch/γ-secretase assay has been reported using N100Flag substrate (Moehlmann et al., 2002, Proc. Nat. Acad. Sci. USA, 99:8025-8030), it is a western analysis-based assay that is limited in its application for the characterization of γ-secretase since it is labor-intensive, has low throughput and is not quantitative. Moreover, it has been questioned whether N100Flag is processed by γ-secretase (Keller et al., 2006, Biochem., 45:5351-5358).

SUMMARY OF THE INVENTION

There is a need to determine whether PS1 mutations might directly affect the catalytic activity of γ-secretase. In order to monitor γ-secretase activity for Notch1 cleavage and develop Notch specific γ-secretase inhibitors, there is a need for a robust, specific and sensitive in vitro γ-secretase assay using a substrate based on a Notch protein, such as Notch1. There is clearly a need for reliable Notch-based substrate that is susceptible to facile proteolysis by γ-secretase. There is a need to develop an assay that specifically determines the occurrence and amount of the product of proteolysis of Notch by γ-secretase with high sensitivity. In addition there remains a need to develop an assay of γ-secretase activity on Notch in real time. There remains in addition a need for an efficient assay that can screen candidate compounds for their ability to modulate the activity of PS1 on Notch proteins. The instant disclosure presents a quick and easy in vitro assay of the γ-secretase catalyzed cleavage of Notch1. This novel in vitro γ-secretase assay that detects γ-secretase cleaved Notch1 product will be a valuable means for better characterization of γ-secretase and for identification of modulators of the activity of γ-secretase on Notch receptor family members.

In a first aspect this disclosure presents a reagent that specifically binds a product of the cleavage of a Notch receptor protein that is catalyzed by a γ-secretase at the S3 site. In many embodiments the reagent does not bind a Notch receptor protein that has not been cleaved by a γ-secretase. In additional embodiments the reagent includes an antibody. In further embodiments the antibody is a polyclonal antibody. In additional embodiments the antibody is a monoclonal antibody. In further embodiments the antibody is a single chain antibody. In further embodiments the antibody specifically binds VLLSRKRRR (SEQ ID NO:2). In still further embodiments the antibody is elicited by immunizing a host animal with a composition including a peptide containing the sequence VLLSRKRRR (SEQ ID NO:2). Optionally, the sequence VLLSRKRRR (SEQ ID NO:2) may further include a cysteine residue at the carboxy terminal end.

In a second aspect this disclosure presents a substrate peptide including at least a portion of a Notch protein wherein the substrate bears a first label, and wherein the amino acid sequence of the substrate is cleavable by the activity of γ-secretase to provide a detectable product peptide that includes the first label. In certain embodiments the substrate peptide includes a Notch substrate, such as, but not limited to, amino acid residues 1733-1812 of human Notch1 protein, which includes a first scissile peptide bond cleavable by γ-secretase. In many embodiments the first scissile peptide bond is the S3 site. In some embodiments the substrate peptide further includes a tag linked to the labeled Notch amino acid sequence or portion thereof wherein the tag specifically binds a target with high affinity; in many embodiments the target is a polysaccharide containing maltose. In still further embodiments the tag is linked to the substrate peptide via a linking amino acid sequence that includes a second scissile peptide bond, wherein the linking amino acid sequence constitutes a target for a specific protease whose action results in removal of the tag from the substrate peptide. In certain embodiments the specific protease is thrombin. In still further embodiments the first label contains a labeling amino acid sequence reactable to attach a first member of a specific binding pair to the labeling amino acid sequence. In still additional embodiments the first member of the specific binding pair includes biotin. (See FIGS. 1A and 5A).

In particular embodiments the substrate peptide includes, in order from the N-terminus to the C-terminus, a tag that specifically binds a polysaccharide containing maltose, e.g., maltose binding protein, a thrombin target sequence, a Notch1 sequence that includes the first scissile bond corresponding to the S3 site of Notch1 protein, and a labeling amino acid sequence reactable to bind biotin; in certain embodiments the label includes biotin so incorporated. In still a further particular embodiment the substrate peptide includes, in order from the N-terminus to the C-terminus, a labeling amino acid sequence reactable to bind biotin, a Notch1 sequence that includes the first scissile bond, a thrombin target sequence, and the tag that specifically binds a polysaccharide containing maltose.

In still a further aspect, this disclosure presents a polynucleotide susceptible of expression of a substrate peptide described in the preceding two paragraphs, when incorporated in a suitable host cell and incubated under appropriate culture conditions.

In yet a further aspect, this disclosure includes a method of synthesizing a peptide substrate wherein the polynucleotide described in the preceding paragraph is introduced into a suitable host cell, the host cell is incubated under appropriate culture conditions for a time sufficient to express the peptide substrate, and the peptide substrate is isolated from the cultured cells. In a further aspect, this disclosure presents polypeptides that include a gamma-secretase cleavage site, and is cleaved by a gamma-secretase under suitable conditions. Such polypeptides include a truncated Notch polypeptide that has fewer amino acids than a full length natural Notch cell surface receptor. Such a polypeptide may be referred to herein as a Notch substrate.

In a further aspect this disclosure presents a high sensitivity method of assaying the activity of γ-secretase that includes the steps of:
  a) providing composition suspected of containing γ-secretase activity;
  b) contacting the composition with a polypeptide substrate for γ-secretase including at least a portion of a Notch protein bound to a detectable label, wherein cleavage of the labeled substrate by γ-secretase provides a detectably labeled product;
  c) contacting the labeled product with
    1) a first ligand bearing a first tag wherein the first ligand specifically binds the label, and
    2) a second ligand bearing a second tag wherein the second ligand specifically binds the product; and
  d) determining the presence and/or the amount of the labeled product bound to the first ligand and to the second ligand.

In certain embodiments of the method the peptide substrate includes amino acid residues 1733-1812 of human Notch1. In additional embodiments of the assay the detectable label includes biotin. In additional embodiments the first ligand includes an avidin and the first tag contains a detectable first fluorophore, and in further embodiments the second ligand includes a first antibody that a) specifically binds a newly generated chain terminus of the product and that b) is bound to a second antibody bearing a second fluorophore such that fluorescence resonance energy transfer occurs between the first fluorophore and the second fluorophore. In alternative embodiments the first ligand includes an avidin and a photosensitizer that converts triplet oxygen to singlet oxygen, and the second ligand includes a) a first antibody that specifically binds a newly generated chain terminus of the product, b) a second antibody that binds the first antibody, and c) a luminescence emitter excited by a singlet oxygen-dependent chemiluminescence reaction.

In an additional aspect the disclosure presents a high throughput method of assaying the activity of γ-secretase that includes the steps of:
  a) providing a plurality of containers, each container containing a composition suspected of containing γ-secretase activity;
  b) adding to each container a polypeptide substrate for γ-secretase including at least a portion of a Notch protein bound to a detectable label, wherein cleavage of the labeled substrate by γ-secretase provides a detectably labeled product to each container;
  c) contacting the labeled product with
    1) a first ligand bearing a first tag wherein the first ligand specifically binds the label, and
    2) a second ligand bearing a second tag wherein the second ligand specifically binds the product; and
  d) determining the presence and/or the amount of the labeled product bound to the first ligand and to the second ligand.

In various embodiments of this method each container is a well in a multi-well assay plate. In various additional embodiments, a plate contains at least 96 wells, or at least 384 wells, or at least 1536 wells. In certain embodiments of the method the peptide substrate includes amino acid residues 1733-1812 of human Notch1. In additional embodiments of the assay the detectable label includes biotin. In additional embodiments the first ligand includes an avidin and the first tag contains a detectable first fluorophore, and in further embodiments the second ligand includes a first antibody that a) specifically binds a newly generated chain terminus of the product and that b) is bound to a second antibody bearing a second fluorophore such that fluorescence resonance energy transfer occurs between the first fluorophore and the second fluorophore. In alternative embodiments the first ligand includes an avidin and a photosensitizer that converts triplet oxygen to singlet oxygen, and the second ligand includes a) a first antibody that specifically binds a newly generated chain terminus of the product, b) a second antibody that binds the first antibody, and c) a luminescence emitter excited by a singlet oxygen-dependent chemiluminescence reaction.

In an additional aspect a method is disclosed of assaying the activity of γ-secretase in a cell that includes the steps of
  a) providing a cell suspected of containing γ-secretase activity;
  b) adding media containing a polypeptide substrate for γ-secretase including at least a portion of a Notch protein bound to a detectable label, wherein cleavage of the labeled substrate by γ-secretase provides a labeled product; and
  c) determining the presence of labeled product.
In certain embodiments, the determining includes
  c) separating the cells after a suitable incubation period to provide a supernatant; and
  d) assaying the supernatant for the labeled product.
In certain embodiments assaying the supernatant is carried out by SDS-PAGE and subsequent immunoblotting with an antibody that specifically binds a newly generated chain terminus of the product to identify the presence of the product. In alternative embodiments the determining includes fixing the cell and conducting immunohistochemical identification of the product in the intact cell with an antibody that specifically binds a newly generated chain terminus of the product. In this method the media may further include a detergent. Additionally, in many embodiments the label includes biotin. In still other embodiments assaying for the labeled product includes assaying for a detectable complex containing the product and one or more detectable probes, for example the complex includes a first specific binding member that contains a first detectable probe, wherein the first specific binding member specifically binds the product to form a binary complex. In specific embodiments the first probe includes ruthenium such that the detection is conducted using electrochemiluminescence. In additional embodiments of the assaying further includes
  c) separating the cells after a suitable incubation period to provide a supernatant;
  d) contacting the labeled product with
    1) a first ligand bearing a first tag wherein the first ligand specifically binds the label, and
    2) a second ligand bearing a second tag wherein the second ligand specifically binds the product; and
  e) determining the presence and/or the amount of the labeled product bound to the first ligand and to the second ligand.

In the latter embodiments, the first ligand includes an avidin and the first tag contains a detectable first fluorophore, and in further embodiments the second ligand includes a first antibody that a) specifically binds a newly generated chain terminus of the product and that b) is bound to a second antibody bearing a second fluorophore such that fluorescence resonance energy transfer occurs between the first fluorophore and the second fluorophore. In still further alternative embodiments the first ligand includes an avidin and a photosensitizer that converts triplet oxygen to singlet oxygen, and the second ligand includes a) a first antibody that specifically binds a newly generated chain terminus of the product, b) a second antibody that binds the first antibody, and c) a luminescence emitter excited by a singlet oxygen-dependent chemiluminescence reaction.

In an additional aspect this disclosure presents a method of screening for a modulator of γ-secretase activity including the steps of:
  a) providing a container containing a composition that includes γ-secretase activity;
  b) contacting the composition with a mixture including a candidate compound and a polypeptide substrate for γ-secretase including at least a portion of a Notch protein bound to a detectable label, wherein cleavage of the labeled substrate by γ-secretase provides a labeled product that is detectable; and
  c) determining whether the candidate compound modulates formation of the labeled product of the γ-secretase-catalyzed cleavage of the substrate.
In certain embodiments of the method the peptide substrate includes amino acid residues 1733-1812 of human Notch1. In many embodiments of the method the label includes biotin. In other embodiments the determining the formation of the labeled product includes assaying for a detectable complex including the product and one or more detectable probes. In certain embodiments the complex contains a first specific binding member that includes a first detectable probe, wherein the first specific binding member specifically binds the product to form a binary complex, and in certain embodiments the first probe includes ruthenium such that the detection is conducted using electrochemiluminescence.

In additional embodiments of the method the determining further includes
  d) contacting the labeled product with
    1) a first ligand bearing a first tag wherein the first ligand specifically binds the label, and
    2) a second ligand bearing a second tag wherein the second ligand specifically binds the product; and
  e) determining the presence and/or the amount of the labeled product bound to the first ligand and to the second ligand.
In certain embodiments of this variation the first ligand includes an avidin and the first tag contains a detectable first fluorophore, and in further embodiments the second ligand includes a first antibody that a) specifically binds a newly generated chain terminus of the product and that b) is bound to a second antibody bearing a second fluorophore such that fluorescence resonance energy transfer occurs between the first fluorophore and the second fluorophore. In alternative embodiments the first ligand includes an avidin and a photosensitizer that converts triplet oxygen to singlet oxygen, and the second ligand includes a) a first antibody that specifically binds a newly generated chain terminus of the product, b) a second antibody that binds the first antibody, and c) a luminescence emitter excited by a singlet oxygen-dependent chemiluminescence reaction.

In an additional aspect the disclosure provides a high throughput method of screening for a modulator of γ-secretase activity including the steps of
  a) providing a plurality of containers, each container containing a composition containing γ-secretase activity;
  b) adding to each container a composition including a candidate compound and a polypeptide substrate for γ-secretase including at least a portion of a Notch protein bound to a detectable label, wherein cleavage of the labeled substrate by γ-secretase provides a labeled product that is detectable with high sensitivity; and
  c) determining whether the candidate compound modulates formation of the labeled product of the γ-secretase-catalyzed cleavage of the substrate.

In various embodiments of this screening method each container is a well in a multi-well assay plate; and in particular embodiments of the screen a plate contains at least 96 wells, or at least 384 wells or at least 1536 wells.

In certain embodiments of the method the peptide substrate includes amino acid residues 1733-1812 of human Notch1. In many embodiments of the method the label includes biotin. In other embodiments the determining the formation of the labeled product includes assaying for a detectable complex including the product and one or more detectable probes. In certain embodiments the complex contains a first specific binding member that includes a first detectable probe, wherein the first specific binding member specifically binds the product to form a binary complex, and in certain embodiments the first probe includes ruthenium such that the detection is conducted using electrochemiluminescence.

In additional embodiments of the high throughput method of screening the determining further includes
  c) contacting the labeled product with
    1) a first ligand bearing a first tag wherein the first ligand specifically binds the label, and
    2) a second ligand bearing a second tag wherein the second ligand specifically binds the product; and
  d) determining whether the candidate compound modulates the presence and/or the amount of the labeled product bound to the first ligand and to the second ligand.

In certain embodiments of this variation the first ligand includes an avidin and the first tag contains a detectable first fluorophore, and in further embodiments the second ligand includes a first antibody that a) specifically binds a newly generated chain terminus of the product and that b) is bound to a second antibody bearing a second fluorophore such that fluorescence resonance energy transfer occurs between the first fluorophore and the second fluorophore. In alternative embodiments the first ligand includes an avidin and a photosensitizer that converts triplet oxygen to singlet oxygen, and the second ligand includes a) a first antibody that specifically binds a newly generated chain terminus of the product, b) a second antibody that binds the first antibody, and c) a luminescence emitter excited by a singlet oxygen-dependent chemiluminescence reaction.

Still a further aspect presented in this disclosure is a method of screening for a modulator of γ-secretase activity in a cell including the steps of
  a) providing a container that contains a cell containing γ-secretase activity;
  b) adding to the container media containing a candidate compound and a polypeptide substrate for γ-secretase including at least a portion of a Notch protein bound to a detectable label, wherein cleavage of the labeled substrate by γ-secretase provides a labeled product that is detectable with high sensitivity; and
  c) determining whether the candidate compound modulates formation of the labeled product.

In certain embodiments, the determining includes
  c) separating the cells after a suitable incubation period to provide a supernatant; and
  d) assaying the supernatant to determine whether the candidate compound modulates formation of the labeled product.

In certain embodiments assaying the supernatant is carried out by SDS-PAGE and subsequent immunoblotting with an antibody that specifically binds a newly generated chain terminus of the product to identify the presence of the product. In alternative embodiments the determining includes fixing the cell and conducting immunohistochemical identification of the product in the intact cell with an antibody that specifically binds a newly generated chain terminus of the product. In this method the media may further include a detergent. In certain embodiments of the method the peptide substrate includes amino acid residues 1733-1812 of human Notch1. Additionally, in many embodiments the label includes biotin. In still other embodiments assaying for the labeled product includes assaying for a detectable complex containing the product and one or more detectable probes, for example the complex includes a first specific binding member that contains a first detectable probe, wherein the first specific binding member specifically binds the product to form a binary complex. In specific embodiments the first probe includes ruthenium such that the detection is conducted using electrochemiluminescence.

In additional embodiments of the assaying further includes
  c) separating the cells after a suitable incubation period to provide a supernatant;
  d) contacting the labeled product with
    1) a first ligand bearing a first tag wherein the first ligand specifically binds the label, and
    2) a second ligand bearing a second tag wherein the second ligand specifically binds the product; and
  e) determining whether the candidate compound modulates the presence and/or the amount of the labeled product bound to the first ligand and to the second ligand.

In the latter embodiments, the first ligand includes an avidin and the first tag contains a detectable first fluorophore, and in further embodiments the second ligand includes a first antibody that a) specifically binds a newly generated chain terminus of the product and that b) is bound to a second antibody bearing a second fluorophore such that fluorescence resonance energy transfer occurs between the first fluorophore and the second fluorophore. In still further alternative embodiments the first ligand includes an avidin and a photosensitizer that converts triplet oxygen to singlet oxygen, and the second ligand includes a) a first antibody that specifically binds a newly generated chain terminus of the product, b) a second antibody that binds the first antibody, and c) a luminescence emitter excited by a singlet oxygen-dependent chemiluminescence reaction.

In still an additional aspect the disclosure presents a high throughput method of screening for a modulator of γ-secretase activity in a cell that includes the steps of:
  a) providing a plurality of containers, each container containing a cell containing γ-secretase activity;
  b) to each container adding media including a candidate compound and a polypeptide substrate for γ-secretase including at least a portion of a Notch protein bound to a detectable label, wherein cleavage of the labeled substrate by γ-secretase provides a labeled product that is detectable with high sensitivity; and c) determining in each container whether the candidate compound modulates formation of the labeled product of the γ-secretase-catalyzed cleavage of the substrate. In various embodiments of this screening method each container is a well in a multi-well assay plate; in certain embodiments a plate contains at least 96 wells, or at least 384 wells, or at least 1536 wells.

BRIEF DESCRIPTION OF THE DRAWING

FIG. 4. Plasmid sequence (SEQ ID NO:5) of pIAD16 with N1-Sb1 insert.

DETAILED DESCRIPTION OF THE INVENTION

Figure 1:
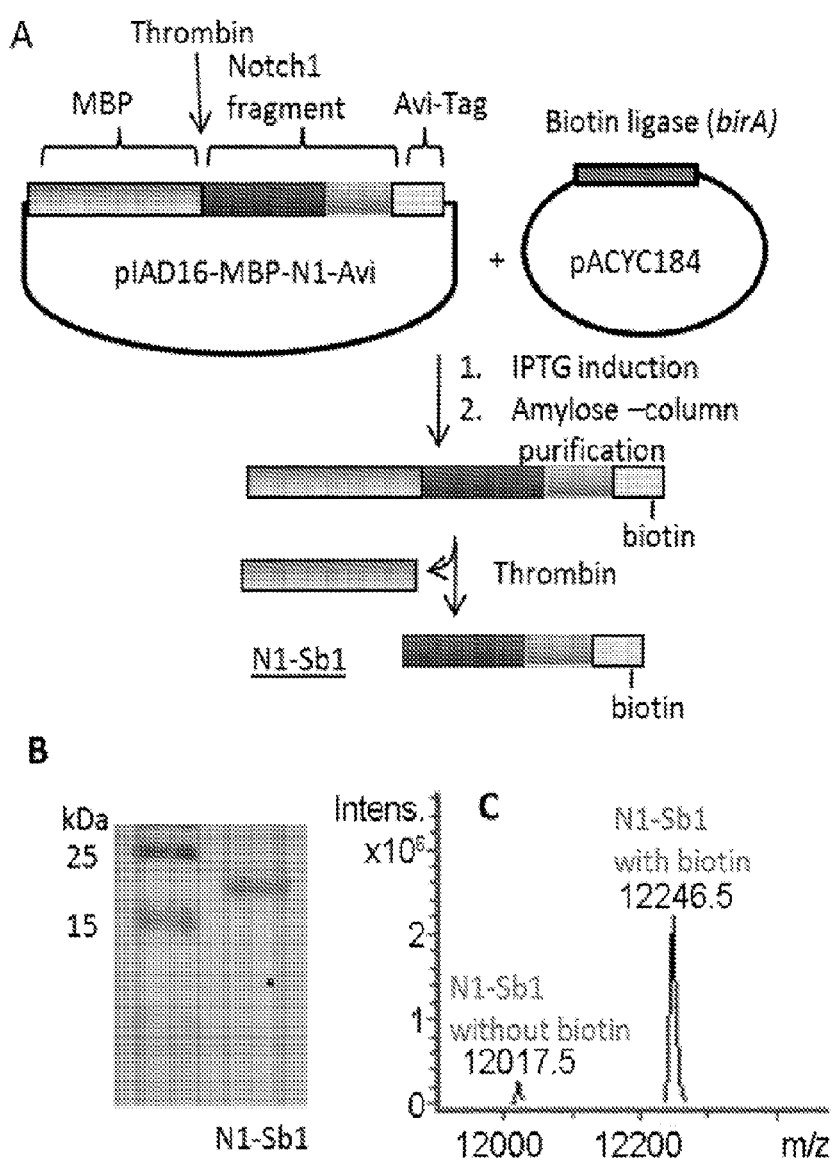
FIG. 1 Production of biotinylated recombinant N1-Sb1 substrate using plasmid pIAD16-MBP-N-1-Avi. A) Schematic representation of protein expression and purification. B) Coomassie staining of the product. C) LC-MS analysis of the purified product.

As used herein, the term "Notch protein," and related terms and phrases, relate generally to any member of the Notch family of cell surface receptors present in metazoa. Mammals possess four different Notch receptors, referred to as NOTCH1, NOTCH2, NOTCH3, and NOTCH4. An example of an amino acid sequence of human Notch1 is disclosed in GenBank Acc. No. AAG33848.1 (GI: 11275980), and is reproduced below in Table 1.

TABLE 1

(SEQ ID NO: 1).

1 mpplaplc lallpalaar gprcsqpget clnggkceaa ngteacvcgg afvgprcqdp 61 npclstpckn agtchvvdrr gvadyacsca lgfsgplclt pldnacltnp crnggtcdll TABLE 1 -continued (SEQ ID NO: 1).

```
 121  tlteykcrcp  pgwsgkscqq  adpcasnpca  nggqclpfea  syichcppsf  hgptcrqdvn
 181  ecgqkprlcr  hggtchnevg  syrcvcrath  tgpncerpyv  pcspspcqng  gtcrptgdvt
 241  hecaclpgft  gqnceenidd  cpgnnckngg  acvdgvntyn  cpcppewtgq  yctedvdecq
 301  lmpnacqngg  tchnthggyn  cvcvngwtge  dcseniddca  saacfhgatc  hdrvasfyce
 361  cphgrtgllc  hlndacisnp  cnegsncdtn  pvngkaictc  psgytgpacs  qdvdecslga
 421  npcehagkci  ntlgsfecqc  lqgytgprce  idvnecvsnp  cqndatcldq  igefqcmcmp
 481  gyegvhcevn  tdecasspcl  hngrcldkin  efqcecptgf  tghlcqydvd  ecastpckng
 541  akcldgpnty  tcvctegytg  thcevdidec  dpdpchygsc  kdgvatftcl  crpgytghhc
 601  etninecssq  pcrlrgtcqd  pdnaylcfcl  kgttgpncei  nlddcasspc  dsgtcldkid
 661  gyecacepgy  tgsmcnsnid  ecagnpchng  gtcedgingf  tcrcpegyhd  ptclsevnec
 721  nsnpcvhgac  rdslngykcd  cdpgwsgtnc  dinnnecesn  pcvnggtckd  mtsgivctcr
 781  egfsgpncqt  ninecasnpc  lnkgtciddv  agykcncllp  ytgatcevvl  apcapspcrn
 841  ggecrqsedy  esfscvcpta  gakggtcevd  inecvlspcr  hgascqnthg  xyrchcqagy
 901  sgrncetdid  dcrpnpchng  gsctdginta  fcdclpgfrg  tfceedinec  asdpcrngan
 961  ctdcvdsytc  tcpagfsgih  cenntpdcte  sscfnggtcv  dginsftclc  ppgftgsycq
1021  hvvnecdsrp  cllggtcqdg  rglhrctcpq  gytgpncqnl  vhwcdsspck  nggkcwqtht
1081  qyrcecpsgw  tglycdvpsv  scevaaqrqg  vdvarlcqhg  glcvdagnth  hcrcqagytg
1141  sycedlvdec  spspcqngat  ctdylggysc  kcvagyhgvn  cseeidecls  hpcqnggtcl
1201  dlpntykcsc  prgtqgvhce  invddcnppv  dpvsrspkcf  nngtcvdqvg  gysctcppgf
1261  vgercegdvn  eclsnpcdar  gtqncvqrvn  dfhcecragh  tgrrcesvin  gckgkpckng
1321  gtcavasnta  rgfickcpag  fegatcenda  rtcgslrcln  ggtcisgprs  ptclclgpft
1381  gpecqfpass  pclggnpcyn  qgtceptses  pfyrclcpak  fngllchild  ysfgggagrd
1441  ippplieeac  elpecqedag  nkvcslqcnn  hacgwdggdc  slnfndpwkn  ctqslqcwky
1501  fsdghcdsqc  nsagclfdgf  dcgraeggcn  plydqyckdh  fsdghcdqgc  nsaecewdgl
1561  dcaehvperl  aagtlvvvvl  mppeqlrnss  fhflrelsrv  lhtnvvfkrd  ahgqqmifpy
1621  ygreeelrkh  pikraaegwa  apdallgqvk  aslIpggseg  grrrreldpm  dvrgsivyle
1681  idnrqcvgas  sqcfqsatdv  aaflgalasl  gslnipykie  avqsetvepp  ppaqlhfmyv
1741  aaaafvllff  vgcgvllsrk  rrrqhgqlwf  pegfkvseas  kkkrreplge  dsvglkplkn
1801  asdgalmddn  qnewgdedle  tkkfrfeepv  vlpdlddqtd  hrqwtqqhld  aadlrmsama
1861  ptppqgevda  dcmdvnvrgp  dgftplmias  csgggletgn  seeeedapav  isdfiyqgas
1921  lhnqtdrtge  talhlaarys  rsdaakrlle  asadaniqdn  mgrtplhaav  sadaqgvfqi
1981  lirnratdld  armhdgttpl  ilaarlaveg  mledlinsha  dvnavddlgk  salhwaaavn
2041  nvdaavvllk  ngankdmqnn  reetplflaa  regsyetakv  lldhfanrdi  tdhmdrlprd
2101  iagermhhdi  vrlldeynlv  rspqlhgapl  ggtptlsppl  cspngylgsl  kpgvqgkkvr
2161  kpsskglacg  skeakdlkar  rkksqdgkgc  lldssgmlsp  vdslesphgy  lsdvasppll
2221  pspfqqspsv  plnhlpgmpd  thlgighlnv  aakpemaalg  gggrlafetg  pprlshlpva
2281  sgtstvlgss  sggalnftvg  gstslngqce  wlsrlqsgmv  pnqynplrgs  vapgplstqa
2341  pslqhgmvgp  lhsslaasal  sqmmsyqglp  strlatqphl  vqtqqvqpqn  lqmqqqnlqp
2401  aniqqqqslq  pppppppqphl  gvssaasghl  grsflsgeps  qadvqplgps  slavhtilpq
```

TABLE 1 -continued (SEQ ID NO: 1).

2461 espalptslp sslvppvtaa qfltppsqhs ysspvdntps hqlqvpehpf ltpspespdq 2521 wssssphsnv sdwsegvssp ptsmqsqiar ipeafk As used herein the terms "peptide" and "polypeptide" and related terms designate any and all compositions in which a given amino acid residue is linked to a neighboring amino acid residue via a peptide bond. As used herein the term "peptide" is synonymous with "polypeptide". In this usage the length of the polypeptide is not limited to a specified minimum number of amino acid residues. A polypeptide may be composed of only naturally occurring amino acid residues, or it may include modified, synthetic, or derivatized amino acid residues as well.

As used herein, the term "gamma-secretase" or "γ-secretase" refers to any in vivo, ex vivo or in vitro substance containing gamma-secretase activity. Thus, by way of non-limiting example, γ-secretase may be obtained from, or be found in, a live organism (including a human, or a laboratory or veterinary animal such as a mouse, rat, or primate) or a sample therefrom (such as a tissue or body fluid, or extract thereof), a cell (such as a primary cell or cell line, or extract thereof), extracellular medium or matrix or milieu, or isolated protein. Sources of γ-secretase are not limited to naturally occurring gamma-secretase, but may also include engineered and/or synthesized gamma-secretase. A gamma-secretase refers to an enzyme(s) with the ability to cleave at the gamma-secretase site of a gamma-secretase substrate known to have a gamma-secretase cleavage site, e.g., a Notch protein and other gamma-secretase substrates described herein, such as a Notch substrate. As used herein, gamma-secretase includes all recombinant forms, mutations, and other variants of gamma-secretase so long as these maintain a functional capability to catalyze the cleavage of molecules or substrates bearing gamma-secretase cleavage sites. In one embodiment, such a gamma-secretase cleavage site is an S3 site. The identity of Notch S3 cleavage sites are known in the art.

As used herein, the term "gamma-secretase substrate" refers to any naturally occurring or synthetic sequence of amino acids (e.g., polypeptides and proteins) including a gamma-secretase cleavage site. Gamma-secretase substrates are know in the art, and non-limiting examples of gamma-secretase substrates include Notch proteins, APP, neuregulin-1, alpha-protocadherin, SCNB2, Tie-1, beta-APP like protein 1, beta-APP like protein 2, nectin-3, nectin-4, alcadein alpha, alcadein gamma, APLP1, APLP2, ApoER2, CD43, CD44, CSF1R, CXCL16, CX3CL1, DCC, Deltal, E-cadherin, EphrinB1, EphrinB2, EphB2, ErbB4, GHR, HLA-A2, IGF1R, IFN-alpha-R2, IL-1R2, IR, IRE1-alpha, Jagged2, L1, LRP, LPR1B, LRP2, LRP6, N-cadherin, Nectin1-alpha, notch, Notch1, Notch2, Notch3, Notch4, NRADD, p75-NTR, PKHD1, Pcdh-alpha-4, Pcdh-gamma-C3, PTP-kappa, PTP-g, PTP-LAR, S or CS1b, SorLA, Sortilin, Syndecan3, Tyrosinase, TYRP1, TYRP2, VEGF-R1, VGSC-beta-2, and VLDLR.

Another gamma-secretase substrate is a Notch substrate. As used herein, the term "Notch substrate" refers to any Notch polypeptide that has fewer amino acids than a full length natural Notch cell surface receptor, includes a gamma-secretase cleavage site, and is cleaved by a gamma-secretase under suitable conditions. In some embodiments, the Notch substrate is cleaved at an S3 site. In some embodiments, a Notch substrate further includes at least one amino acid modification. Such a modification may include at least one amino acid substitution, deletion, insertion, or addition. Examples of Notch substrates are shown in Table 2.

TABLE 2

| Notch1 Peptide Substrate | Amino Acid Residues of Notch1 (SEQ ID NO: 1) |
| --- | --- |
| N1Sb1 (NTM2) | 1732-1812 (SEQ ID NO: 6) |
| N1Sb2 (NTM1) | 1732-1770 (SEQ ID NO: 7) |
| N1Sb3 | 1720-1812 (SEQ ID NO: 9) |
| N1Sb4 | 1708-1812 (SEQ ID NO: 10) |
| N1Sb5 | 1665-1812 (SEQ ID NO: 11) |
| N1Sb6 | 1696-1812 (SEQ ID NO: 12) |
| N1Sb7 | 1726-1812 (SEQ ID NO: 13) |

Other Notch substrates include fragments of Notch substrates disclosed in Table 2. A fragment includes a gamma-secreates cleavage site and can be cleaved by a gamma-secretase under suitable conditions. a fragment may include a deletion of amino acids at the N-terminal end, the C-terminal end, or both. The total number of amino acids deleted may be at least 1, at least 2, at least 3, at least 4, at least 5, at least 6, at least 10, at least 12, at least 20, at least 30, at least 40, at least 42, and so on. The total number of amino acids may be deleted from the N-terminal end, the C-terminal end, or the combination of both.

Other examples of Notch substrates include amino acid sequence having structural similarity to a reference Notch substrate or fragment thereof. For example, polypeptides having structural similarity to a reference Notch substrate include naturally-occurring allelic variants of a Notch sequence that may exist in the population. A Notch substrate that is structurally similar to the amino acid sequence of a polypeptide described herein has a gamma-secretase cleavage site, and is cleaved by a gamma-secretase under suitable conditions. In one embodiment, a gamma-secretase cleavage site is an S2 cleavage site, and in another embodiment a gamma-secretase cleavage site is an S3 cleavage site. Methods for testing whether a polypeptide is cleaved by a gamma-secretase under suitable conditions are described below.

Structural similarity of two polypeptides can be determined by aligning the residues of the two polypeptides (for example, a candidate polypeptide and any appropriate reference polypeptide described herein, such as amino acids 1732-1812 of SEQ ID NO:1 or a fragment thereof) to optimize the number of identical amino acids along the lengths of their sequences; gaps in either or both sequences are permitted in making the alignment in order to optimize the number of identical amino acids, although the amino acids in each sequence must nonetheless remain in their proper order. A reference polypeptide may be a polypeptide described herein. A candidate polypeptide is the polypeptide being compared to the reference polypeptide. A candidate polypeptide may be isolated, for example, from a cell, or can be produced using recombinant techniques, or chemically or enzymatically synthesized.

Unless modified as otherwise described herein, a pairwise comparison analysis of amino acid sequences can be carried out using parameters for polypeptide sequence comparison include the algorithm of Needleman and Wunsch (1970, J. Mol. Biol. 48: 443-453), the comparison matrix BLOSSUM62 from Hentikoff and Hentikoff (1992, Proc. Natl. Acad. Sci. USA, 89:10915-10919), with gap penalty 12 and gap length penalty 4. A program useful with these parameters is publicly available as the "gap" program from Genetics Computer Group, Madison Wis. The aforementioned parameters are the default parameters for peptide comparisons (along with no penalty for end gaps).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a polypeptide described herein may be selected from other members of the class to which the amino acid belongs. For example, it is known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2.

Thus, as used herein, a candidate polypeptide useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence or fragment thereof.

Alternatively, as used herein, a candidate polypeptide useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence or fragment thereof.

Also included in the present invention are polynucleotides encoding the polypeptides disclosed herein. As used herein, the term "polynucleotide" refers to a polymeric form of nucleotides of any length, either ribonucleotides, deoxynucleotides, peptide nucleic acids, or a combination thereof, and includes both single-stranded molecules and double-stranded duplexes. A polynucleotide can be obtained directly from a natural source, or can be prepared with the aid of recombinant, enzymatic, or chemical techniques. An example of a polynucleotides encoding SEQ ID NO:1 (a Notch1 polypeptide) is GenBank Accession Number AF308602.1, and the skilled person can readily identify portions of the polynucleotide that encode the Notch substrates disclosed in Table 2. It should be understood that a polynucleotide encoding one of the Notch substrates disclosed in Table 2 is not limited to the appropriate portion of the nucleotide sequence disclosed GenBank Accession Number AF308602.1, but also includes the class of polynucleotides encoding a Notch substrate as a result of the degeneracy of the genetic code. For example, the naturally occurring nucleotide sequence disclosed GenBank Accession Number AF308602.1 is but one member of the class of nucleotide sequences encoding a Notch1 polypeptide having the amino acid sequence SEQ ID NO:1. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid.

As used herein, the term "isolated," as it refers to a polypeptide refers to any polypeptide that has been removed or separated from any source, e.g., from a cell that naturally expresses the protein, polypeptide or fragment thereof or that has been engineered to express the protein, polypeptide or fragment thereof. Polypeptides that are produced by recombinant, enzymatic, or chemical techniques are considered to be isolated and purified by definition, since they were never present in a natural environment.

The term "contacting" refers to bringing into association, either directly or indirectly, two or more substances or compositions. Contacting may occur in vivo, ex vivo or in vitro. Commonly contacting a first composition with a second composition brings about a transformation in the first composition, the second composition, or both compositions.

Conditions that "allow" an event to occur or conditions that are "suitable" for an event to occur, or "suitable" conditions are conditions that do not prevent such events from occurring. Thus, these conditions permit, enhance, facilitate, and/or are conducive to the event. Such conditions, known in the art and described herein, may depend upon, for example, the nature of a polypeptide sequence, temperature, and buffer conditions. These conditions may also depend on what event is desired.

As used herein, the term "consists essentially," with respect to a Notch substrate of the invention, indicates that the sequence may be modified by N-terminal and/or C-terminal additions or deletions that do not cause a substantial decrease in the ability of the gamma-secretase substrate to be cleaved compared to the reference sequence.

As used herein, the term "transfection" refers to any of the methods known in the art for introducing DNA into a cell including, but not limited to, the methods of calcium phosphate or calcium chloride mediated transfection, electroporation, and infection with a retroviral vector.

As used herein, the terms "fusion protein," "chimeric protein," and related terms and phrases, refer to a protein or polypeptide engineered to contain at least two polypeptide regions or domains, each having recognizable structure, function, or similar attribute, and, optionally, a linking peptide to operatively link the two polypeptides into one continuous polypeptide. The at least two polypeptide regions in a fusion protein are derived from different sources, and therefore a fusion protein includes two polypeptide regions not normally joined together in nature.

As used herein, the terms "linking sequence" and "linker peptide" refer to one or more amino acid residues joined in peptide bonds that serve to join two polypeptide regions of differing origins in a fusion protein via a peptide bond between the linking sequence and each of the polypeptide regions.

As used herein, the terms "tag," "probe" and "label" refer interchangeably to a moiety bound to a target substance that permits easy detection or assay of the target. A tag, probe or label may include a particular amino acid sequence defining a polypeptide tag, probe or label, or it may include a non-proteinaceous moiety that may be readily detected by a laboratory assay. A given composition or substance, e.g., a polypeptide, may bear one, or more than one, tag, probe or label at the same time. Examples of tags include maltose binding protein, AviTag, the FLAG epitope, biotin, digoxigenin, glutathione dehydrogenase, horse radish peroxidase, and so forth. Additionally a tag, probe or label may include an antibody that specifically binds to a target substance, or to a second antibody. An antibody tag, probe or label may itself further bear a detectable moiety as a tag, probe or label, such as a fluorescent moiety, including a fluorescent moiety that may serve as a fluorescence donor or a fluorescence energy acceptor, or a moiety that responds in a chemiluminescence assay.

As used herein, the term "gamma-secretase assay" refers to any assay which may be used to measure the activity of gamma-secretase toward a gamma-secretase substrate.

As used herein, the terms "increase," "increases," "increased" and "decrease," "decreases," and "decreased" in the context of the activity of gamma-secretase refer, in some embodiments, to an increase, or a decrease, respectively: (i) of 0.5%, 1%. 1.5%, 2%, 5%, 10%, 20%, 30%, 40%, 50% or more; or (ii) an increase of 1.5, 2, 3, 4, or 5 fold or more.

As used herein, the terms "change," "changed," "modulate," or "modulated," in the context of the activity of gamma-secretase refer, in some embodiments, to: (i) a positive or a negative change of 0.5%, 1%. 1.5%, 2%, 5%, 10%, 20%, 30%, 40%, 50% or more; or (ii) a positive or a negative change of 1.5, 2, 3, 4, or 5 fold or more.

As used herein, the term "compound" and similar terms (such as "substance" and "agent") refers to any compound being tested for its ability to modulate gamma-secretase activity. As used herein, a compound and similar terms include, but are not limited to, peptides, peptidomimetics, amino acids, amino acid analogs, polynucleotides, polynucleotide analogs, nucleotides, nucleotide analogs, other organic and inorganic compounds (e.g., including heteroorganic and organometallic compounds). A compound may have a molecular weight of less than 10,000 Da, or less than 5,000 Da, or less than 1,000 Da, or less than 500 Da, or less than 100 Da.

As used herein, the term "gamma-secretase inhibitor" refers to any molecule, compound, and/or substance capable of reducing and/or eliminating the activity of gamma-secretase.

As used herein, the term "small molecule" and analogous terms include, but are not limited to, peptides, peptidomimetics, amino acids, amino acid analogs, polynucleotides, polynucleotide analogs, nucleotides, nucleotide analogs, other organic and inorganic compounds (e.g., including heteroorganic and organometallic compounds) and forms thereof having a molecular weight of less than 10,000 Da, or less than 5,000 Da, or less than 1,000 Da, or less than 500 Da, or less than 100 Da.

As used herein, the term "candidate," when referring to a compound relates to a test compound whose potential activity with respect to a certain property is undergoing assay. Thus the ability of the candidate compound to manifest the property has been unknown or uncharacterized prior to the assay, and becomes apparent upon carrying the assay out. A property of interest in the present disclosure is the ability to modulate gamma-secretase activity.

As used herein, the term "therapeutic agent" refers to any compound that is used for the purpose of treating and/or managing a disease or disorder. In one embodiment, an therapeutic agent is a gamma-secretase modulator. Examples of therapeutic agents include, but are not limited to, proteins, compounds, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents (e.g., anti-cancer agents), proliferation-based therapy, radiation, chemotherapy, anti-angiogenic agents, and drugs.

As used herein, the term "separating" and similar terms and phrases, when applied to a cell, connote resolving various fractions that may occur in the cell from one another. Frequently a cell is disrupted to disperse its contents into a suspending solvent prior to resolving its fractions. Disruption may be accomplished, for example, by homogenization, extrusion through a high shear device such as a French press, sonication, and so on. The resulting cell-free suspension may then be resolved into fractions as above. In general, as used herein, "separating" includes any disruption of the cell.

As used herein, the term "host cell" includes a particular subject cell transformed or transfected with a polynucleotide and the progeny or potential progeny of such a cell. Progeny of such a cell may not be identical to the parent cell transfected with the polynucleotide due to mutations or environmental influences that may occur in succeeding generations or integration of the polynucleotide into the host cell genome.

As used herein, the term "isolated," as it refers to a gamma-secretase inhibitor, means the physical state of a gamma-secretase inhibitor after being separated and/or purified from precursors and other substances found in a synthetic process (e.g., from a reaction mixture) or natural source or combination thereof according to a process or processes described herein or which are well known to the skilled artisan (e.g., chromatography, recrystallization and the like) in sufficient purity to be capable of characterization by standard analytical techniques described herein or well known to the skilled artisan. In a specific embodiment, the gamma-secretase inhibitor is at least 60% pure, at least 65% pure, at least 70% pure, at least 75% pure, at least 80% pure, at least 85% pure, at least 90% pure or at least 99% pure as assessed by techniques known to one of skill in the art.

Concentrations, amounts, cell counts, percentages and other numerical values may be presented herein in a range format. It is to be understood that such range format is used merely for convenience and brevity and should be interpreted flexibly to include not only the numerical values explicitly disclosed as the limits of the range but also to include all the individual numerical values or sub-ranges encompassed within that range as if each numerical value and sub-range were explicitly disclosed.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Antibodies

The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species. Any antibody disclosed herein binds "immunospecifically" to its cognate antigen. By immunospecific binding is meant that an antibody raised by challenging a host with a particular immunogen binds to a molecule such as an antigen that includes the immunogenic moiety with a high affinity, and binds with only a weak affinity or not at all to non-immunogen-containing molecules. As used in this definition, high affinity means having a dissociation constant less than $1 \times 10^{-6}$ M, and weak affinity means having a dissociation constant higher than $1 \times 10^{-6}$ M.

A Notch substrate described herein or a fragment thereof may be used as an immunogen to generate antibodies that immunospecifically bind the antigen, using standard techniques for polyclonal and monoclonal antibody preparation. The full-length protein maybe used or, alternatively, the invention provides antigenic peptide fragments of the antigen for use as immunogens. An antigenic peptide fragment includes at least 6 amino acid residues of the amino acid sequence of the full length protein, and encompasses an epitope thereof such that an antibody raised against the peptide forms a specific immune complex with the full length protein or with any fragment that contains the epitope. In one embodiment the antigenic peptide includes at least 9 amino acid residues, at least 10 amino acid residues, or at least 15 amino acid residues, or at least 20 amino acid residues, or at least 30 amino acid residues. In one embodiment, epitopes encompassed by the antigenic peptide are regions of the protein that are located on its surface; commonly these are hydrophilic regions.

In certain embodiments of the invention, at least one epitope encompassed by the antigenic peptide is a region of a Notch protein or fragment thereof that is located on the surface of the protein, e.g., a hydrophilic region. A hydrophobicity analysis of the protein sequence will indicate which regions of the polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824-3828; Kyte and Doolittle 1982, *J. Mol. Biol.* 157: 105-142. Antibodies that are specific for one or more domains within an antigenic protein, or derivatives, fragments, analogs or homologs thereof, are also provided herein.

A protein of the present invention or a thereof may be used as an immunogen in the generation of antibodies that immunospecifically bind immunogen. In one embodiment, the polypeptide used as an immunogen is at least 6 consecutive amino acids chosen from VLLSRKRRR (SEQ ID NO:2). In one embodiment the immunogen is VLLSRKRRR (SEQ ID NO:2), and in another embodiment the immunogen is a polypeptide that includes VLLSRKRRR (SEQ ID NO:2). For instance, the immunogen may include VLLSRKRRR (SEQ ID NO:2) and other amino acids that are naturally flank this sequence in wild type Notch polypeptides. In one embodiment, the immunogen may include VLLSRKRRR (SEQ ID NO:2) and other non-native amino acids, and/or other molecules. For instance, the immunogen may include VLLSRKRRR. (SEQ ID NO:2) and a carrier such as, but not limited to, keyhole limpet hemocyanin. In one embodiment antibody binds to an epitope that is exposed, and able to interact with an antiboy, after cleavage by a gamma-secretase at an S2 or S3 site.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y.). Some of these antibodies are discussed below.

1. Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation may contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation may further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which may be employed include MPL-TDM adjuvant (monophosphoryl Lipid A, synthetic trehalose dicorynomycolate).

The polyclonal antibody molecules directed against the immunogenic protein may be isolated from the mammal (e.g., from the blood) and further purified by known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

2. Monoclonal Antibodies

The term "monoclonal antibody" (MAb) or "monoclonal antibody composition," as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which may be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor: J. Jmmunol., 133:3001 (1984); Brodeur et al.: Monoclonal Antibody Production Techniques and Applications, Marcel Dekker, Inc., New York, (1987) pp. 51-63).

The culture medium in which the hybridoma cells are cultured may then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). It is an objective, especially important in therapeutic applications of monoclonal antibodies, to identify antibodies having a high degree of specificity and a high binding affinity for the target antigen.

After the desired hybridoma cells are identified, the clones may be subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention may be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison (1994) Nature 368, 812-13) or by covalently joining to the immunoglobulin coding sequence all or part of the coding sequence for a non-immunoglobulin polypeptide. Such a non-immunoglobulin polypeptide may be substituted for the constant domains of an antibody of the invention, or may be substituted for the variable domains of one antigen-combining site of an antibody of the invention to create a chimeric bivalent antibody.

3. $F_{ab}$ Fragments and Single Chain Antibodies

According to the invention, techniques may be adapted for the production of single-chain antibodies specific to an antigenic protein of the invention (see e.g., U.S. Pat. No. 4,946,778). In addition, methods may be adapted for the construction of Fab expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Notch Recombinant Vectors and Host Cells

The Notch substrates provided herein may be prepared by standard recombinant DNA techniques or by protein synthetic techniques, e.g., by use of a peptide synthesizer. For example, a polynucleotide encoding a Notch substrate of the invention may be synthesized by conventional techniques including automated DNA synthesizers. Alternatively, PCR amplification of gene fragments may be carried out using anchor primers which give rise to complementary overhangs between two consecutive gene fragments which may subsequently be annealed and reamplified to generate a chimeric gene sequence (see, e.g., *Current Protocols in Molecular Biology*, Ausubel et al., eds., John Wiley & Sons, 1992).

The nucleotide sequences encoding Notch substrates may be obtained from any information available to those of skill in the art (e.g., from GenBank, the literature, or by routine cloning). The nucleotide sequence coding for a Notch substrate may be modified, if desired, using approaches known to those of skill in the art, e.g., site-directed mutagenesis, and inserted into an appropriate expression vector, e.g., a vector which contains the necessary elements for the transcription and translation of the inserted protein-coding sequence. In some instances, a sequence encoding a Notch polypeptide may be truncated in order to remove a specific domain, such as the targeting domain. The techniques for modifying or truncating DNA are well known to those of skill in the art of molecular biology.

A variety of host-vector systems may be utilized in the present invention to express the protein-coding sequence. These include, but are not limited to, mammalian cell systems infected with virus (e.g., vaccinia virus, adenovirus, etc.); insect cell systems infected with virus (e.g., baculovirus); microorganisms such as yeast (e.g. *Pichia*) containing yeast vectors; or bacteria (such as *E. coli*) transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Another aspect of the disclosure pertains to vectors, preferably expression vectors, containing a polynucleotide encoding a Notch substrate. As used herein, the term "vector" refers to a polynucleotide capable of transporting another polynucleotide to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention include a polynucleotide of the invention in a form suitable for expression of the polynucleotide in a host cell, which means that the recombinant expression vectors include one or more regulatory sequences, selected on the basis of the host cells to be used for expression, that is operatively linked to the polynucleotide sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) GENE EXPRESSION TECHNOLOGY: METHODS IN ENZYMOLOGY 185, Academic Press, San Diego, Calif. Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention may be introduced into host cells to thereby produce polypeptides such as a Notch substrate. Examples of plasmid vectors that encode a Notch substrate and that is suitably labeled for use in various assay methods disclosed herein include, but are not limited to, those illustrated in FIGS. 1A (pIAD16-MBP-N-1-Avi) and 2 (pIAD16 with N1-Sb1 insert).

The expression of a Notch substrate of the invention may be controlled by a promoter or enhancer element. Promoters which may be used to control expression of a Notch substrate include, but are not limited to, the SV40 early promoter region (Bemoist and Chambon, 1981, Nature 290: 304-310), the promoter contained in the 3' long terminal repeat of Rous sarcoma virus (Yamamoto, et al., 1980, *Cell* 22:787-797), the herpes thymidine kinase promoter (Wagner et al., 1981, *Proc. Natl. Acad. Sci. U.S.A.* 78:1441-1445), the regulatory sequences of the rnetallothionein gene (Brinster et al., 1982, *Nature* 296:39-42), the tetracycline (Tet) promoter (Gossen et al., 1995, *Proc. Nat. Acad. Sci. U.S.A.* 89:5547-5551); prokaryotic expression vectors such as the β-lactamase promoter (VIIIa-Kamaroff, et al., 1978, *Proc. Natl. Acad. Sci. U.S.A.* 75:3727-3731), or the tac promoter (DeBoer, et al., 1983, *Proc. Natl. Acad. Sci. U.S.A.* 80:21-25; see also "Useful proteins from recombinant bacteria," in *Scientific American*, 1980, 242:74-94); plant expression vectors including the nopaline synthetase promoter region (Herrera-Estrella et al., *Nature* 303:209-213) or the cauliflower mosaic virus 35S RNA promoter (Gardner, et al., 1981, *Nucl. Acids Res.* 9:2871), and the promoter of the photosynthetic enzyme ribulose biphosphate carboxylase (Herrera-Estrella et al., 1984, *Nature* 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, *Cell* 38:639-646; Omitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, *Nature* 315:115-122), immunoglobulin gene control region which is active in lymphoid cells (Grosschedl et al., 1984, *Cell* 38:647-658; Adames et al., 1985, Nature 318:533-538; Alexander et al., 1987, *Mol. Cell. Biol.* 7:1436-1444), mouse mammary tumor virus control region which is active in testicular, breast, lymphoid and mast cells (Leder et al., 1986, *Cell* 45:485-495), albumin gene control region which is active in liver (Pinkert et al., 1987, *Genes and Devel.* 1:268-276), alpha-fetoprotein gene control region which is active in liver (Krumlauf et al., 1985, *Mol. Cell. Biol.* 5:1639-1648; Hammer et al., 1987, *Science* 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, *Cell* 48:703-712); myosin light chain-2 gene control region which is active in skeletal muscle (Sani, 1985, *Nature* 314:283-286); neuronal-specific enolase (NSE) which is active in neuronal cells (Morelli et al., 1999, *Gen. Virol.* 80:571-83); brain-derived neurotrophic factor (BDNF) gene control region which is active in neuronal cells (Tabuchi et al., 1998, *Biochem. Biophysic. Res. Com.* 253:818-823); glial fibrillary acidic protein (GFAP) promoter which is active in astrocytes (Gomes et al., 1999, *Braz. J. Med. Biol. Res.* 32(5):619-631; Morelli et al., 1999, *Gen. Virol.* 80:571-83) and gonadotropic releasing hormone gene control region which is active in the hypothalamus (Mason et al., 1986, *Science* 234:1372-1378). In one embodiment, the expression of a Notch substrate of the invention is regulated by a constitutive promoter. In another embodiment, the expression is regulated by an inducible promoter. In another embodiment, the expression is regulated by a tissue-specific promoter.

The recombinant expression vectors of the invention may be designed for expression of the Notch substrate in prokaryotic or eukaryotic cells. For example, the Notch substrate may be expressed in bacterial cells such as *E. coli*, insect cells (using baculovirus expression vectors) yeast cells or mammalian cells. Suitable host cells are discussed further in Goeddel (Goeddel (1990) GENE EXPRESSION TECHNOLOGY: METHODS IN ENZYMOLOGY 185, Academic Press, San Diego, Calif.). Alternatively, the recombinant expression vector may be transcribed and translated in vitro, for example using T7 promoter regulatory sequences and T7 polymerase.

In a specific embodiment, a vector is used that includes a promoter operably linked to a Notch substrate encoding polynucleotide, one or more origins of replication and, optionally, one or more selectable markers (e.g., an antibiotic resistance gene).

Expression of proteins in prokaryotes is most often carried out in K coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein, (2) to increase the solubility of the recombinant protein, and/or (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include but are not limited to Factor Xa, thrombin and enterokinase. Common fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al. (1990) GENE EXPRESSION TECHNOLOGY: METHODS IN ENZYMOLOGY 185, Academic Press, San Diego, Calif. 60-89).

One strategy to maximize recombinant protein expression in *E. coli* is to express the protein in a host bacteria with an impaired capacity to proteolytically cleave the recombinant protein. See, Gottesman (1990) GENE EXPRESSION TECHNOLOGY: METHODS IN ENZYMOLOGY 185, Academic Press, San Diego, Calif. 119-128. Another strategy is to alter the nucleic acid sequence of the polynucleotide to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention may be carried out by standard DNA synthesis techniques.

In another embodiment, the Notch expression vector is a yeast expression vector. Examples of vectors for expression in yeast *S. cerivisae* include pYepSec1 (Baldari, et al., (1987) *EMBO J* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, the Notch substrate may be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156-2165) and the pVL series (Lucklow and Summers (1989) *Virology* 170:31-39).

In yet another embodiment, a polynucleotide of the invention is expressed in mammalian cells using a mammalian expression vector. Examples of mammalian expression vectors include pCDM8 (Seed (1987) Nature 329:840) and pMT2PC (Kaufman et al. (1987) *EMBO J.* 6: 187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the polynucleotide preferentially in a particular cell type (e.g., tissue-specific regulatory elements are used to express the polynucleotide). Tissue-specific regulatory elements are known in the art. Non-limiting examples of suitable tissue-specific promoters include the albumin promoter (liver-specific; Pinkert et al. (1987) *Genes Dev* 1:268-277), lymphoid-specific promoters (Calame and Eaton (1988) *Adv Immunol* 43:235-275), in particular promoters of T cell receptors (Winoto and Baltimore (1989) *EMBO J* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166).

Developmentally-regulated promoters are also encompassed, e.g., the murine hox promoters (Kessel and Gruss (1990) *Science* 249:374-379) and the α-fetoprotein promoter (Campes and Tilghman (1989) *Genes Dev* 3:537-546).

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell may be any prokaryotic or eukaryotic cell. For example, a Notch substrate may be expressed in bacterial cells such as *E. coli*, insect cells, yeast or mammalian cells (such as Chinese hamster ovary cells (CHO) or COS cells). Other suitable host cells are known to those skilled in the art.

Vector DNA may be introduced into prokaryotic or eukaryotic cells via conventional transformation or transfection techniques. As used herein, the terms "transformation" and "transfection" are intended to refer to a variety of art-recognized techniques for introducing foreign polynucleotides (e.g., DNA) into a host cell, including calcium phosphate or calcium chloride co-precipitation, DEAE-dextran-mediated transfection, lipofection, or electroporation. Suitable methods for transforming or transfecting host cells may be found in Sambrook, et al. (2001), Ausubel et al. (2002), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. A polynucleotide encoding a selectable marker may be introduced into a host cell on the same vector as that encoding the Notch substrate or may be introduced on a separate vector. Cells stably transfected with the introduced polynucleotide may be identified by drug selection (e.g., cells that have incorporated the selectable marker gene will survive, while the other cells die).

A host cell of the invention, such as a prokaryotic or eukaryotic host cell in culture, may be used to produce (e.g., express) the Notch substrate. Accordingly, the invention further provides methods for producing the Notch substrate using the host cells of the invention. In one embodiment, the method includes culturing the host cell of invention (into which a recombinant expression vector encoding the Notch substrate has been introduced) in a suitable medium such that the Notch substrate is produced In addition, a host cell strain may be chosen which modulates the expression of the inserted sequences, or modifies and processes the gene product in the specific fashion desired. Expression from certain promoters may be elevated in the presence of certain inducers; thus, expression of the genetically engineered gamma-secretase substrates may be controlled. Furthermore, different host cells have characteristic and specific mechanisms for the translational and post-translational processing and modification (e.g., glycosylation, phosphorylation) of proteins. Appropriate cell lines or host systems may be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, NSO, and in particular, neuronal cell lines such as, for example, SK-N-AS, SK-N-FI, SK-N-DZ human neuroblastomas (Sugimoto et al., 1984, *J. Natl. Cancer Inst.* 73: 51-57), SK-N-SH human neuroblastoma (*Biochim. Biophys. Acta,* 1982, 704: 450-460), Daoy human cerebellar medulloblastoma (He et al., 1992, *Cancer Res.* 52: 1144-1148) DBTRG-05MG glioblastoma cells (Kruse et al., 1992, *In Vitro Cell. Dev. Biol.* 28A: 609-614), LMR-32 human neuroblastoma (*Cancer Res.,* 1970, 30: 2110-2118), 1321N1 human astrocytoma (*Proc. Natl. Acad. Sci. U.S.A.* 1977, 74: 4816), MOG-G-CCM human astrocytoma (*Br. J. Cancer* 1984, 49: 269), U87MG human glioblastoma-astrocytoma (*Acta Pathol. Microbiol. Scand.* 1968, 74: 465-486), A172 human glioblastoma (Olopade et al., 1992, *Cancer Res.* 52: 2523-2529), C6 rat glioma cells (Benda et al., 1968, Science 161: 370-371), Neuro-2a mouse neuroblastoma (*Proc. Natl. Acad. Sci. U.S.A.* 1970, 65: 129-136), NB41A3 mouse neuroblastoma (*Proc. Natl. Acad. Sci. U.S.A.* 1962, 48: 1184-1190), SCP sheep choroid plexus (Bolin et al., 1994, *J. Virol. Methods* 48: 211-221), G355-5, PG-4 Cat normal astrocyte (Haapala et al., 1985, *J. Virol.* 53: 827-833), Mpf ferret brain (Trowbridge et al., 1982, *In Vitro* 18: 952-960), and normal cell lines such as, for example, CTX TNA2 rat normal cortex brain (Radany et al., 1992, *Proc. Natl. Acad. Sci. U.S.A.* 89: 6467-6471) such as, for example, CRL7030 and Hs578Bst. Furthermore, different vector/host expression systems may effect processing reactions to different extents.

For long-term, high-yield production of gamma-secretase substrates, such as a Notch substrate, stable expression is preferred. For example, cell lines which stably express the gamma-secretase substrate of the invention may be engineered. Rather than using expression vectors which contain viral origins of replication, host cells may be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn may be cloned and expanded into cell lines. This method may advantageously be used to engineer cell lines which express a gamma-secretase substrate of the invention.

A number of selection systems may be used, including but not limited to the herpes simplex virus thymidine kinase (Wigler, et al., 1977, *Cell* 11:223), hypoxanthine-guanine phosphoribosyltransferase (Szybalska & Szybalski, 1962, *Proc. Natl. Acad. Sci. U.S.A.* 48:2026), and adenine phosphoribosyltransferase (Lowy, et al., 1980, *Cell* 22:817) genes may be employed in tk–, hgprt– or aprt– cells, respectively. Also, antimetabolite resistance may be used as the basis of selection for dhfr, which confers resistance to methotrexate (Wigler, et al., 1980, *Proc. Natl. Acad. Sci. U.S.A.* 77:3567; O'Hare, et al., 1981, *Proc. Natl. Acad. Sci.*

U.S.A. 78:1527); gpt, which confers resist-once to mycophenolic acid (Mulligan & Berg, 1981, *Proc. Natl. Acad. Sci. U.S.A.* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147).

Once a gamma-secretase substrate of the invention has been produced by recombinant expression or by chemical synthesis, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

Detection and Labeling

Generally an analyte, such as a product of cleavage of a Notch substrate by gamma-secretase, may be detected in many ways. Detecting may include any one or more processes that result in the ability to observe the presence and/or the amount of a proteolytic cleavage reaction. Physical, chemical or biological methods may be used to detect and quantify a product. Physical methods include, by way of nonlimiting example, surface plasmon resonance (SPR) detection, using SPR to detect a labeled product to an immobilized probe, or having a probe in a chromatographic medium and detecting binding of a bound product molecule in the chromatographic medium. Physical methods further include a gel electrophoresis or capillary electrophoresis format in which product molecules are resolved from other molecules, and the resolved products are detected. Chemical methods include hybridization methods and formation of specific binding pairs generally in which a product molecule binds to a probe. Biological methods include causing a bound target molecule to exert a biological effect on a cell, and detecting the effect. The present invention discloses examples of biological effects which may be used as a biological assay. In many embodiments, a product or member of a specific binding pair may be labeled as described herein to assist in detection and quantitation.

An advantageous way of accomplishing detection is to use a labeled form of a cleavage product molecule, such as a Notch substrate, and to detect the bound label. A label may be a radioisotopic label, such as $^{125}$I, $^{35}$S, $^{32}$P, $^{14}$C, or $^{3}$H, for example, that is detectable by its radioactivity. Alternatively, a label may be selected such that it may be detected using a spectroscopic method, for example. In one instance, a label may be a chromophore, absorbing incident ultraviolet, visible, infrared, microwave or similar electromagnetic radiation. A preferred label is one detectable by luminescence. Generally, luminescence refers to the emission of electromagnetic radiation from a substance or a chemical. The radiation may occur in any region of the electromagnetic spectrum; i.e., the frequency of the emitted radiation may be anywhere in the spectrum. Commonly luminescence occurs in the ultraviolet, visible, or infrared spectral regions. Luminescence includes fluorescence, phosphorescence, and chemiluminescence. Thus a label that fluoresces, or that phosphoresces, or that induces a chemiluminscent reaction, may be employed. Nonlimiting examples of suitable fluorescent labels, or fluorochromes, include a Eu label, a fluorescein label, a rhodamine label, a phycoerythrin label, a phycocyanin label, Cy-3, Cy-5, an allophycocyanin label, an o-phthalaldehyde label, and a fluorescamine label. Luminescent labels afford detection with high sensitivity. A label may furthermore be a magnetic resonance label, such as a stable free radical label detectable by electron paramagnetic resonance, or a nuclear label, detectable by nuclear magnetic resonance. A label may still further be a ligand in a specific ligand-receptor pair; the presence of the ligand is then detected by the secondary binding of an additional ligand-specific receptor, which commonly is itself labeled for detection. Nonlimiting examples of such ligand-receptor pairs include biotin and streptavidin or avidin, a hapten such as digoxigenin or antigen and its specific antibody, and so forth.

Detecting, quantitating, including labeling, methods are known generally to workers of skill in fields related to the present invention, including, by way of nonlimiting example, workers of skill in spectroscopy, nucleic acid chemistry, biochemistry, molecular biology and cell biology. Quantitating assesses the quantity, mass, or concentration of a Notch substrate cleavage product, or fragment thereof, that results from the action of a gamma-secreatase. Quantitation includes determining the amount of change in a physical, chemical, or biological property as described herein. For example, the intensity of a signal originating from a label may be used to assess the quantity of the cleaved polypeptide bound to the probe. Any equivalent process yielding a way of detecting the presence and/or the quantity, mass, or concentration of a peptide cleavage product is envisioned to be within the scope of the present invention.

Electrochemiluminescence (ECL) Assay of Notch Cleavage Product Peptides

In one embodiment, a method for identifying a product of the gamma-secretase catalyzed cleavage of a Notch substrate is an electrochemiluminescence ("ECL") assay (see Li, et al., 2000, *Proc. Natl. Acad. Sci. USA* 97:6138-6143; and Yin, et al., 2007, *J. Biol. Chem.* 282:23639-23644). In an ECL assay an analyte to be detected is labeled with a chemiluminescent moiety whose chemiluminescence is redox dependent. A commonly used chemiluminescent moiety is a $Ru^{+2}$ complex which becomes chemiluminescent, and hence detectable with high sensitivity, upon oxidation to $Ru^{+3}$. Alternative electrochemiluminescent (ECL) probes equivalent to $Ru^{+2}$ complexes are contemplated for use herein. As implemented in various Examples provided herein, an antibody specific for an intended epitope such as one revealed in a gamma-secretase proteolysis product, such as a cleaved Notch substrate, is conjugated to a $Ru^{+2}$ complex. The moiety so conjugated may be termed "ruthenylated" herein. As applied herein an ECL assay includes: (a) contacting a Notch substrate or a fragment thereof with a composition containing gamma-secretase; (b) incubating the Notch substrate with the gamma-secretase containing composition under suitable conditions for a time period sufficient for gamma-secretase activity to take place; (c) adding a ruthenylated antibody that specifically binds a cleavage product but not the Notch substrate or fragment thereof; and (d) detecting a product bound to the product-specific ruthenylated antibody using ECL. ECL techniques are known in the art and described in, e.g., Yang, et al., 1994, *Bio/Technology* 12:193-194; and Khorkova, et al., 1998, *J. Neurosci. Methods* 82:159-166

In a specific embodiment, the source of gamma-secretase is a cell or cell membrane, e.g., a HeLa cell or other mammalian cell or a constituent membrane thereof, and the incubation of step (b) takes place in the presence of a detergent, e.g., CHAPSO, at a concentration optimized for the assay.

In another specific embodiment, the anti-product antibody is one that binds a newly revealed peptide terminus that is created after gamma-secretase mediated cleavage of the Notch substrate, such as an antibody raised using the polypetpide VLLSRKRRR (SEQ ID NO:2). An example of such an antibody is the SM320 antibody described herein. Other antibodies raised against analogous neoepitopes newly revealed upon proteolytic cleavage of a Notch substrate or a variant thereof are also useful for detecting the activity of γ-secretase on the substrate.

In another specific embodiment, a Notch substrate of the invention or fragment thereof includes a modification to at least one amino acid, including a conservative amino acid substitution, that preserves the modified substrate as a susceptible to the action of γ-secretase.

Homogeneous Time Resolved Fluorescence (HTRF) Assay for Notch Substrate Cleavage In another embodiment, an assay method for detecting and quantifying the gamma-secretase catalyzed proteolysis of a Notch substrate is a Homogeneous Time Resolved Fluorescence (HTRF) assay. HTRF combines a) homogeneous fluorescence detection phase (e.g. carried out in liquid solution) with b) time resolution of signal detection and c) assessment of the distance separating an excitation donor and a fluorescence emitter to eliminate background fluorescence and provide both high sensitivity and high specificity of detection. A long-lived fluorophore, commonly a complex of a rare earth metal ion, such as a cryptate complex of the ion, permits detection to be delayed by time resolution until interfering background fluorescence will already have decayed. Fluorescence resonance energy transfer between specific fluorescence donor and fluorescence acceptor further enhance specificity by restricting ultimate detection of fluorescence to instances of, for example, complex formation between them. As implemented in this disclosure, an HTRF assay includes: (a) contacting a Notch substrate of the invention or a fragment thereof with a source of gamma-secretase, wherein the Notch substrate includes a detectable tag or label; (b) incubating the Notch substrate of the invention with a composition containing, or suspected of containing, gamma-secretase for a time period sufficient for gamma-secretase activity to take place thereby providing a product bearing the detectable tag or label; (c) adding an HTRF detection mixture that includes (i) a first reagent, such as an antibody, that recognizes a gamma-secretase-cleaved peptide resulting from Notch cleavage but does not recognize uncleaved gamma-secretase substrates and (ii) a rare earth metal-labeled second antibody that binds the first antibody, and (iii) a fluorophore-conjugated reagent that binds to the detectable tag or label; (d) incubating the HTRF detection mixture with the product mixture; and (e) measuring the presence and/or amount of the Notch cleavage product or fragment thereof using, generally, Fluorescence Resonance Energy Transfer ("FRET"), or more particularly, Homogeneous Time Resolved Fluorescence (HTRF), by exciting the rare earth metal and detecting fluorescence from the fluorophore of the conjugated reagent. A cognate assay may be performed on a negative control in which either the enzyme or the Notch substrate is omitted.

In a specific embodiment, a source of gamma-secretase is a cell or cell membrane, e.g., a HeLa cell or other mammalian cell, or a constituent membrane thereof, and the incubation of step (b) takes place in the presence of a detergent, e.g., CHAPSO, at a concentration optimized for the assay.

In a specific embodiment, the antibody that recognizes gamma-secretase-cleaved peptides resulting from cleavage of the Notch substrate or fragment thereof but does recognize uncleaved gamma-secretase substrates is the SM320 antibody.

Cell-Based Assays for Cleavage of Notch Substrates

In another embodiment, a method for assaying for the proteolytic cleavage of a Notch substrate of the invention by gamma-secretase is a cell-based assay. Such an assay may include: (a) transfecting cells containing, or suspected of containing, gamma-secretase activity with a plasmid containing the nucleotide sequence encoding a Notch substrate of the invention; (b) incubating the cells for a time period sufficient for the expression of the Notch substrate, and sufficient for gamma-secretase activity on the Notch substrate to occur; and (c) detecting a cleaved Notch substrate secreted by the cells, or included in a homogenate prepared from the cells, or in a mounted preparation of the cells on a surface. Detection of secreted product, or of product contained in a homogenate, may be carried out in various embodiments, for example, by Western analysis (SDS-PAGE and immunoblotting using a product-specific antibody), or by ECL, HTRF, chemiluminescence-coupled FRET (see Examples). Detection of product peptides in situ may be carried out by immunohistochemical analysis using an antibody specific for a product of the cleavage reaction. In various embodiments the antibody specific for a product of the cleavage reaction is the novel SM320 antibody disclosed herein. In certain embodiments, more generally, an antibody useful for detection in a cell-based assay specifically binds either the C-terminus or the N-terminus of the product peptide that is exposed after gamma-secretase mediated cleavage of the Notch substrate, such as disclosed herein.

In a specific embodiment, the cells contain endogenous gamma-secretase. In another specific embodiment, the cells are HEK293 cells or other mammalian cell.

In another embodiment, the level of product peptide resulting from the action of γ-secretase on a Notch substrate of the invention or a fragment thereof is measured by mass spectrometry/surface enhanced laser desorption/ionization time-of-flight analysis (SELDI-TOF).

Screens for Gamma-Secretase Modulators

ECL Screening Assay for Identifying Modulators of Gamma-Secretase Activity

In one embodiment, a method for the identification and/or validation of a gamma-secretase modulator may be an ECL assay, wherein said method includes: (a) contacting a candidate compound which is a potential modulator of gamma-secretase activity with a Notch substrate of the invention and a composition containing gamma-secretase to provide a candidate assay mixture, (b) incubating the candidate assay mixture for a time period sufficient for gamma-secretase activity to take place; (c) adding ruthenylated antibody that specifically binds a cleavage product resulting from the action of the gamma-secretase; and (d) detecting the γ-secretase product by the product-specific ruthenylated antibody using ECL. Using this assay, a candidate compound is identified or validated as a gamma-secretase modulator if the activity of gamma-secretase toward a Notch substrate is altered either positively or negatively relative to the activity of gamma-secretase toward the Notch substrate in the absence of the candidate modulator.

In a specific embodiment, the source of gamma-secretase activity is a cell membrane, e.g., a cell membrane from a HeLa cell or other mammalian cell, and the incubation of step (b) takes place in the presence of a detergent, e.g., CHAPSO (0.25%).

In another specific embodiment, the antibody binds either the C-terminus or the N-terminus of the Notch substrate of the invention or fragment thereof that is exposed after gamma-secretase mediated cleavage of the substrate, such as the novel SM320 antibody disclosed herein.

HTRF Screening Assay for Modulators of Gamma-Secretase Activity

In another embodiment, an assay method for the identification and/or validation of a gamma-secretase modulator for proteolytic cleavage of a Notch substrate or fragment thereof by gamma-secretase uses HTRF. This method includes steps of: (a) contacting a candidate compound that is a potential gamma-secretase modulator with a Notch substrate and a composition containing gamma-secretase activity to provide a candidate assay mixture; wherein the Notch substrate includes a detectable tag or label; (b) incubating the candidate assay mixture under suitable conditions for a time period sufficient for gamma-secretase activity to take place; (c) adding an HTRF detection mixture that includes (i) a first antibody that recognizes a gamma-secretase-cleaved peptide resulting from cleavage of the Notch substrate but does not recognize uncleaved Notch substrate, (ii) a rare earth metal-labeled second antibody that binds the first antibody, and (iii) a fluorophore-conjugated reagent that binds to the detectable tag or label; (d) incubating said HTRF detection mixture with the candidate assay mixture; and (e) measuring the cleavage of the Notch substrate of the invention or variant thereof by gamma-secretase using, generally, Fluorescence Resonance Energy Transfer ("FRET"), or more particularly, Homogeneous Time Resolved Fluorescence (HTRF), by exciting the rare earth metal and detecting fluorescence from the fluorophore of the conjugated reagent. A candidate compound is identified or validated as a gamma-secretase modulator if the activity of gamma-secretase toward Notch substrate is modulated either positively or negatively relative to the activity of gamma-secretase toward the Notch substrate in the absence of the candidate gamma-secretase modulator.

In a specific embodiment, a source of gamma-secretase is a cell or cell membrane, e.g., a HeLa cell or other mammalian cell or a constituent membrane thereof, and the incubation of step (b) takes place in the presence of a detergent, e.g., CHAPSO, at a concentration optimized for the assay.

In a specific embodiment, the antibody that recognizes gamma-secretase-cleaved Notch substrate resulting from cleavage of the Notch substrate but does not recognize uncleaved Notch substrates is the novel SM320 antibody disclosed herein.

Cell-Based Assays for Identifying Modulators of Gamma-Secretase Activity

In another aspect, an assay method for the identification or validation of a gamma-secretase modulator includes a cell-based assay. This method includes: (a) transfecting cells that harbor gamma-secretase activity with a plasmid containing the nucleotide sequence encoding a Notch substrate; (b) adding a candidate modulator of gamma-secretase activity to provide a candidate assay mixture; (c) incubating said candidate assay mixture for a time period sufficient for gamma-secretase activity to occur; and (d) detecting a cleaved Notch substrate product secreted by the cells, or included in a homogenate prepared from the cells, or in a mounted preparation of the cells on a surface. Detection of secreted product, or of product contained in a homogenate, may be carried out in various embodiments, for example, by Western analysis (SDS-PAGE and immunoblotting using a product-specific antibody), or by ECL, HTRF, chemiluminescence-coupled FRET (see Examples). Detection of product peptides in situ may be carried out by immunohistochemical analysis using an antibody specific for a product of the cleavage reaction. In various embodiments the antibody specific for a product of the cleavage reaction is the novel SM320 antibody disclosed herein. In certain embodiments, more generally, an antibody useful for detection in a cell-based assay specifically binds a gamma-secretase-cleaved peptide resulting from cleavage of the Notch substrate but does not recognize uncleaved Notch substrate. As a result of this assay a modulator of gamma-secretase activity is identified or validated if the activity of gamma-secretase toward the Notch substrate is modulated either positively or negatively relative to the activity of gamma-secretase toward the Notch substrate in the absence of the candidate modulator.

In a specific embodiment, a source of gamma-secretase is a cell or cell membrane, e.g., a HeLa cell, HEK293 cell, or other mammalian cell or a constituent membrane thereof, and the incubation of step (b) takes place in the presence of a detergent, e.g., CHAPSO, at a concentration optimized for the assay.

In another specific embodiment, an antibody that binds either the C-terminus or the N-terminus of the Notch substrate that is exposed after gamma-secretase mediated cleavage of the substrate, such as the novel SM320 antibody disclosed herein, is added to the cell conditioned media (containing secreted Notch-derived product) and the level of the Notch product peptide secreted by the cells is measured by ECL.

In another embodiment, the amount of a Notch product peptide secreted by the cells or contained in a cell homogenate obtained from the candidate assay mixture is measured by Western Blot, using an antibody that specifically binds the Notch product peptide. In a specific embodiment, the antibody binds either the C-terminus or the N-terminus of the Notch substrate of the invention or variant thereof that is exposed after gamma-secretase mediated cleavage of the substrate, such as the novel SM320 antibody disclosed herein In another embodiment, the amount of a Notch product peptide secreted by the cells or contained in a cell homogenate obtained from the candidate assay mixture is measured by mass spectrometry/surface enhanced laser desorption/ionization time-of-flight analysis (SELDI-TOF).

Combinatorial Chemical Libraries

Assays for gamma-secretase activity, using labeled or detectable Notch substrates, are identified herein. As described herein, and disclosed in several Examples herein, these assays are adaptable for application in high throughput screens of candidate chemical compounds in a quest for modulators of gamma-secretase activity. In many embodiments such assays are implemented in multiwell plates, including 96-well, 384-well, and 1536-well plates. Candidate compounds are provided for these screens from extended chemical libraries. Preparation of chemical libraries are widely known in the field. Combinatorial approaches to introducing framework components as well as peripheral substituents have been developed, including techniques for tagging each synthesis so that intermediates and products are identified throughout the course of the synthesis. Other libraries are prepared from a broad range naturally occurring substances, and still others from assemblages of pharmaceutical agents already known to possess therapeutic effects or therapeutic potential for a broad range of medical indications. Nonlimiting examples of preparation and uses of chemical libraries, including combinatorial chemical libraries, include U.S. Pat. No. 7,083,812, entitled "Chemical library preparation method from natural product"; U.S. Pat. No. 6,936,477, entitled "Complex combinatorial chemical libraries encoded with tags"; U.S. Patent Application Publication 20090005256, entitled "Analysis of Encoded Chemical Libraries"; U.S. Pat. No. 6,800,444, entitled "Complex chemical libraries"; International publication WO/2006/102542, entitled "Diverse Chemical Libraries Bound To Small Particles With Paramagnetic Properties"; U.S. Pat. No. 6,625,546, directed to the direct identification of a chemical compound structure following solid phase synthesis of a chemical compound library; U.S. Pat. No. 6,625,546, directed to methods for using structural identification technology to increase the productivity of solid phase synthesis strategies; and "Designed chemical libraries for hit/lead optimization," Cooper T and Andrews-Cramer, K, Innovations in Pharmaceutical Technology, June 2000, pp. 46-53.

EXAMPLES

Experimental Procedures

Peptide Synthesis

The neoepitope peptide VLLSRKRRRC corresponding to the new N-terminal sequence generated when γ-secretase cleaves human Notch1 at the S3 site (24; residues 1755-1763) was synthesized with an automated solid phase peptide synthesizer (ProteinTech) using Fmoc chemistry. The peptides were cleaved from the resin with Reagent R (90% TFA, 5% thioanisole, 3% EDT, 2% anisole) for two hours and then precipitated with cold ethyl ether. Precipitated peptides were lyophilized and confirmed with HPLC and LC/MS (Agilent).

Production of Antibody SM320 Specific for Detecting γ-Secretase Activity on Notch The neoepitope VLLSRKRRRC, which serves as a peptide antigen to detect the Notch cleavage product, was conjugated to maleimide functionalized keyhole limpet hemocyanin (KLH) according to the manufacturer's instructions (Pierce Chemical Co., Rockford, Ill.). The KLH-conjugated antigen was sent to Covance Inc. for rabbit vaccination. Once serum was collected, two volumes of 60 mM sodium acetate buffer (pH 4.0) was added to the serum. Caprylic acid was added to the serum and the resulting mixture was stirred for 30 minutes at room temperature. The mixture was then centrifuged at 5000 g for 10 minutes and the supernatant was dialyzed into phosphate buffered saline (PBS). Dialzyed supernatant that contains predominantly IgG immunoglobulin was passed through a column of resin (Pierce) derivatized with immobilized VLLSRKRRRC antigen to capture the anti-Notch peptide antibody. After initial characterization of two sera, SM320 and SM321, neoepitope antibodies were purified by affinity chromatography with peptide immobilized resin. SM320 was used for this study. The purified antibody, named SM320, was stored at −80° C.

Production of Recombinant Notch1 substrate, N1-Sb1

Figure 2:
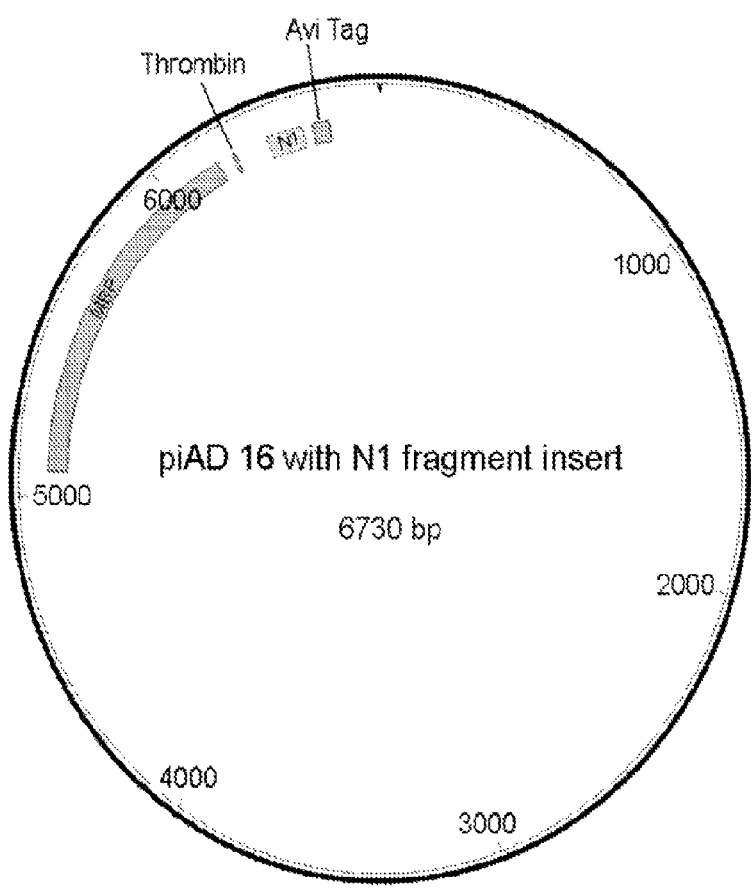
FIG. 2 Plasmid map of pIAD16 with N1-Sb1 insert.
Figure 3:
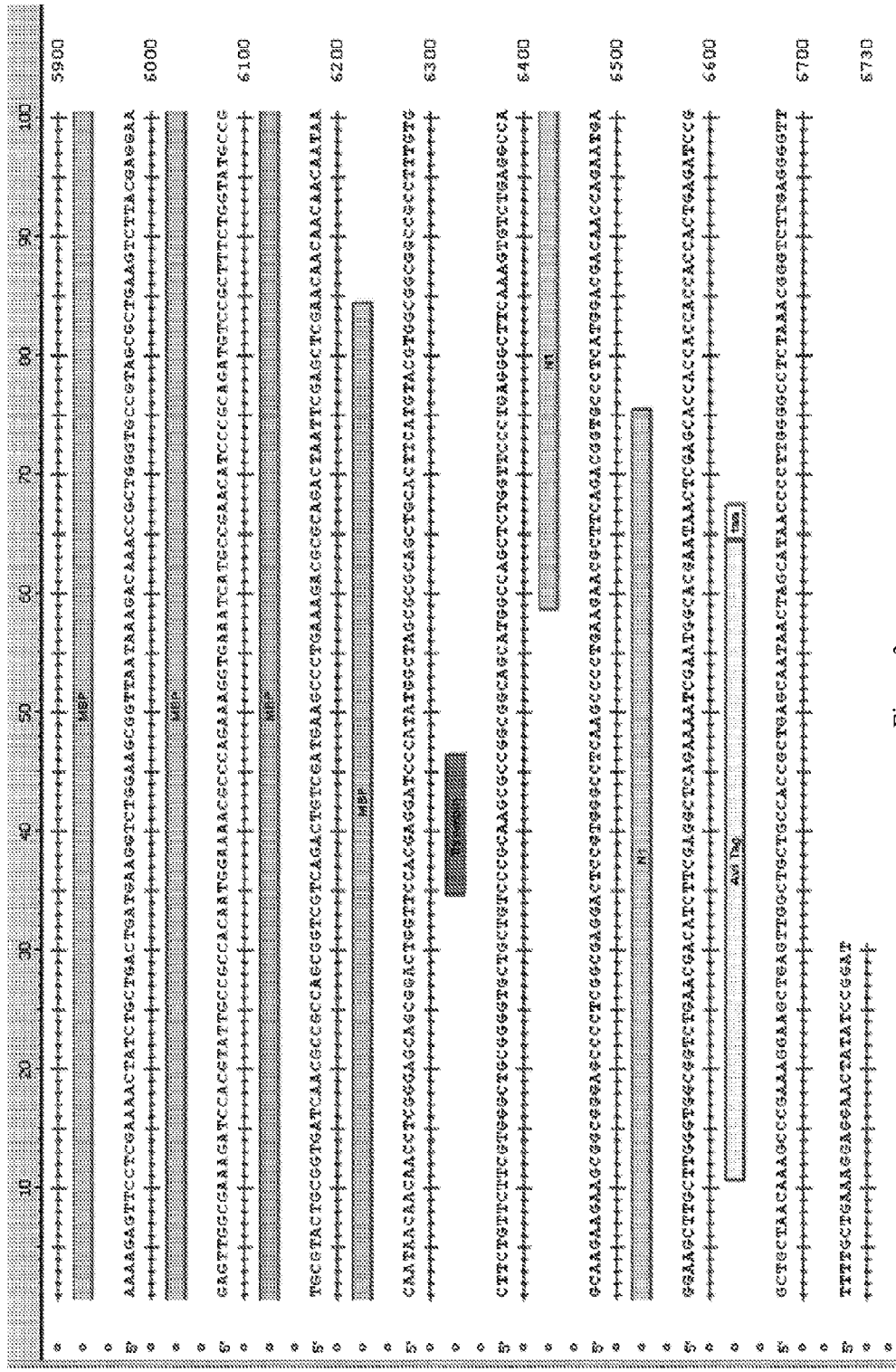
FIG. 3 Nucleotide sequence (SEQ ID NO:4) of MBP-N-1-Sb1 fusion.

A recombinant synthetic substrate based on human Notch 1 called N1-Sb1 was constructed as diagrammed in FIG. 1A. First, a fragment of human Notch1 (residues 1733-1812) was subcloned into the PacS vector that contains an AviTag. AviTag, a specific 15 residue peptide sequence (GLN-DIFEAQKIEWHE (SEQ ID NO:3); Avidity, LLC; U.S. Pat. Nos. 5,723,584, 5,874,239 & 5,932,433) may be biotinylated with biotin ligase on the underlined K. This Notch1-AviTag construct was further subcloned into the pIAD16 vector that contains a chimeric maltose binding protein (MBP)-thrombin target sequence to provide a MBP-thrombin site-Notch fragment-AviTag construct. The MBP facilitates protein purification. The resulting MBP-N1-Sb1 plasmid (FIGS. 2-4) was co-transformed into the BL21 (DE3) *E. coli* strain with the pACYC184 plasmid (BirA) that encodes biotin ligase. IPTG (0.1 mM) and 50 μM of biotin were added to the cell culture to induce protein synthesis and biotinylation of the AviTag sequence. Cells were centrifuged at 8000 g for 30 minutes and the pelleted cells were lysed by passage through a French Press (Spectronics Instruments). The cell homogenate was centrifuged at 17,000 g for 30 minutes. The supernatant was affinity purified on an amylose resin column using the AKTAprimer chromatographic system (Amersham Bioscience). The expression of MBP-tagged N1-Sb1 was identified with SDS-PAGE and the mass was confirmed with LC/MS. MBP was removed from N1-Sb1 with thrombin, as demonstrated by SDS-PAGE and LC/MS (FIG. 1, panels B and C). The P2 substituted N1-Sb1 substrates were generated with Strategene Site-directed Mutagenesis kit, expressed and purified as described for wild-type N1-Sb1. APP recombinant substrate, Sb4, was produced as described previously (Tian et al., 2010, Nat Struct Mol. Biol., 17:151-158).

Cell-Based Notch Cleavage Assay with Western Using ELISA Detection with SM320 Antibody.

HEK293 cells were seeded in a 24-well plate and transfected with either truncated Notch1-ΔE construct (N1-ΔE) (gift from Dr. Raphael Kopan, Washington University School of Medicine, St. Louis, Mo.; (see Supplemental FIG. 1A of van Tetering et al., 2009, J. Biol. Chem., 284:31018-31027, for a diagram of N1-ΔE)) including cmyc (24), or empty pcDNA3.1 (−) (Invitrogen), using Fugene 6 transfection reagents (Roche). N1-ΔE includes the replete intracellular sequence, the transmembrane domain, and a truncated extracellular portion lacking LNR and the EGF repeat sequences (see Supplemental FIG. 1A of van Tetering et al., 2009, J. Biol. Chem., 284:31018-31027). DMSO carrier or 1 μM Compound E were added to the transfected cells, at a final DMSO concentration of 1% (v/v). After 48 hours of treatment, the cells were washed with PBS and lysed with 1×RIPA buffer (50 mM Tris, pH 8.0, 150 mM NaCl, 0.1% (wt/vol) SDS, 1% (vol/vol) Nonidet P-40, and 0.5% (wt/vol) deoxycholic acid). Cell lysates were centrifuged at 13,000×g at 4° C. The cleared supernatant was collected and resolved by SDS-PAGE. The proteins were transferred to PVDF membrane (Millipore) using a semi-dry transfer emit (Bio-Rad) and analyzed by western blot with anti-myc antibody (prepared at Memorial Sloan-Kettering Cancer Center) and SM320 antibody.

Cell-Based Notch Cleavage Assay with Immunostaining Using SM320 Antibody.

HEK293 cells were seeded in a 4-well chamber slide (Lab-tek) and transfected with N1-ΔE as in the preceding paragraph, using Fugene 6 transfection reagents (Roche Applied Science, Mannheim, Germany). Transfected cells were then treated with either DMSO at a 1% final concentration or 1 μM Compound E.

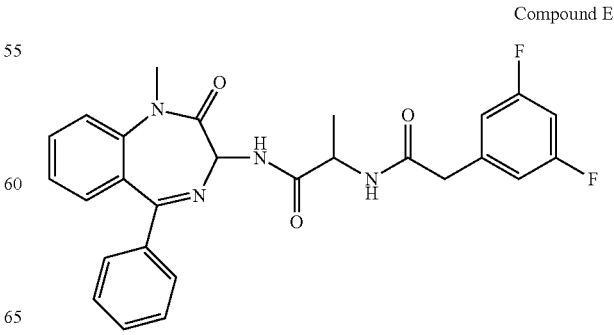

Compound E

After 48 hours of treatment, the cells were washed with PBS, fixed with cold methanol and permeabilized with 0.25% Tween-20. SM320 and anti-myc antibodies were added to detect NICD and full length N1-ΔE, respectively. Alexa Fluor-488 (Invitrogen, San Diego, Calif.) conjugated anti-rabbit and Alexa Fluor-594 (Invitrogen) conjugated anti-mouse antibodies were used as corresponding secondary antibodies. 4',6-diamidino-2-phenylindole (DAPI) was used to stain cell nuclei. Finally, fluorescent images were captured with a Leica TCS Sp2 AOBS laser scanning confocal microscope (Memorial Sloan-Kettering Cancer Center Molecular Cytology Core Facility). Alternatively, REK 293 cells overexpressing N1-ΔE were treated with DMSO or Compound E, and were then collected through centrifugation and embedded in paraffin. The cell pellets were sliced and mounted on glass slides. The immunodetection of NICD was performed at the Molecular Cytology Core Facility of Memorial Sloan Kettering Cancer Center using Discovery XT processor (Ventana Medical Systems). The cell sections were blocked for 30 minutes in 10% normal goat serum in 0.2% BSA/PBS, followed by incubation for 5 h with 0.5 µg/ml of SM320 and incubation for 60 min with biotinylated goat anti-rabbit IgG (Vector labs, cat#:PK6101; 1:200 dilution). The detection was performed with DAB-MAP kit (Ventana Medical Systems). The slides were scanned and digitized using the Mirax Scanner (Carl Zeiss Microsystems).

Cellular Membrane Preparation

HeLa membrane fraction was isolated from HeLa-S3 cells (National Cell Culture Center). The cell pellet was resuspended in Buffer A (50 mM MES, 150 mM KCl, 5 mM $CaCl_2$, 5 mM $MgCl_2$) and lysed by passage through a French Press. N2a cells (murine neuroblastoma cells) over-expressing wild-type PS1, or mutants M146L or E280A, were obtained from Dr. Sangram Sisodia (University of Chicago, Chicago, Ill.). These cells were maintained in 50% Dulbecco's modified Eagle's medium high glucose, 50% Opti-Mem Reduced Serum Media, and 10% fetal calf serum. Cultured cells were pelleted by centrifugation and resuspended in hypotonic buffer (40 mM Tris, pH 7.4, 10 mM NaCl, 1 mM EDTA, and 0.5 mM DTT) for 20 minutes before being lysed with a dounce homogenizer. Nuclear debris from the HeLa and N2a cells were pelleted at 3000 rpm for 30 minutes. The resulting supernatants were ultracentrifuged at 100,000×g for 1 hour. The pellet that contained total cell membrane was resuspended in Buffer A. Mouse brains overexpressing knock-in wild type or M146V PS1 (gift from Dr. Hui Zheng, Amylin Pharmaceuticals, San Diego, Calif.) were homogenized with dounce homogenizer. The cell lysate was centrifuged at 3000 rpm for 30 minutes. The supernatants were ultracentrifuged at 100,000×g for 1 hour. Protein concentration was determined with the DC Protein Assay Kit according to the manufacturer's instructions (Bio-Rad, Hercules, Calif.).

Development of an In Vitro γ-Secretase Assay with N1-Sb1.

An in vitro γ-secretase assay using a novel recombinant APP-derived substrate (termed "Sb4") is disclosed in co-pending application U.S. Ser. No. 12/776,141. In the present assay based on a Notch-derived substrate, N1-Sb1 was incubated with the cell membrane fraction, prepared as described above, in the presence of 0.25% CHAPSO and 1×PIPES buffer (50 mM PIPES, pH 7.0, 150 mM KCl, 5 mM $CaCl_2$, 5 mM $MgCl_2$. The reaction was incubated at 37° C. for 2 hours. The Perkin Elmer AlphaScreen™ detection system was employed to assay for Notch cleavage. AlphaScreen (PerkinElmer Life and Analytical Sciences, Shelton, Conn.) is a bead based non-radioactive Amplified Luminescent Proximity Homogeneous Assay (ALPHA). When a biological interaction brings the beads together, a cascade of chemical reactions acts to produce a greatly amplified signal. Specifically, upon laser excitation, a photosensitizer in the "Donor" bead converts ambient (triplet) oxygen to the more reactive singlet state. The singlet state oxygen molecules diffuse into the solvent, and may react with a thioxene derivative in the Acceptor bead if nearby, generating chemiluminescence at 370 nm that further activates fluorophores contained in the same bead. The fluorophores subsequently emit light at 520-620 nm. In the absence of a specific biological interaction, the singlet state oxygen molecules produced by the donor bead go undetected without the close proximity of the acceptor bead. As a result no fluorescence signal at 520-620 nm is produced.

Figure 5:
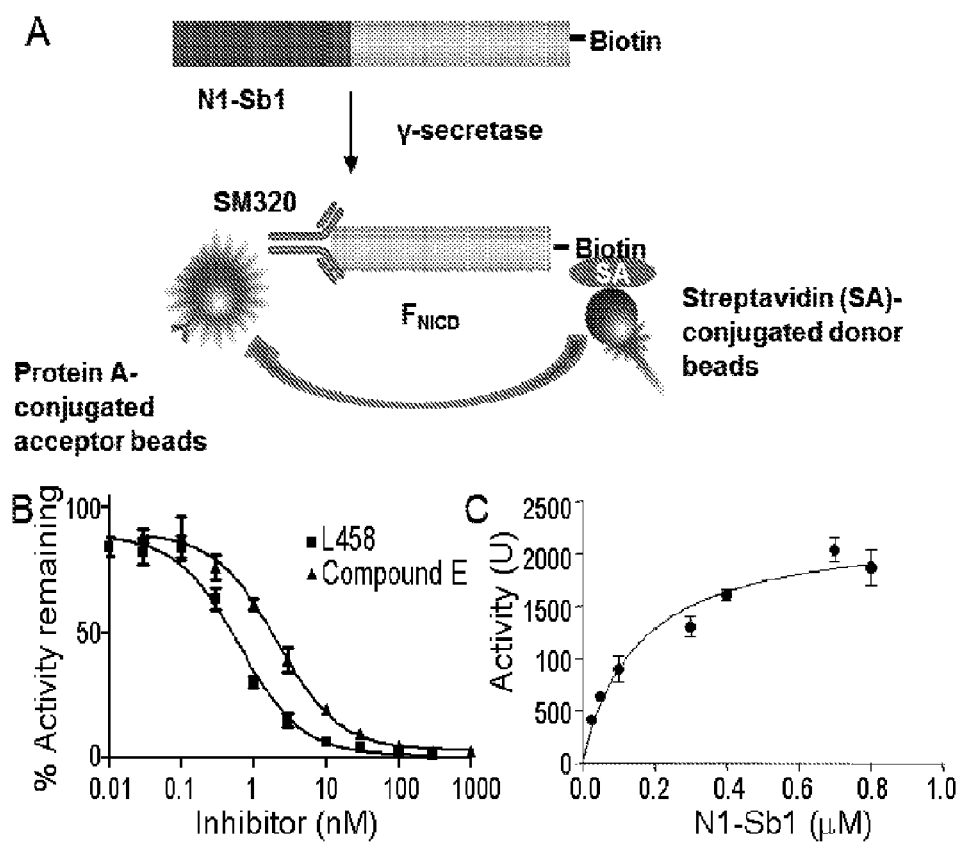
FIG. 5. In vitro N1-Sb1 γ-secretase assay. A. Schematic representation of in vitro γ-secretase assay and detection using the Amplified Luminescent Proximity Homogeneous Assay. B. Inhibitory potency of L685458 and compound E on γ-secretase activity. C. Kinetic analysis of γ-secretase using N1-Sb1 substrate.

In the present system, antibody SM320, Protein A-conjugated acceptor beads, and Streptavidin-conjugated donor beads (PerkinElmer) were added to the reaction at a final concentration of 0.2 µg/ml, 2.5 µg/ml and 5 µg/ml, respectively (diagrammed in FIG. 5A). The reaction was incubated in the dark at room-temperature for 4 hours. The ALPHA signal was detected using the Envision plate reader (Perkin Elmer). The reactions were excited at 680 nm and signal was detected at 615 nm.

Photolabeling Probes and Photolabeling.

Total cell membrane was pre-incubated in the presence of DMSO or 1 µM L458 in PIPES buffer containing 0.25% CHAPSO at 37° C. for 30 minutes. Then, photolabeling probes (JC8, L646 or GY4) (Li et al., 2000, Nature, 405: 689-694, Chun et al., 2004, J Org. Chem., 69:7344-7347, Yang et al., 2009, Bioorg Med Chem. Lett., 19:922-925) at 10 nM were added and incubated for an additional 1 hour at 37° C. The reaction mixtures were irradiated at 350 nm for 45 minutes and solubilize with RIPA buffer. Biotinylated proteins in the soluble fraction were captured by Streptavidin resin (Pierce) overnight at 4° C. Bound proteins were eluted by boiling with SDS sample buffer and analyzed by western blotting with anti-PS1 NTF antibodies.

Example 1

The SM320 Antibody Specifically Recognizes γ-Secretase-Cleaved Notch1 Substrate

The SM320 polyclonal antibody directed against the Notch cleavage product epitope (VLLSRKRRRC) was generated as described in Experimental Methods and its specificity determined. The SM320 antibody was purified by conjugating the epitope peptide to an affinity column and capturing the specific antibody, as described.

Figure 6:
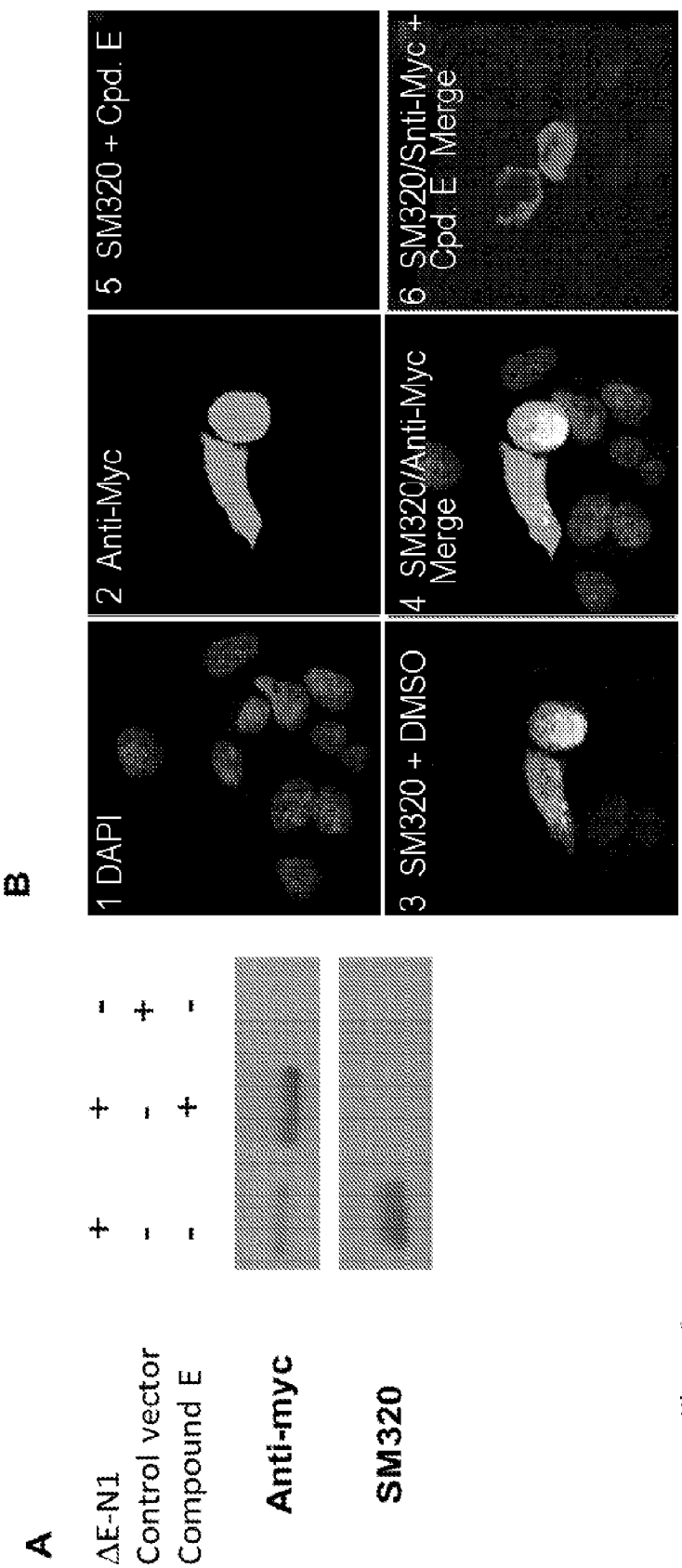
FIG. 6 The SM320 antibody specifically recognizes the γ-secretase cleaved Notch product in Western analysis (A) and immunostaining. (B) The ΔE-Notch1 (a Notch construct with deletion of the extracellular portion) or the control vector was transfected into HEK293 cells in the absence and the presence of γ-secretase inhibitor (L-685,458). The cell lysates were analyzed by Western blot with anti-MYC and SM320 antibody (A). The ΔE-Notch1 transfected cells were fixed, permeablized and stained with DAPI (Deep Blue shapes are visible), anti-Myc/anti mouse-Alexa-fluor 594 (red) and SM321/anti-rabbit-Alexa-fluor 488 (green). B. Panel 4. Merged images (Panels 1-3) in the absence of L-685458. Bright yellow to yello-orange spots are seen in the center, on a background of deep blue shapes. Panel 5. SM320 staining in the presence of L-685458. No spots of any color are observed. Panel 6. Merged images for the L-685,458 treated cells. (No green color was detected. Deep red blotches interspersed with black are visible, on a background of faint deep blue shapes.)

HEK 293 cells were transiently transfected with truncated Notch1-ΔE construct including cmyc (N1-ΔE), a substrate of γ-secretase that is independent of ligand activation, as described in Experimental Methods. Transfected cells were treated with either DMSO vehicle or Compound E, a potent γ-secretase inhibitor. Cell lysates were analyzed by performing SDS-PAGE and immunoblotting the result with anti-myc and SM320 antibody (FIG. 6A). The expression of the myc-tagged N1-ΔE protein was confirmed with anti-myc antibody. N1-ΔE was detected only in cells transfected with this construct (FIG. 6A, upper panel, lanes 1 and 2) but not in the mock transfected cells (FIG. 6A, upper panel, lane 3). More importantly, SM320 detected a specific band that co-migrates with cleaved Notch IntraCellular Domain (NICD) in N1-ΔE transfected cells (FIG. 6A, lower panel, lane 1), but not in the Compound E-treated cells in which γ-secretase activity is expected to be blocked (FIG. 6A, lower panel, lane 2). This western blot analysis confirms that SM320 specifically detects γ-secretase cleaved product, but not the uncleaved substrate.

SM320 was further characterized using immunostaining analysis. The transfected cells were fixed and permeabilized. Following this, N1-ΔE and NICD were immunostained with SM320 and anti-myc antibodies, respectively. Using confocal microscopy, it was shown that N1-ΔE protein, as detected by anti-myc antibody, is expressed in cells transfected with the construct (FIG. 6B, panel 2). SM320 was able to detect NICD only in cells treated with DMSO vehicle (FIG. 6B, panel 3) but not in cells treated with Compound E (FIG. 6B, panel 5). Moreover, the NICD staining co-localized with DAPI staining and thus confirming the translocation of NICD into the nucleus upon γ-secretase cleavage (FIG. 6B, panel 4). Taken together, the western blot and immunostaining analyses established the specificity of antibody SM320 in detecting γ-secretase cleaved Notch product.

Example 2

Development of a Biotinylated Recombinant Notch1 Substrate and an In Vitro γ-Secretase Assay It has been previously demonstrated that biotinylated recombinant APP substrates are suitable for the development of robust γ-secretase assays (21-23; co-pending application U.S. Ser. No. 12/776,141). In order to develop a similar ELISA-like assay based on Notch, an AviTag and a maltose binding protein (MBP)-thrombin cleavage site tag were appended to a Notch1 protein fragment (residues 1733-1812) coding sequence (see Experimental Procedures). The product is designated MBP-N1-Sb1 (FIG. 1A). E. coli cells were co-transformed with this plasmid as well as the pACYC184 plasmid, which encodes biotin ligase, in the presence of biotin. Expression of biotin ligase during induction catalyzes the attachment of biotin to the AviTag. The MBP tag was removed from N1-Sb1 by thrombin cleavage and the product was analyzed by SDS-PAGE and LC-MS. The apparent molecular weight of N1-Sb1 in SDS-PAGE was larger than the expected 12 kDa (FIG. 1B). However, LC-MS showed two species of N1-Sb1: a minor peak at 12017.5 Da and a major peak at 12246.5 Da (FIG. 1C), which match the calculated molecular mass of N1-Sb1 in a non-biotinylated form (12017.7) and biotinylated form (12245.7). Since there is very little non-biotinylated N1-Sb1 (<5%), this suggests a high efficiency of biotin ligation during induction.

HeLa membrane was incubated with N1-Sb1 substrate in the presence of 0.25% CHAPSO. The γ-secretase cleavage product (cN1-Sb1) was detected by the PerkinElmer proximity assay (ALPHA) using the SM320 antibody, Protein A-conjugated acceptor-beads (which bind SM320) and streptavidin-conjugated donor-beads (which bind biotin) (FIG. 5A). cN1-Sb1 levels in DMSO-treated assay was 10-fold higher than in the presence of the inhibitor L-685, 458 (L458; structure shown below)-treated assay. The IC$_{50}$ values of L458 and Compound

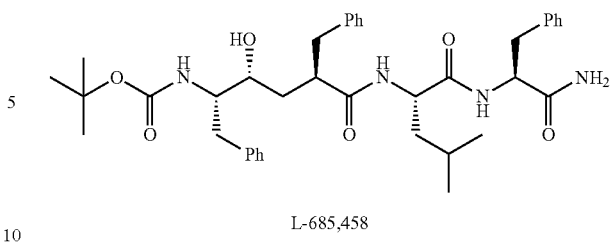

L-685,458

E in inhibiting N1-Sb1 cleavage were also determined The values are 0.7 nM and 1 nM, respectively (FIG. 5B). Finally, we have used this assay to demonstrate that the apparent Km of N1-Sb1 cleavage by γ-secretase is 0.15±0.03 μM and the Vmax is 38 Unit/μg/min (in arbitrary units; FIG. 5C). The above data shows that this in vitro γ-secretase assay is both specific and sensitive, and can be used to assay for γ-secretase cleavage of Notch1.

Example 3

PS1 FAD Mutations have Distinct Effects on Notch1 Cleavage

Figure 7:
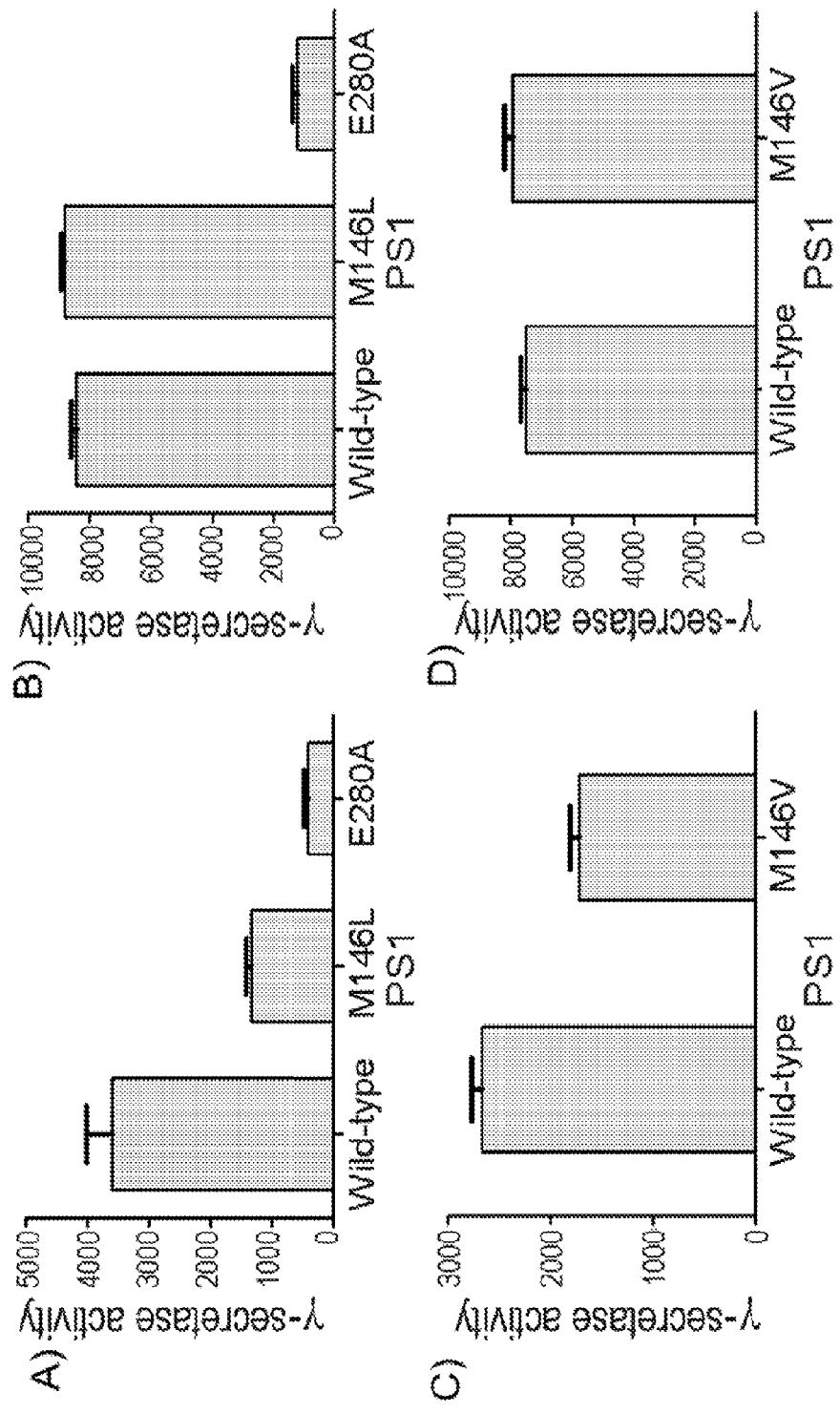
FIG. 7. γ-Secretase activity of various PS1 species. A) N1-Sb1 substrate. B) Sb4 substrate. C) N1-Sb1 substrate. D) Sb4 substrate.

The effects of PS1 FAD mutations on Notch cleavage were determined using the new γ-secretase assay described in Example 2. The activities of two PS1 FAD mutations—PS1 M146L and E280A were compared against wild-type PS1 (WT), which has been previously studied (25). Total membrane was isolated from N2a cells that stably express WT, M146L, or E280A mutants. N1-Sb1 was incubated with these membranes and the resulting cN1-Sb1 was detected with SM320. A significant reduction was observed in N1-Sb1 cleavage by both PS1 FAD mutants compared to the wild-type PS1. The M146L and E280A mutants had 40% and 14% activity remaining, respectively, compared to the activity of the wild type (FIG. 7A). To compare the effects of these two PS1 FAD mutants on APP cleavage, similar experiments were carried out using the APP substrate Sb4 (25) (see co-pending application U.S. Ser. No. 12/776,141). It was found that M146L and wild-type PS1 have similar activity against Sb4 cleavage as determined by the production of Aβ1340 from Sb4 (FIG. 7B). However, PS1 bearing the E280A mutation has 12% activity in the cleavage of Sb4 remaining (FIG. 7B). These data suggest that these two PS1 mutations affect the activity of γ-secretase differentially for Notch or Aβ40 cleavage. The E280A PS1 mutant has a significant loss of function with respect to both Notch1 and Aβ40 cleavages while the M146L PS1 mutant has reduced activity against Notch but not Aβ40 cleavage.

Mouse brain specimens were obtained that either expressed knock-in wild type PS1 or the M146V PS1 mutation (25, 26). Total membrane from these mouse brains was isolated, and the membrane was incubated with N1-Sb1. The cN1-Sb1 cleavage product was detected with the new in-vitro γ-secretase assay of Example 2. It was shown that the M146V PS1 mutant in mouse brain has less activity against Notch cleavage compare to wild-type PS1, whereas this mutation has no effect on Sb4 cleavage. (FIGS. 7C and 7D).

Figure 8:
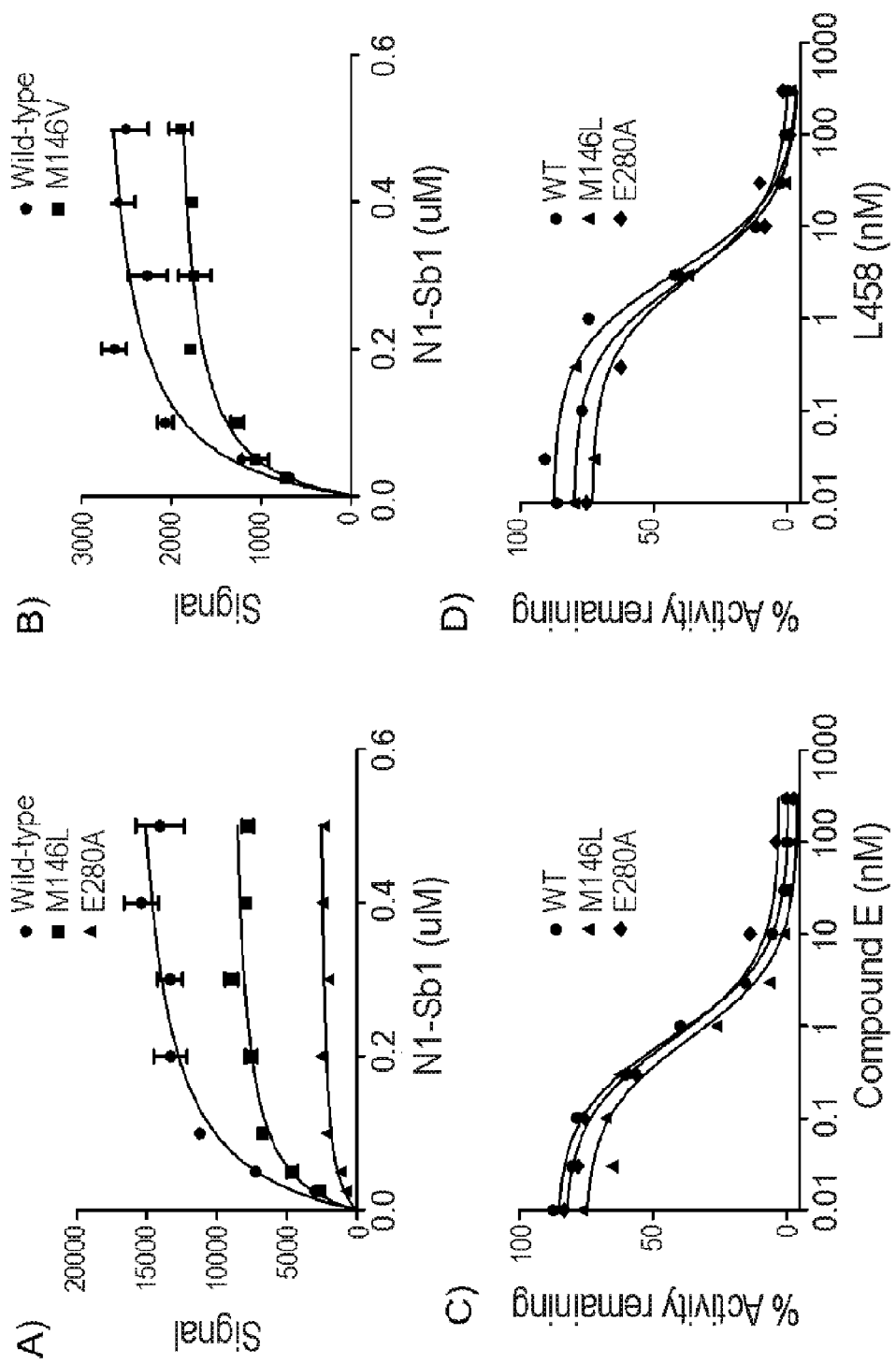
FIG. 8. γ-Secretase activity of various PS1 species. A) Signal intensity for various PS1 species as a function of substrate concentration. B) Signal intensity for various PS1 species in the membrane fraction as a function of substrate concentration. C) Inhibition of γ-secretase by Compound E. D) Inhibition of γ-secretase activity by L-685,458.

Next, the effect of these PS1 mutations on the kinetics of γ-secretase activity for Notch1 cleavage was assessed. The data show that the Km values for N1-Sb1 cleavage by PS1 wild-type, M146L, and E280A FAD mutants are 70, 49, and 50 nM, respectively (FIG. 8A). The Vmax values found for PS1 wild-type, M146L, and E280A FAD mutations are 293, 163 and 49 U/μg/min, respectively. Further, N1-Sb1 was titrated in the presence of membrane fractions isolated from PS1 WT and M146V mouse brain. The Km values of the brain membrane data is consistent with the cell-line data. The Km values of WT and M146V PS1 are 60 and 48 nM, respectively; while the Vmax is 52 and 40 U/μg/min, respectively (FIG. 8B). These data suggest that M146L, M146V and E280A PS1 mutations reduce the Vmax of PS1 against Notch1 cleavage compared to WT PS1.

Further, effects of the FAD mutations on the potencies of γ-secretase inhibitors L458 and Compound E were investigated. It was found that Compound E inhibited wild-type PS1, M146L PS1 and E280A PS1 with similar IC50's of 0.78 nM, 0.76 nM and 0.71 nM, respectively (FIG. 8C); while the IC50's of L458 inhibition are 0.50 nM, 0.45 nM, and 0.46 nM for wild-type PS1, M146L PS1 and E280A PS1, respectively (FIG. 8D). These data suggest that FAD mutations do not alter the potency of γ-secretase inhibitors.

Example 4

Development of a 384- and 1536 Well Format ALPHA-Based γ-Secretase Assay

Figure 9:
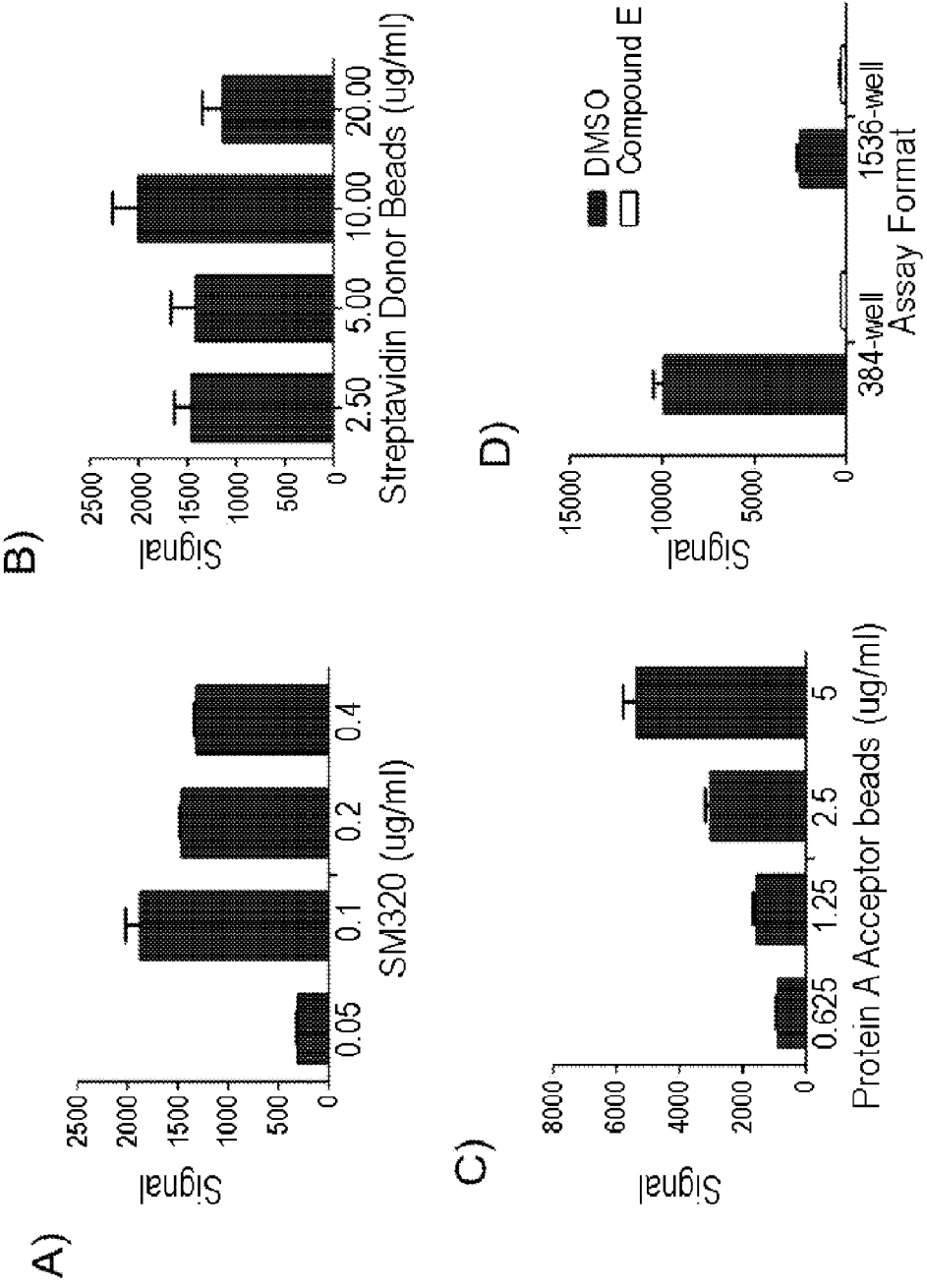
FIG. 9. Dependence of observed of γ-secretase activity on various experimental parameters in an ALPHA assay. A) Dependence on concentration of SM320 antibody. B) Dependence on concentration of streptavidin donor beads. C) Dependence on concentration of protein A acceptor beads. D) Optimized conditions applied to 384 and 1536 well plates.

The 384-well plate assay was optimized by titrating the amount of the SM320 antibody. It was shown that 0.1 ug/ml of SM320 yielded the highest signal (FIG. 9A). Next, the concentrations of Protein A conjugated acceptor beads and streptavidin conjugated donor beads were titrated. Although it was found that streptavidin donor beads at 10 ug/ml has higher signal than 5 ug/ml, there is no significant improvement in the signal to noise ratio (FIG. 9B). It was also shown that 1.25 ug/ml of protein A acceptor beads yielded optimum signal to noise ratio although higher signal can be obtained when higher bead concentrations are used (FIG. 9C). By using 0.1 ug/ml of SM320, 5 ug/ml of streptavidin donor beads and 1.25 ug/ml of protein A acceptor beads in the final 384-well assay conditions, a 25-fold signal to noise ratio was obtained (FIG. 9D).

Based on the 384-well assay format described above, to the assay was miniaturized to a 1536-well format for automated high-throughput drug screening. Concentrations of SM320, protein A conjugated acceptor beads and streptavidin conjugated donor beads were titrated to minimize reagent usage. It was found that 0.05 ug/ml SM320, 0.5 ug/ml Protein A conjugated acceptor beads and 2.5 ug/ml streptavidin conjugated donor beads yielded optimal 7-fold signal to noise ratio (FIG. 9D). The assay was validated by comparing the high and low control signals from full 1536-well plates. The high controls contained 1% final DMSO concentration (v/v), while the low controls contains 250 nM of Compound E also at 1% final DMSO concentration (v/v). The results are in Table 3.

TABLE 3

|  | Average | STDEV | Z' | S/N |
| --- | --- | --- | --- | --- |
| High Control | 2487 | 198 | 0.66 | 7.8 |
| Low Control | 319 | 51 |  |  |

S/N = signal-to-noise.

Example 5

PS1 Mutations Alter the S2 Subpocket of γ-Secretase

Activity-based probes have been widely used to identify and profile various classes of enzymes. L-685,458 (L458), an aspartyl protease transition state mimic that interacts with the active site of γ-secretase (FIG. 10a), has been a valuable tool to study γ-secretase. Therefore, we have generated various potent photoactivatable probes through "photophore walking", in which the photoactivatable benzophenone is separately incorporated into different postions along the peptidomimetic core structure of L458. These positions are also known as the P or P' positions according to Schecter and Berger nomenclature. We intented to apply these L458-based probes to sense the subsite (S and S') conformational change within the active site of γ-secretase caused by PS1 FAD mutations. The rationale of this strategy is that the efficiency of photolabeling by these photoactivatable probes depends on the orientation of the probes and their proximity to residues within the active site. Conformational changes resulting from PS1 mutations within the active site alter the orientation or distance of contact regions with the probes and could lead to different crosslinking efficiencies.

Figure 10:
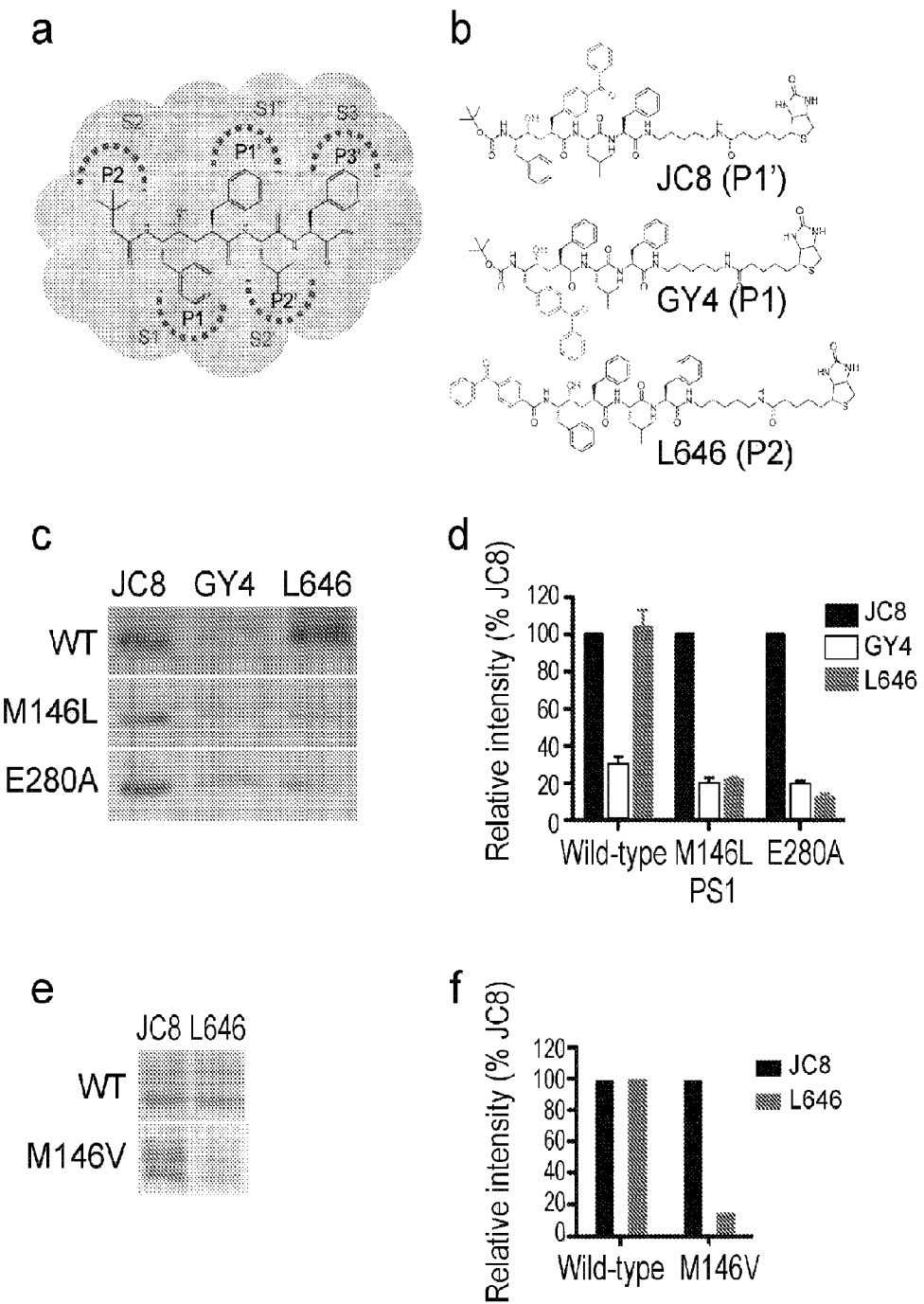
FIG. 10. PS1 mutations alter the S2 subpocket conformation of gamma-secretase. (a) Schematic representation of the interactions between of L458 side chains residues (P/P' positions) with corresponding gamma-secretase subsites (S/S'). (b) Structure of JC8, GY4, and L646, in which a benzophenone was incorporated into the P1', P1 or P2 site of L458, respectively. Biotin was linked to the probes to facilitate isolation of photolabeled proteins. (c) Photolabeling of PS1 NTF with JC8, GY4 and L646. Membranes isolated from WT, M146L, or E280A PS1 stable cell lines were used for this study. (d) The photolabeled PS1 NTF were quantified by comparing the labeling intensities of GY4 and L646 to the labeling intensity of JC8. (e) Analysis of γ-secretase isolated from M146V or WT PS1 from knock-in mouse brains. Photolabeled PS1 was detected with western blot analysis using anti-PS1 NTF antibody. (f) The analyses of photolabeled PS1 NTF were quantified by comparing the labeling intensities of L646 to JC8.

L646, GY4 and JC8, which photolabel the S2, S1, and S1' subsites within the active site of PS1, respectively, were used for this study (FIG. 10b). Membranes isolated from N2a cells stably expressing wild-type (WT), M146L, or E280A PS1 were photolabeled with JC8, GY4 or L646 in the presence of 0.25% CHAPSO. The labeling was determined to be specific because incubating the probes in the presence of excess L458 completely prevented labeling. After ITV irradiation, biotinylated proteins were isolated with streptavidin beads and analyzed by western blotting with anti-PS1 NTF antibodies. First, we showed that JC8, GY4 and L646 all photolabeled WT, M146L, and E280A PS1 NTF (FIG. 10c). To eliminate the effect of various amounts of γ-secretase existing in different cell lines, we normalized each probe with JC8 labeling in the same cell lines. L646 labeled M146L and E280A PS1 NTF with ~80% less intensity than JC8; while L646 was photoinserted into WT PS1 with the same efficiency as JC8 (FIG. 10d). This result strongly indicates that the reduced labeling of PS1 mutants by L646 is not due to decreased expression of γ-secretase in the different stable cell lines, but due to conformational changes within the S2 subsites of M146L and E280A PS1. Finally, we showed that GY4 labeled WT, M146L and E280A PS1 NTF with similar efficiencies (FIGS. 10c and 10d).

To further investigate the effect of PS1 mutations on the active site in an in vivo setting, we performed the same study using M146V and WT PS1 knock-in mouse brains. The M146V PS1 knock-in mice have been well characterized for memory formation and Aβ production. Membrane isolated from the M146V and WT PS1 knock-in mouse brain was labeled with photoprobes JC8 and L646. Similarly, we found that JC8 and L646 labeled WT PS1 with similar intensities (FIGS. 10e and 10f). However, L646 labeled M146V PS1 with 84% less efficiency than JC8 (FIGS. 10e and 10f). This data also showed that M146V PS1 leads to a similar conformation change at the S2 subsite. Taken together, these studies indicate that PS1 FAD mutations directly influence the shape of the active site within the PS1 γ-secretase complex. However, it is still unclear how this change in the S2 subsite of the gamma-secretase active site affects the interaction and catalysis of substrates such as APP and Notch1.

Example 6

PS1 Mutants Prefer N1-Sb1 with Larger P2 Residues

Figure 11:
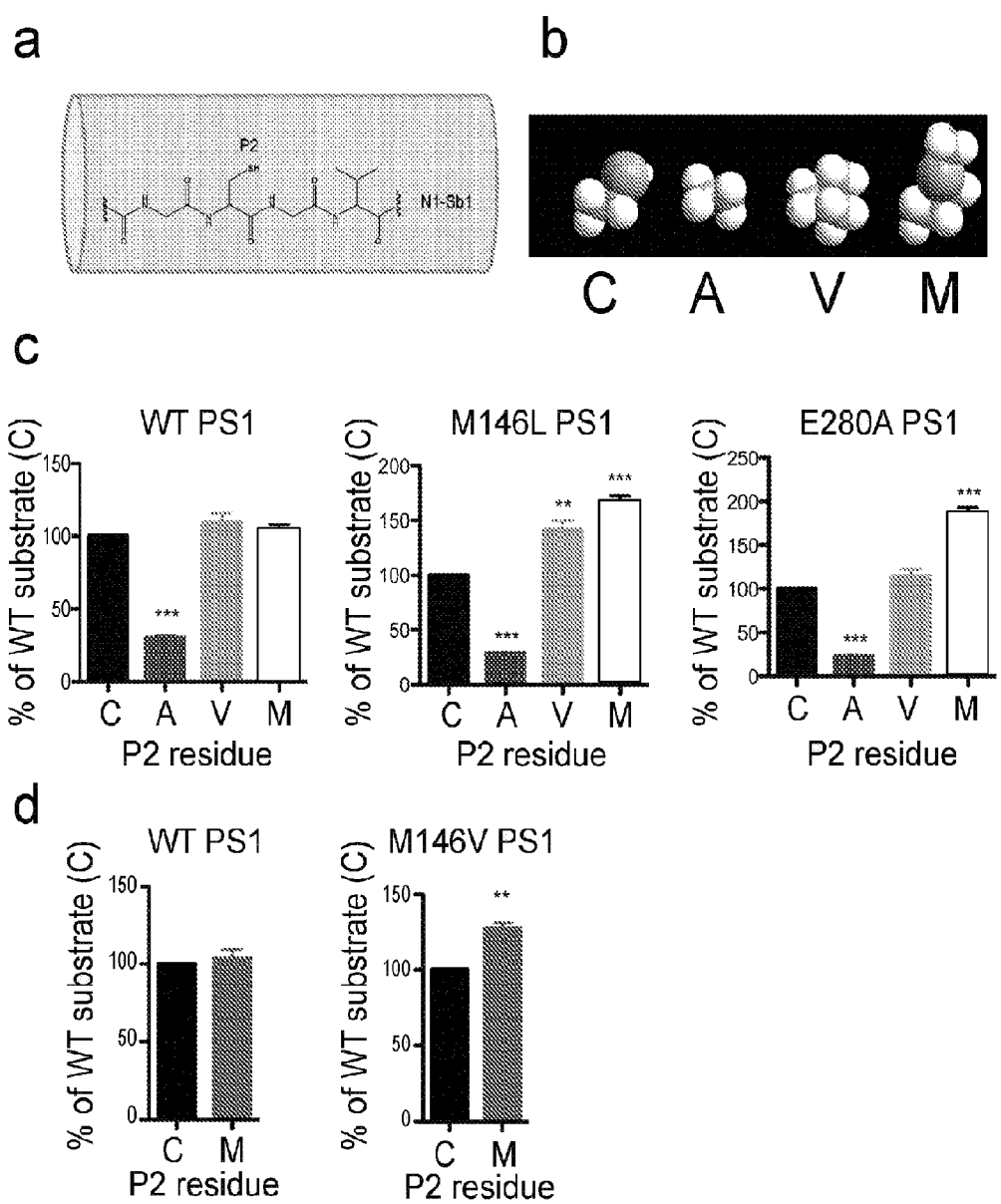
FIG. 11. PS1 mutants preferred N1-Sb1 substrates with a larger P2 residue. (a) Schematic representation of N1-Sb1 with wild-type P2 residue, cysteine. (b) The relative size differences of the wild-type cysteine residue which was substituted with either alanine, valine or methionine are shown. (c) M146L, E280A and WT PS1 from stable cell lines were used to determine the catalysis of or M N1-Sb1. (d) The catalysis of C and M N1-Sb1 were compared between WT and M146V PS1. (n=3, mean+/−s.d. *p<0.001, p<0.01)

Finally, we probed the S2 subsite of the γ-secretase active site with mutated P2 Notch1 substrates. The rationale of this study was to investigate whether larger P2 Notch substrate residues can enhance the activity of PS1 FAD mutants. We generated a series of P2 site mutations corresponding to human Notch1 residue 1752 (Cys) that interacts with the S2 subsite within the gamma-secretase active site (FIG. 11a). We substituted Cys with either Ala, Val, or Met using site-directed mutagenesis (FIG. 11b). After these substrates were purified, we determined the rate of γ-secretase cleavage from each cell membrane against four substrates (FIG. 11c). First, the C1752A substrate had significantly reduced reactivity for all three forms of γ-secretase (20-30% remaining) compared with WT substrate. Secondly, C1752V substrate had considerably increased reactivity for M146L PS1 γ-secretase (141.3±17.9%0 (middle panel) and had no effect on WT (left panel) and E280A PS1 (right panel). Thirdly, C1752M substrate had no effect on WT (left panel), but had significantly enhanced activity for M146L (166.4±6.1%) (middle panel) and E280A (185.5±7.4%) PS1 (right panel). Similarly, we showed that C1752M substrate also had no effect on WT PS1 (left panel), but had enhanced activity for M146V knock-in PS1 (127.4±3.7%) (right panel) (FIG. 11d). Taken together, these data demonstrate that N1-Sb1 with a Met residue at the P2 position is a better substrate for both PS1 mutants, suggesting that Met fits the altered S2 subsites of PS1 mutants better than Cys. On the other hand, N1-Sb1 with a Val at the P2 position is a better substrate for M146L PS1 but not for WT PS1 and E280A PS1, suggesting that the S2 subsite of M146L PS1 is distinguishable from the S2 subsite of E280A PS1. These results indicate that the different PS1 mutations, such as M146L and E280A PS1, can lead to S2 subsite variation, and cause different effects on γ-secretase processing of APP and Notch1.

The data presented here demonstrate that the PS1 mutants, M146L and E280A, directly affect γ-secretase activity, which leads to a reduction in the rate of Notch1 cleavage. However, M146L PS1 has no effect on Aβ40 production and E280A PS1 has reduced Aβ40 production. These studies indicate that PS1 mutations could lead to different effects on APP and Notch1 cleavage. Our in vitro assay offers a unique way to characterize the effects of PS1 mutations on Notch1 and APP cleavage, as well as providing a way to address whether PS1 could contribute to AD through altering the processing of APP and Notch1.

Figure 12:
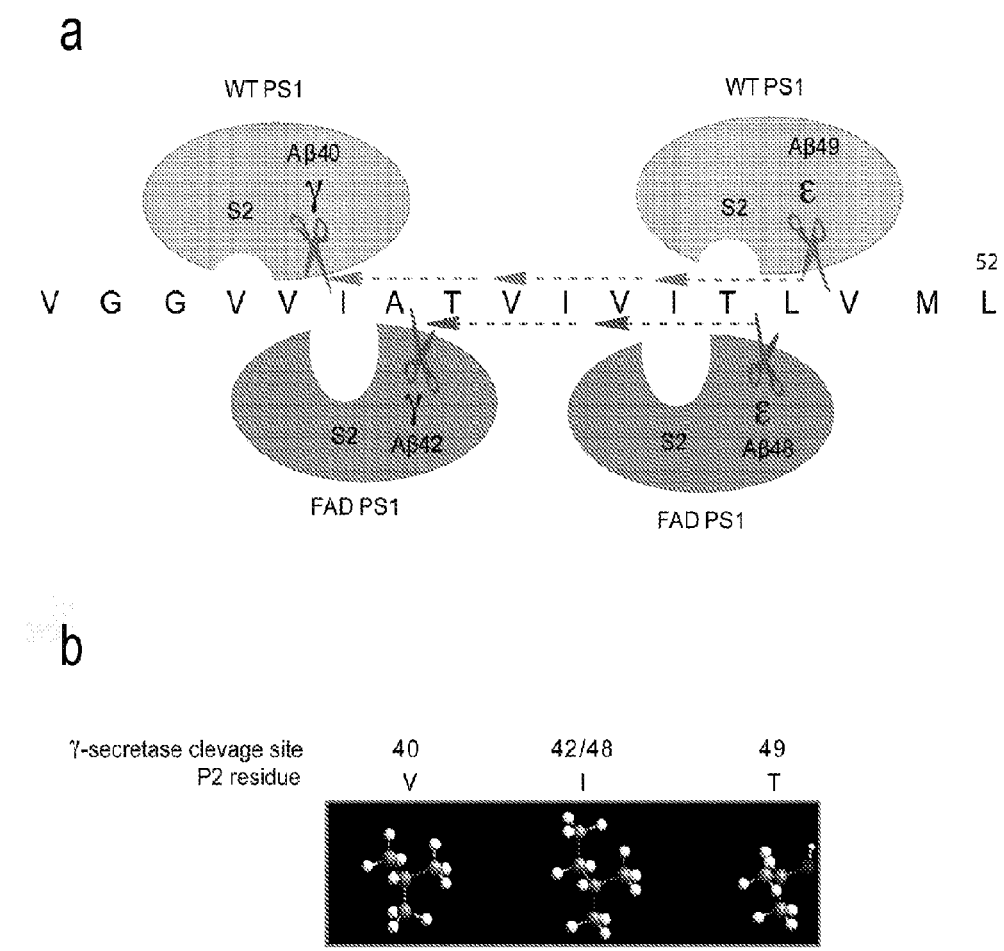
FIG. 12. Schematic representation of WT PS1 and FAD PS1 cleavage of APP. (a) Gamma-Secretase cleaves APP at several positions such as gamma-site, for Aβ40 and Aβ42 production, as well as the ε-site to produce Aβ48 and Aβ49 peptides. The sequential cleavage model proposes that gamma-secretase either first cleaves APP at the Aβ49 site followed by Aβ46, Aβ43 and Aβ40 (green dotted line), or gamma-secretase can cleave APP at the Aβ48 site followed by Aβ45 and Aβ42 (red dotted line). (b) A comparison of the relative sizes of the P2 residues during Aβ40, Aβ42/48 or Aβ49 cleavage. Since augmentation of Aβ42/40 and Aβ48/49 ratio are associated with FAD PS1, this suggests that the deeper S2 subpocket of FAD PS1 prefer Aβ42 and Aβ48 cleavages, which have larger P2 residue (Ile) while WT PS1 that has shallower S2 subsite prefers Aβ40 and Aβ49 cleavage that has smaller P2 residue such as Val and Thr.

Furthermore, our Notch1 substrate P2 residue mutagenesis studies demonstrated that both PS1 mutations, M146L and E280A, lead to similar and yet distinguishable S2 subsite alteration. Although both PS1 mutations prefer Met P2 residue over Cys, M146L and E280A exhibited different activities for Val at the P2 position. Moreover, a smaller residue at the P2 position of Notch1 substrate dramatically reduced its reactivity with γ-secretase. Taken together, these multiple photoaffinity labeling and substrate complement studies indicate that both M146L and E280A mutations lead to a deeper and distinct S2 subsite. This conformational change in the active site could be a plausible mechanism on how PS1 mutations affect •-secretase activity for Aβ40 and Aβ42 production. It has been shown through a sequential cleavage mechanism that Aβ40 and Aβ42 peptides are generated from Aβ49 and Aβ48 peptides, respectively (FIG. 12a). The P2 residues for Aβ40 and Aβ49 cleavages are Val and Thr, respectively (FIG. 12b), which are relatively smaller residues, while the P2 residues for both Aβ42 and Aβ48 are Ile, a larger residue (FIG. 12b). A deeper S2 subsite would favor Aβ48 cleavage, leading to an increase in Aβ42. Concurrently, these changes can affect Aβ49 and Aβ40 cleavages (FIG. 12a). It has been reported that PS1 FAD mutations reduce A1349 production while concomitantly increasing Aβ48 levels, which supports our S2 subsite alteration model (FIG. 12a).

REFERENCES

1. Chan, Y. M., and Jan, Y. N. (1998) *Cell* 94, 423-426.
2. Berezovska, O., Frosch, M., McLean, P., Knowles, R., Koo, E., Kang, D., Shen, J., Lu, F. M., Lux, S. E., Tonegawa, S., and Hyman, B. T. (1999) *Brain Res Mol Brain Res* 69, 273-280.
3. Redmond, L., Oh, S. R., Hicks, C., Weinmaster, G., and Ghosh, A. (2000) *Nat Neurosci* 3, 30-40.
4. Sherrington, R., Rogaev, E. I., Liang, Y., Rogaeva, E. A., Levesque, G., Ikeda, M., Chi, H., Lin, C., Li, G., Holman, K., and et al. (1995) *Nature* 375, 754-760.
5. Levy Lahad, E., Wasco, W., Poorkaj, P., Romano, D. M., Oshima, J., Pettingell, W. H., Yu, C. E., Jondro, P. D., Schmidt, S. D., Wang, K., and et al. (1995) *Science* (New York, N.Y. 269, 973-977.
6. Borchelt, D. R., Thinakaran, G., Eckman, C. B., Lee, M. K., Davenport, F., Ratovitsky, T., Prada, C. M., Kim, G., Seekins, S., Yager, D., Slunt, H. H., Wang, R., Seeger, M., Levey, A. I., Gandy, S. E., Copeland, N. G., Jenkins, N. A., Price, D. L., Younkin, S. G., and Sisodia, S. S. (1996) *Neuron* 17, 1005-1013.
7. Duff, K., Eckman, C., Zehr, C., Yu, X., Prada, C. M., Perez-tur, J., Hutton, M., Buee, L., Harigaya, Y., Yager, D., Morgan, D., Gordon, M. N., Holcomb, L., Refolo, L., Zenk, B., Hardy, J., and Younkin, S. (1996) *Nature* 383, 710-713.
8. Bentahir, M., Nyabi, O., Verhamme, J., Tolia, A., Horre, K., Wiltfang, J., Esselmann, H., and De Strooper, B. (2006) *J Neurochem* 96, 732-742.
9. Song, W., Nadeau, P., Yuan, M., Yang, X., Shen, J., and Yankner, B. A. (1999) *Proceedings of the National Academy of Sciences of the United States of America* 96, 6959-6963.
10. Marambaud, P., Shioi, J., Serban, G., Georgakopoulos, A., Sarner, S., Nagy, V., Bald, L., Wen, P., Efthimiopoulos, S., Shao, Z., Wisniewski, T., and Robakis, N. K. (2002) *The EMBO journal* 21, 1948-1956.
11. Marambaud, P., Wen, P. H., Dutt, A., Shioi, J., Takashima, A., Siman, R., and Robakis, N. K. (2003) *Cell* 114, 635-645.
12. Nakajima, M., Shimizu, T., and Shirasawa, T. (2000) *J Neurosci Res* 62, 311-317.
13. Amtul, Z., Lewis, P. A., Piper, S., Crook, R., Baker, M., Findlay, K., Singleton, A., Hogg, M., Younkin, L., Younkin, S. G., Hardy, J., Hutton, M., Boeve, B. F., Tang-Wai, D., and Golde, T. E. (2002) *Neurobiol Dis* 9, 269-273.
14. Chen, F., Gu, Y., Hasegawa, H., Ruan, X., Arawaka, S., Fraser, P., Westaway, D., Mount, H., and St George-Hyslop, P. (2002) *The Journal of biological chemistry* 277, 36521-36526.
15. Moehlmann, T., Winkler, E., Xia, X., Edbauer, D., Murrell, J., Capell, A., Kaether, C., Zheng, H., Ghetti, B., HaRss, C., and Steiner, H. (2002) *Proceedings of the National Academy of Sciences of the United States of America* 99, 8025-8030.
16. Gandy, S., Zhang, Y. W., Ikin, A., Schmidt, S. D., Bogush, A., Levy, E., Sheffield, R., Nixon, R. A., Liao, F. F., Mathews, P. M., Xu, H., and Ehrlich, M. E. (2007) *J Neurochem* 102, 619-626.
17. Lee, M. K., Borchelt, D. R., Kim, G., Thinakaran, G., Slunt, H. H., Ratovitski, T., Martin, L. J., Kittur, A., Gandy, S., Levey, A. I., Jenkins, N., Copeland, N., Price, D. L., and Sisodia, S. S. (1997) *Nature medicine* 3, 756-760.
18. Murayama, O., Murayama, M., Honda, T., Sun, X., Nihonmatsu, N., and Takashima, A. (1999) *Prog Neuropsychopharmacol Biol Psychiatry* 23, 905-913.
19. Esler, W. P., Kimberly, W. T., Ostaszewski, B. L., Ye, W., Diehl, T. S., Selkoe, D. J., and Wolfe, M. S. (2002) *Proceedings of the National Academy of Sciences of the United States of America* 99, 2720-2725.
20. Keller, P. C., 2nd, Tomita, T., Hayashi, I., Chandu, D., Weber, J. D., Cistola, D. P., and Kopan, R. (2006) *Biochemistry* 45, 5351-5358.
21. Shelton, C. C., Tian, Y., Frattini, M. G., and Li, Y. M. (2009) *Mol Neurodegener* 4, 22
22. Shelton, C. C., Tian, Y., Shum, D., Radu, C., Djaballah, H., and Li, Y. M. (2009) *Assay Drug Dev Technol*.
23. Tian, Y., Bassit, B., Chau, D., and Li, Y. M. (2010) *Nat Struct Mol Biol* xx-xx.
24. van Tetering, G., van Diest, P., Verlaan, I., van der Wall, E., Kopan, R, and Vooijs, M. (2009) *J. Biol. Chemistry*, 284, 31018-31027.
25. Placanica L, Zhu L, Li Y-M (2009) PLoS ONE 4(4): e5088; doi:10.1371/journal.pone. 0005088.
26. Wang, R, Wang, B, He, W and Zheng, H (2006) *J. Biol. Chem.* 281, 15330-15336.
27. Placania, L., et al., (2009) *J Biol Chem* 284, 2967-77.
28. Cravatt, B. F., Wright, A. T. & Kozarich, J. W. Activity-based protein profiling: from enzyme chemistry to proteomic chemistry. *Annu Rev Biochem* 77, 383-414 (2008).
29. Li, Y. M. et al. Nature 405, 689-94 (2000).
30. Shelton, C. C. et al, *Proc Natl Acad Sci USA* 106, 20228-33 (2009).
31. Schechter, I. & Berger, A. *Biochem Biophys Res Commun* 27, 157-62 (1967).
32. Wang, R., Dineley, K. T., Sweatt, J. D. & Zheng, H. *Neuroscience* 126, 305-12 (2004).
33. Wang, R., Wang, B., He, W. & Zheng, H. *J Biol Chem* 281, 15330-6 (2006).
34. Takami, M. et al., *J Neurosci* 29, 13042-52 (2009).
37. Sato, T. et al. *J Biol Chem* 278, 24294-301 (2003).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of assaying the activity of γ-secretase comprising:
   providing a composition suspected of containing γ-secretase activity;
   contacting the composition with a polypeptide substrate for γ-secretase comprising a Notch substrate, wherein the Notch substrate comprises a fragment of a Notch protein, wherein the fragment comprises an amino acid sequence consisting of SEQ ID NO:6, SEQ ID NO:7, SEQ ID NO:9, SEQ ID NO: 10, or SEQ ID NO: 13, wherein the fragment comprises an S3 cleavage site and an amino acid sequence VLLSRKRRR (SEQ ID NO:2) adjacent to the S3 cleavage site and wherein the fragment comprises an amino acid sequence bound to a biotin label located on the C-terminal side of the S3 site, and wherein γ-secretase cleaves the Notch substrate at the S3 cleavage site to provide a detectably labeled product comprising an amino acid sequence having the biotin at the C-terminal side and the sequence VLLSRKRRR (SEQ ID NO: 2) at the N-terminal side that is specifically recognized by a second antibody;
   contacting the detectably labeled product with
   a first ligand comprising a first tag wherein the first ligand specifically binds the biotin label of the detectably labeled product, and
   the second antibody comprising a second tag wherein the second antibody specifically binds the VLLSRKRRR (SEQ ID NO: 2) epitope at the N-terminal side of the detectably labeled product, wherein the second antibody is raised against the polypeptide sequence VLLSRKRRR (SEQ ID NO:2) and the second antibody binds the γ-secretase cleaved detectably labeled product but not the uncleaved notch substrate; and determining the presence, the amount, or the combination thereof of the detectably labeled product bound to the first ligand and to the second antibody.

2. The method of claim 1 wherein the contacting occurs in a container.

3. The method of claim 2 wherein the method is a high throughput assay method conducted in a plurality of containers.

4. The method of claim 3 wherein each container is a well in a multi-well assay plate, thereby providing a high throughput method of assaying.

5. The method of claim 1 wherein the first ligand comprises avidin and the first tag comprises a detectable fluorescence acceptor.

6. The method of claim 5 wherein the second antibody specifically binds the Notch substrate after cleavage by the γ-secretase and does not specifically bind the Notch substrate before cleavage by the γ-secretase, the second antibody being bound to a third antibody bearing a fluorescence donor that excites the fluorescence acceptor tag bound to the first ligand.

7. A method of assaying the activity of γ-secretase in a cell comprising:
providing cells suspected of harboring γ-secretase activity;
contacting the cells with media comprising a polypeptide substrate for γ-secretase wherein the substrate comprises a Notch substrate, wherein cleavage of the Notch substrate by the γ-secretase provides a detectably labeled product, wherein the Notch substrate comprises a fragment of a Notch protein, wherein the fragment comprises an amino acid sequence consisting of SEQ ID NO:6, SEQ ID NO:7, SEQ ID NO:9, SEQ ID NO:10, or SEQ ID NO:13, wherein the fragment comprises an S3 cleavage site and an amino acid sequence VLLSRKRRR (SEQ ID NO:2) adjacent to the S3 cleavage site and wherein the fragment comprises an amino acid sequence bound to a biotin label located on the C-terminal side of the S3 cleavage site; wherein the γ-secretase cleaves the Notch substrate at the S3 cleavage site to provide the detectably labeled product comprising an amino acid sequence having the biotin at the C-terminal side and the sequence VLLSRKRRR (SEQ ID NO: 2) at the N-terminal side that is specifically recognized by a second antibody raised using the polypeptide VLLSRKRR (SEQ ID NO: 2) and the second antibody binds the γ-secretase cleaved detectably labeled product but not the uncleaved notch substrate; and
determining the presence of the detectably labeled product using a first ligand that specifically binds the biotin and the second antibody.

8. The method of claim 7 wherein the determining comprises:
separating the cells from the media after a suitable incubation period with the polypeptide substrate for γ-secretase to provide a supernatant; and determining the presence of the detectably labeled product in the supernatant.

9. The method of claim 8 wherein the determining the presence of the detectably labeled product comprises:
contacting the detectably labeled product with
the first ligand comprising a first tag wherein the first ligand specifically binds the biotin label, and
the second antibody comprising a second tag; and
determining the presence, the amount, or the combination thereof of the labeled product bound to the first ligand and to the second antibody.

10. The method of claim 7 wherein the media further comprises a detergent.

11. The method of claim 9, wherein the first tag comprises a detectable probe.

12. The method of claim 11 wherein the detectable probe comprises ruthenium.

13. The method of claim 7 wherein the contacting occurs in a container.

14. The method of claim 13 wherein the method is a high throughput assay method conducted in a plurality of containers.

15. The method of claim 14 wherein each container is a well in a multi-well assay plate, thereby providing a high throughput method of assaying.

16. The method of claim 9 wherein the first ligand comprises avidin and the first tag comprises a detectable fluorescence acceptor.

17. The method of claim 1 wherein the fragment of the Notch protein consists of the amino acid sequence SEQ ID NO:6, SEQ ID NO:7, SEQ ID NO:9, SEQ ID NO:10, or SEQ ID NO:13.

18. The method of claim 7 wherein the fragment of the Notch protein consists of the amino acid sequence SEQ ID NO:6, SEQ ID NO:7, SEQ ID NO:9, SEQ ID NO:10, or SEQ ID NO:13.

* * * * *

SEQUENCE LISTING

```
<160> NUMBER OF SEQ ID NOS: 14

<210> SEQ ID NO 1
<211> LENGTH: 2556
<212> TYPE: PRT
<213> ORGANISM: Homo sapiens
<220> FEATURE:
<221> NAME/KEY: misc_feature
<222> LOCATION: (891)..(891)
<223> OTHER INFORMATION: Xaa can be any naturally occurring amino acid

<400> SEQUENCE: 1

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
```

```
                50              55              60
Ser Thr Pro Cys Lys Asn Ala Gly Thr Cys His Val Asp Arg Arg
65              70              75              80

Gly Val Ala Asp Tyr Ala Cys Ser Cys Ala Leu Gly Phe Ser Gly Pro
                85              90              95

Leu Cys Leu Thr Pro Leu Asp Asn Ala Cys Leu Thr Asn Pro Cys Arg
            100             105             110

Asn Gly Gly Thr Cys Asp Leu Leu Thr Leu Thr Glu Tyr Lys Cys Arg
            115             120             125

Cys Pro Pro Gly Trp Ser Gly Lys Ser Cys Gln Gln Ala Asp Pro Cys
        130             135             140

Ala Ser Asn Pro Cys Ala Asn Gly Gly Gln Cys Leu Pro Phe Glu Ala
145             150             155             160

Ser Tyr Ile Cys His Cys Pro Pro Ser Phe His Gly Pro Thr Cys Arg
                165             170             175

Gln Asp Val Asn Glu Cys Gly Gln Lys Pro Arg Leu Cys Arg His Gly
            180             185             190

Gly Thr Cys His Asn Glu Val Gly Ser Tyr Arg Cys Val Cys Arg Ala
        195             200             205

Thr His Thr Gly Pro Asn Cys Glu Arg Pro Tyr Val Pro Cys Ser Pro
210             215             220

Ser Pro Cys Gln Asn Gly Gly Thr Cys Arg Pro Thr Gly Asp Val Thr
225             230             235             240

His Glu Cys Ala Cys Leu Pro Gly Phe Thr Gly Gln Asn Cys Glu Glu
                245             250             255

Asn Ile Asp Asp Cys Pro Gly Asn Asn Cys Lys Asn Gly Gly Ala Cys
            260             265             270

Val Asp Gly Val Asn Thr Tyr Asn Cys Pro Cys Pro Pro Glu Trp Thr
        275             280             285

Gly Gln Tyr Cys Thr Glu Asp Val Asp Glu Cys Gln Leu Met Pro Asn
    290             295             300

Ala Cys Gln Asn Gly Gly Thr Cys His Asn Thr His Gly Gly Tyr Asn
305             310             315             320

Cys Val Cys Val Asn Gly Trp Thr Gly Glu Asp Cys Ser Glu Asn Ile
                325             330             335

Asp Asp Cys Ala Ser Ala Ala Cys Phe His Gly Ala Thr Cys His Asp
            340             345             350

Arg Val Ala Ser Phe Tyr Cys Glu Cys Pro His Gly Arg Thr Gly Leu
        355             360             365

Leu Cys His Leu Asn Asp Ala Cys Ile Ser Asn Pro Cys Asn Glu Gly
    370             375             380

Ser Asn Cys Asp Thr Asn Pro Val Asn Gly Lys Ala Ile Cys Thr Cys
385             390             395             400

Pro Ser Gly Tyr Thr Gly Pro Ala Cys Ser Gln Asp Val Asp Glu Cys
            405             410             415

Ser Leu Gly Ala Asn Pro Cys Glu His Ala Gly Lys Cys Ile Asn Thr
        420             425             430

Leu Gly Ser Phe Glu Cys Gln Cys Leu Gln Gly Tyr Thr Gly Pro Arg
    435             440             445

Cys Glu Ile Asp Val Asn Glu Cys Val Ser Asn Pro Cys Gln Asn Asp
450             455             460

Ala Thr Cys Leu Asp Gln Ile Gly Glu Phe Gln Cys Met Cys Met Pro
465             470             475             480
```

```
Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
            515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
            595                 600                 605

Ser Gln Pro Cys Arg Leu Arg Gly Thr Cys Gln Asp Pro Asp Asn Ala
            610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ser Asn Ile Asp Glu Cys Ala Gly Asn Pro Cys His
            675                 680                 685

Asn Gly Gly Thr Cys Glu Asp Gly Ile Asn Gly Phe Thr Cys Arg Cys
690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
            755                 760                 765

Lys Asp Met Thr Ser Gly Ile Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Lys Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
            835                 840                 845

Asp Tyr Glu Ser Phe Ser Cys Val Cys Pro Thr Ala Gly Ala Lys Gly
    850                 855                 860

Gln Thr Cys Glu Val Asp Ile Asn Glu Cys Val Leu Ser Pro Cys Arg
865                 870                 875                 880

His Gly Ala Ser Cys Gln Asn Thr His Gly Xaa Tyr Arg Cys His Cys
                885                 890                 895
```

-continued

```
Gln Ala Gly Tyr Ser Gly Arg Asn Cys Glu Thr Asp Ile Asp Cys
            900                 905                 910
Arg Pro Asn Pro Cys His Asn Gly Gly Ser Cys Thr Asp Gly Ile Asn
        915                 920                 925
Thr Ala Phe Cys Asp Cys Leu Pro Gly Phe Arg Gly Thr Phe Cys Glu
        930                 935                 940
Glu Asp Ile Asn Glu Cys Ala Ser Asp Pro Cys Arg Asn Gly Ala Asn
945                 950                 955                 960
Cys Thr Asp Cys Val Asp Ser Tyr Thr Cys Thr Cys Pro Ala Gly Phe
                965                 970                 975
Ser Gly Ile His Cys Glu Asn Asn Thr Pro Asp Cys Thr Glu Ser Ser
            980                 985                 990
Cys Phe Asn Gly Gly Thr Cys Val Asp Gly Ile Asn Ser Phe Thr Cys
        995                 1000                1005
Leu Cys Pro Pro Gly Phe Thr Gly Ser Tyr Cys Gln His Val Val
        1010                1015                1020
Asn Glu Cys Asp Ser Arg Pro Cys Leu Leu Gly Gly Thr Cys Gln
        1025                1030                1035
Asp Gly Arg Gly Leu His Arg Cys Thr Cys Pro Gln Gly Tyr Thr
        1040                1045                1050
Gly Pro Asn Cys Gln Asn Leu Val His Trp Cys Asp Ser Ser Pro
        1055                1060                1065
Cys Lys Asn Gly Gly Lys Cys Trp Gln Thr His Thr Gln Tyr Arg
        1070                1075                1080
Cys Glu Cys Pro Ser Gly Trp Thr Gly Leu Tyr Cys Asp Val Pro
        1085                1090                1095
Ser Val Ser Cys Glu Val Ala Ala Gln Arg Gln Gly Val Asp Val
        1100                1105                1110
Ala Arg Leu Cys Gln His Gly Gly Leu Cys Val Asp Ala Gly Asn
        1115                1120                1125
Thr His His Cys Arg Cys Gln Ala Gly Tyr Thr Gly Ser Tyr Cys
        1130                1135                1140
Glu Asp Leu Val Asp Glu Cys Ser Pro Ser Pro Cys Gln Asn Gly
        1145                1150                1155
Ala Thr Cys Thr Asp Tyr Leu Gly Gly Tyr Ser Cys Lys Cys Val
        1160                1165                1170
Ala Gly Tyr His Gly Val Asn Cys Ser Glu Glu Ile Asp Glu Cys
        1175                1180                1185
Leu Ser His Pro Cys Gln Asn Gly Gly Thr Cys Leu Asp Leu Pro
        1190                1195                1200
Asn Thr Tyr Lys Cys Ser Cys Pro Arg Gly Thr Gln Gly Val His
        1205                1210                1215
Cys Glu Ile Asn Val Asp Asp Cys Asn Pro Pro Val Asp Pro Val
        1220                1225                1230
Ser Arg Ser Pro Lys Cys Phe Asn Asn Gly Thr Cys Val Asp Gln
        1235                1240                1245
Val Gly Gly Tyr Ser Cys Thr Cys Pro Pro Gly Phe Val Gly Glu
        1250                1255                1260
Arg Cys Glu Gly Asp Val Asn Glu Cys Leu Ser Asn Pro Cys Asp
        1265                1270                1275
Ala Arg Gly Thr Gln Asn Cys Val Gln Arg Val Asn Asp Phe His
        1280                1285                1290
Cys Glu Cys Arg Ala Gly His Thr Gly Arg Arg Cys Glu Ser Val
```

```
              1295                1300                1305
Ile Asn Gly Cys Lys Gly Lys Pro Cys Lys Asn Gly Gly Thr Cys
    1310                1315                1320

Ala Val Ala Ser Asn Thr Ala Arg Gly Phe Ile Cys Lys Cys Pro
    1325                1330                1335

Ala Gly Phe Glu Gly Ala Thr Cys Glu Asn Asp Ala Arg Thr Cys
    1340                1345                1350

Gly Ser Leu Arg Cys Leu Asn Gly Gly Thr Cys Ile Ser Gly Pro
    1355                1360                1365

Arg Ser Pro Thr Cys Leu Cys Leu Gly Pro Phe Thr Gly Pro Glu
    1370                1375                1380

Cys Gln Phe Pro Ala Ser Ser Pro Cys Leu Gly Gly Asn Pro Cys
    1385                1390                1395

Tyr Asn Gln Gly Thr Cys Glu Pro Thr Ser Glu Ser Pro Phe Tyr
    1400                1405                1410

Arg Cys Leu Cys Pro Ala Lys Phe Asn Gly Leu Leu Cys His Ile
    1415                1420                1425

Leu Asp Tyr Ser Phe Gly Gly Gly Ala Gly Arg Asp Ile Pro Pro
    1430                1435                1440

Pro Leu Ile Glu Glu Ala Cys Glu Leu Pro Glu Cys Gln Glu Asp
    1445                1450                1455

Ala Gly Asn Lys Val Cys Ser Leu Gln Cys Asn Asn His Ala Cys
    1460                1465                1470

Gly Trp Asp Gly Gly Asp Cys Ser Leu Asn Phe Asn Asp Pro Trp
    1475                1480                1485

Lys Asn Cys Thr Gln Ser Leu Gln Cys Trp Lys Tyr Phe Ser Asp
    1490                1495                1500

Gly His Cys Asp Ser Gln Cys Asn Ser Ala Gly Cys Leu Phe Asp
    1505                1510                1515

Gly Phe Asp Cys Gln Arg Ala Glu Gly Gln Cys Asn Pro Leu Tyr
    1520                1525                1530

Asp Gln Tyr Cys Lys Asp His Phe Ser Asp Gly His Cys Asp Gln
    1535                1540                1545

Gly Cys Asn Ser Ala Glu Cys Glu Trp Asp Gly Leu Asp Cys Ala
    1550                1555                1560

Glu His Val Pro Glu Arg Leu Ala Ala Gly Thr Leu Val Val Val
    1565                1570                1575

Val Leu Met Pro Pro Glu Gln Leu Arg Asn Ser Ser Phe His Phe
    1580                1585                1590

Leu Arg Glu Leu Ser Arg Val Leu His Thr Asn Val Val Phe Lys
    1595                1600                1605

Arg Asp Ala His Gly Gln Gln Met Ile Phe Pro Tyr Tyr Gly Arg
    1610                1615                1620

Glu Glu Glu Leu Arg Lys His Pro Ile Lys Arg Ala Ala Glu Gly
    1625                1630                1635

Trp Ala Ala Pro Asp Ala Leu Leu Gly Gln Val Lys Ala Ser Leu
    1640                1645                1650

Leu Pro Gly Gly Ser Glu Gly Gly Arg Arg Arg Arg Glu Leu Asp
    1655                1660                1665

Pro Met Asp Val Arg Gly Ser Ile Val Tyr Leu Glu Ile Asp Asn
    1670                1675                1680

Arg Gln Cys Val Gln Ala Ser Ser Gln Cys Phe Gln Ser Ala Thr
    1685                1690                1695
```

```
Asp Val Ala Ala Phe Leu Gly Ala Leu Ala Ser Leu Gly Ser Leu
    1700                1705                1710

Asn Ile Pro Tyr Lys Ile Glu Ala Val Gln Ser Glu Thr Val Glu
    1715                1720                1725

Pro Pro Pro Pro Ala Gln Leu His Phe Met Tyr Val Ala Ala Ala
    1730                1735                1740

Ala Phe Val Leu Leu Phe Phe Val Gly Cys Gly Val Leu Leu Ser
    1745                1750                1755

Arg Lys Arg Arg Arg Gln His Gly Gln Leu Trp Phe Pro Glu Gly
    1760                1765                1770

Phe Lys Val Ser Glu Ala Ser Lys Lys Lys Arg Arg Glu Pro Leu
    1775                1780                1785

Gly Glu Asp Ser Val Gly Leu Lys Pro Leu Lys Asn Ala Ser Asp
    1790                1795                1800

Gly Ala Leu Met Asp Asp Asn Gln Asn Glu Trp Gly Asp Glu Asp
    1805                1810                1815

Leu Glu Thr Lys Lys Phe Arg Phe Glu Glu Pro Val Val Leu Pro
    1820                1825                1830

Asp Leu Asp Asp Gln Thr Asp His Arg Gln Trp Thr Gln Gln His
    1835                1840                1845

Leu Asp Ala Ala Asp Leu Arg Met Ser Ala Met Ala Pro Thr Pro
    1850                1855                1860

Pro Gln Gly Glu Val Asp Ala Asp Cys Met Asp Val Asn Val Arg
    1865                1870                1875

Gly Pro Asp Gly Phe Thr Pro Leu Met Ile Ala Ser Cys Ser Gly
    1880                1885                1890

Gly Gly Leu Glu Thr Gly Asn Ser Glu Glu Glu Glu Asp Ala Pro
    1895                1900                1905

Ala Val Ile Ser Asp Phe Ile Tyr Gln Gly Ala Ser Leu His Asn
    1910                1915                1920

Gln Thr Asp Arg Thr Gly Glu Thr Ala Leu His Leu Ala Ala Arg
    1925                1930                1935

Tyr Ser Arg Ser Asp Ala Ala Lys Arg Leu Leu Glu Ala Ser Ala
    1940                1945                1950

Asp Ala Asn Ile Gln Asp Asn Met Gly Arg Thr Pro Leu His Ala
    1955                1960                1965

Ala Val Ser Ala Asp Ala Gln Gly Val Phe Gln Ile Leu Ile Arg
    1970                1975                1980

Asn Arg Ala Thr Asp Leu Asp Ala Arg Met His Asp Gly Thr Thr
    1985                1990                1995

Pro Leu Ile Leu Ala Ala Arg Leu Ala Val Glu Gly Met Leu Glu
    2000                2005                2010

Asp Leu Ile Asn Ser His Ala Asp Val Asn Ala Val Asp Asp Leu
    2015                2020                2025

Gly Lys Ser Ala Leu His Trp Ala Ala Ala Val Asn Asn Val Asp
    2030                2035                2040

Ala Ala Val Val Leu Leu Lys Asn Gly Ala Asn Lys Asp Met Gln
    2045                2050                2055

Asn Asn Arg Glu Glu Thr Pro Leu Phe Leu Ala Ala Arg Glu Gly
    2060                2065                2070

Ser Tyr Glu Thr Ala Lys Val Leu Leu Asp His Phe Ala Asn Arg
    2075                2080                2085
```

```
Asp Ile Thr Asp His Met Asp Arg Leu Pro Arg Asp Ile Ala Gln
    2090                2095                2100

Glu Arg Met His His Asp Ile Val Arg Leu Leu Asp Glu Tyr Asn
    2105                2110                2115

Leu Val Arg Ser Pro Gln Leu His Gly Ala Pro Leu Gly Gly Thr
    2120                2125                2130

Pro Thr Leu Ser Pro Pro Leu Cys Ser Pro Asn Gly Tyr Leu Gly
    2135                2140                2145

Ser Leu Lys Pro Gly Val Gln Gly Lys Lys Val Arg Lys Pro Ser
    2150                2155                2160

Ser Lys Gly Leu Ala Cys Gly Ser Lys Glu Ala Lys Asp Leu Lys
    2165                2170                2175

Ala Arg Arg Lys Lys Ser Gln Asp Gly Lys Gly Cys Leu Leu Asp
    2180                2185                2190

Ser Ser Gly Met Leu Ser Pro Val Asp Ser Leu Glu Ser Pro His
    2195                2200                2205

Gly Tyr Leu Ser Asp Val Ala Ser Pro Pro Leu Leu Pro Ser Pro
    2210                2215                2220

Phe Gln Gln Ser Pro Ser Val Pro Leu Asn His Leu Pro Gly Met
    2225                2230                2235

Pro Asp Thr His Leu Gly Ile Gly His Leu Asn Val Ala Ala Lys
    2240                2245                2250

Pro Glu Met Ala Ala Leu Gly Gly Gly Gly Arg Leu Ala Phe Glu
    2255                2260                2265

Thr Gly Pro Pro Arg Leu Ser His Leu Pro Val Ala Ser Gly Thr
    2270                2275                2280

Ser Thr Val Leu Gly Ser Ser Gly Gly Ala Leu Asn Phe Thr
    2285                2290                2295

Val Gly Gly Ser Thr Ser Leu Asn Gly Gln Cys Glu Trp Leu Ser
    2300                2305                2310

Arg Leu Gln Ser Gly Met Val Pro Asn Gln Tyr Asn Pro Leu Arg
    2315                2320                2325

Gly Ser Val Ala Pro Gly Pro Leu Ser Thr Gln Ala Pro Ser Leu
    2330                2335                2340

Gln His Gly Met Val Gly Pro Leu His Ser Ser Leu Ala Ala Ser
    2345                2350                2355

Ala Leu Ser Gln Met Met Ser Tyr Gln Gly Leu Pro Ser Thr Arg
    2360                2365                2370

Leu Ala Thr Gln Pro His Leu Val Gln Thr Gln Val Gln Pro
    2375                2380                2385

Gln Asn Leu Gln Met Gln Gln Gln Asn Leu Gln Pro Ala Asn Ile
    2390                2395                2400

Gln Gln Gln Gln Ser Leu Gln Pro Pro Pro Pro Pro Gln Pro
    2405                2410                2415

His Leu Gly Val Ser Ser Ala Ala Ser Gly His Leu Gly Arg Ser
    2420                2425                2430

Phe Leu Ser Gly Glu Pro Ser Gln Ala Asp Val Gln Pro Leu Gly
    2435                2440                2445

Pro Ser Ser Leu Ala Val His Thr Ile Leu Pro Gln Glu Ser Pro
    2450                2455                2460

Ala Leu Pro Thr Ser Leu Pro Ser Ser Leu Val Pro Pro Val Thr
    2465                2470                2475

Ala Ala Gln Phe Leu Thr Pro Pro Ser Gln His Ser Tyr Ser Ser
```

```
              2480                2485                2490
Pro Val Asp Asn Thr Pro Ser His Gln Leu Gln Val Pro Glu His
        2495                2500                2505
Pro Phe Leu Thr Pro Ser Pro Glu Ser Pro Asp Gln Trp Ser Ser
        2510                2515                2520
Ser Ser Pro His Ser Asn Val Ser Asp Trp Ser Glu Gly Val Ser
        2525                2530                2535
Ser Pro Pro Thr Ser Met Gln Ser Gln Ile Ala Arg Ile Pro Glu
        2540                2545                2550
Ala Phe Lys
        2555

<210> SEQ ID NO 2
<211> LENGTH: 9
<212> TYPE: PRT
<213> ORGANISM: artificial
<220> FEATURE:
<223> OTHER INFORMATION: peptide sequence for antibody antigen/immunogen

<400> SEQUENCE: 2

Val Leu Leu Ser Arg Lys Arg Arg Arg
1               5

<210> SEQ ID NO 3
<211> LENGTH: 15
<212> TYPE: PRT
<213> ORGANISM: artificial
<220> FEATURE:
<223> OTHER INFORMATION: peptide sequence for avidity tag (AviTag)
<220> FEATURE:
<221> NAME/KEY: MISC_FEATURE
<222> LOCATION: (10)..(10)
<223> OTHER INFORMATION: Lysine at position 10 may by biotinylated

<400> SEQUENCE: 3

Gly Leu Asn Asp Ile Phe Glu Ala Gln Lys Ile Glu Trp His Glu
1               5                   10                  15

<210> SEQ ID NO 4
<211> LENGTH: 829
<212> TYPE: DNA
<213> ORGANISM: artificial
<220> FEATURE:
<223> OTHER INFORMATION: nucleotide sequence of MBP-N1-Sb1 fusion

<400> SEQUENCE: 4
aaagagttcc tcgaaaacta tctgctgact gatgaaggtc tggaagcggt taataaagac        60
aaaccgctgg gtgccgtagc gctgaagtct tacgaggaag agttggcgaa agatccacgt       120
attgccgcca caatggaaaa cgcccagaaa ggtgaaatca tgccgaacat cccgcagatg       180
tccgctttct ggtatgccgt gcgtactgcg gtgatcaacg ccgccagcgg tcgtcagact       240
gtcgatgaag ccctgaaaga cgcgcagact aattcgagct cgaacaacaa caacaataac       300
aataacaaca acctcgggag cagcggactg gttccacgag atcccatat ggctagcgcg        360 cagctgcact tcatgtacgt ggcggcggcc gcctttgtgc ttctgttctt cgtgggctgc       420
ggggtgctgc tgtcccgcaa gcgccggcgg cagcatggcc agctctggtt ccctgagggc       480
ttcaaagtgt ctgaggccag caagaagaag cggcgggagc ccctcggcga ggactccgtg       540
ggcctcaagc ccctgaagaa cgcttcgac ggtgccctca tggacgacaa ccagaatgag        600
gaagcttgct tgggtggcgg tctgaacgac atcttcgagg ctcagaaaat cgaatggcac       660
```

```
gaataactcg agcaccacca ccaccaccac tgagatccgg ctgctaacaa agcccgaaag    720
gaagctgagt tggctgctgc caccgctgag caataactag cataacccct tggggcctct    780
aaacgggtct tgaggggttt tttgctgaaa ggaggaacta tatccggat               829
```

<210> SEQ ID NO 5
<211> LENGTH: 5901
<212> TYPE: DNA
<213> ORGANISM: artificial
<220> FEATURE:
<223> OTHER INFORMATION: nucleotide sequence of plasmid pIAD16
      containing the N1-Sb1 insert

<400> SEQUENCE: 5

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc    120
ctttctcgcc acgttcgccg gctttccccg tcaagctcta atcgggggc tccctttagg    180 gttccgattt agtgctttac ggcacctcga ccccaaaaaa cttgattagg gtgatggttc    240
acgtagtggg ccatcgccct gatagacggt ttttcgccct tgacgttgg agtccacgtt    300 ctttaatagt ggactcttgt tccaaactgg aacaacactc aaccctatct cggtctattc    360
ttttgattta agggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa agtttatgc atttctttcc    840 agacttgttc aacaggccag ccattacgct cgtcatcaaa atcactcgca tcaaccaaac    900
cgttattcat tcgtgattgc gcctgagcga cgaaatac gcgatcgctg ttaaaaggac    960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440 cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccgggttg gactcaagac gatagttacc ggataaggcg    1800
cagcggtcgg gctgaacggg gggttcgtgc acacagccca gcttggagcg aacgacctac    1860
```

```
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag     2040
cgtcgatttt tgtgatgctc gtcagggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
```

-continued

```
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc aacagtccc    4800 ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggaatcg aagaaggtaa actggtaatc    5100
tggattaacg gcgataaagg ctataacggt ctcgctgaag tcggtaagaa attcgagaaa    5160
gataccggaa ttaaagtcac cgttgagcat ccggataaac tggaagagaa attcccacag    5220
gttgcggcaa ctggcgatgg ccctgacatt atcttctggg cacacgaccg ctttggtggc    5280
tacgctcaat ctggcctgtt ggctgaaatc accccggaca aagcgttcca ggacaagctg    5340
tatccgttta cctgggatgc cgtacgttac aacggcaagc tgattgctta cccgatcgct    5400
gttgaagcgt tatcgctgat ttataacaaa gatctgctgc cgaacccgcc aaaaacctgg    5460
gaagagatcc cggcgctgga taagaactg aaagcgaaag gtaagagcgc gctgatgttc    5520
aacctgcaag aaccgtactt cacctggccg ctgattgctg ctgacggggg ttatgcgttc    5580
aagtatgaaa acggcaagta cgacattaaa gacgtgggcg tggataacgc tggcgcgaaa    5640
gcgggtctga ccttcctggt tgacctgatt aaaaacaaac acatgaatgc agacaccgat    5700
tactccatcg cagaagctgc ctttaataaa ggcgaaacag cgatgaccat caacggcccg    5760
tgggcatggt ccaacatcga caccagcaaa gtgaattatg gtgtaacggt actgccgacc    5820
ttcaagggtc aaccatccaa accgttcgtt ggcgtgctga gcgcaggtat taacgccgcc    5880
agtccgaaca aagagctggc a                                              5901
```

<210> SEQ ID NO 6
<211> LENGTH: 81
<212> TYPE: PRT
<213> ORGANISM: artificial
<220> FEATURE:
<223> OTHER INFORMATION: Notch substrate N1Sb1 (NTM2)

<400> SEQUENCE: 6

```
Pro Ala Gln Leu His Phe Met Tyr Val Ala Ala Ala Phe Val Leu
1               5                   10                  15

Leu Phe Phe Val Gly Cys Gly Val Leu Leu Ser Arg Lys Arg Arg Arg
            20                  25                  30

Gln His Gly Gln Leu Trp Phe Pro Glu Gly Phe Lys Val Ser Glu Ala
        35                  40                  45

Ser Lys Lys Lys Arg Arg Glu Pro Leu Gly Glu Asp Ser Val Gly Leu
    50                  55                  60
```

Lys Pro Leu Lys Asn Ala Ser Asp Gly Ala Leu Met Asp Asp Asn Gln
65                  70                  75                  80

Asn

<210> SEQ ID NO 7
<211> LENGTH: 39
<212> TYPE: PRT
<213> ORGANISM: artificial
<220> FEATURE:
<223> OTHER INFORMATION: Notch substrate N1Sb2 (NTM1)

<400> SEQUENCE: 7

Pro Ala Gln Leu His Phe Met Tyr Val Ala Ala Ala Phe Val Leu
1               5                   10                  15

Leu Phe Phe Val Gly Cys Gly Val Leu Leu Ser Arg Lys Arg Arg Arg
                20                  25                  30

Gln His Gly Gln Leu Trp Phe
            35

<210> SEQ ID NO 8
<211> LENGTH: 10
<212> TYPE: PRT
<213> ORGANISM: artificial
<220> FEATURE:
<223> OTHER INFORMATION: neopeptide N-terminal sequence generated by
      gamma-secretase cleavage of human Notch1 at the S3 site

<400> SEQUENCE: 8

Val Leu Leu Ser Arg Lys Arg Arg Arg Cys
1               5                   10

<210> SEQ ID NO 9
<211> LENGTH: 93
<212> TYPE: PRT
<213> ORGANISM: artificial
<220> FEATURE:
<223> OTHER INFORMATION: Notch substrate N1Sb3

<400> SEQUENCE: 9

Glu Ala Val Gln Ser Glu Thr Val Glu Pro Pro Pro Pro Ala Gln Leu
1               5                   10                  15

His Phe Met Tyr Val Ala Ala Ala Ala Phe Val Leu Leu Phe Phe Val
                20                  25                  30

Gly Cys Gly Val Leu Leu Ser Arg Lys Arg Arg Arg Gln His Gly Gln
            35                  40                  45

Leu Trp Phe Pro Glu Gly Phe Lys Val Ser Glu Ala Ser Lys Lys Lys
        50                  55                  60

Arg Arg Glu Pro Leu Gly Glu Asp Ser Val Gly Leu Lys Pro Leu Lys
65                  70                  75                  80

Asn Ala Ser Asp Gly Ala Leu Met Asp Asp Asn Gln Asn
                85                  90

<210> SEQ ID NO 10
<211> LENGTH: 105
<212> TYPE: PRT
<213> ORGANISM: artificial
<220> FEATURE:
<223> OTHER INFORMATION: Notch substrate N1Sb4

<400> SEQUENCE: 10

Ala Ser Leu Gly Ser Leu Asn Ile Pro Tyr Lys Ile Glu Ala Val Gln
1               5                   10                  15

Ser Glu Thr Val Glu Pro Pro Pro Ala Gln Leu His Phe Met Tyr
            20                  25                  30

Val Ala Ala Ala Ala Phe Val Leu Leu Phe Phe Val Gly Cys Gly Val
                35                  40                  45

Leu Leu Ser Arg Lys Arg Arg Gln His Gly Gln Leu Trp Phe Pro
 50                  55                  60

Glu Gly Phe Lys Val Ser Glu Ala Ser Lys Lys Arg Arg Glu Pro
65                  70                  75                  80

Leu Gly Glu Asp Ser Val Gly Leu Lys Pro Leu Lys Asn Ala Ser Asp
                85                  90                  95

Gly Ala Leu Met Asp Asp Asn Gln Asn
            100                 105

<210> SEQ ID NO 11
<211> LENGTH: 148
<212> TYPE: PRT
<213> ORGANISM: artificial
<220> FEATURE:
<223> OTHER INFORMATION: Notch substrate N1Sb5

<400> SEQUENCE: 11

Arg Glu Leu Asp Pro Met Asp Val Arg Gly Ser Ile Val Tyr Leu Glu
1               5                   10                  15

Ile Asp Asn Arg Gln Cys Val Gln Ala Ser Ser Gln Cys Phe Gln Ser
            20                  25                  30

Ala Thr Asp Val Ala Ala Phe Leu Gly Ala Leu Ala Ser Leu Gly Ser
        35                  40                  45

Leu Asn Ile Pro Tyr Lys Ile Glu Ala Val Gln Ser Glu Thr Val Glu
 50                 55                  60

Pro Pro Pro Pro Ala Gln Leu His Phe Met Tyr Val Ala Ala Ala Ala
65                  70                  75                  80

Phe Val Leu Leu Phe Phe Val Gly Cys Gly Val Leu Leu Ser Arg Lys
                85                  90                  95

Arg Arg Arg Gln His Gly Gln Leu Trp Phe Pro Glu Gly Phe Lys Val
            100                 105                 110

Ser Glu Ala Ser Lys Lys Arg Arg Glu Pro Leu Gly Glu Asp Ser
            115                 120                 125

Val Gly Leu Lys Pro Leu Lys Asn Ala Ser Asp Gly Ala Leu Met Asp
    130                 135                 140

Asp Asn Gln Asn
145

<210> SEQ ID NO 12
<211> LENGTH: 117
<212> TYPE: PRT
<213> ORGANISM: artificial
<220> FEATURE:
<223> OTHER INFORMATION: Notch substrate N1Sb6

<400> SEQUENCE: 12

Ser Ala Thr Asp Val Ala Ala Phe Leu Gly Ala Leu Ala Ser Leu Gly
1               5                   10                  15

Ser Leu Asn Ile Pro Tyr Lys Ile Glu Ala Val Gln Ser Glu Thr Val
            20                  25                  30

Glu Pro Pro Pro Pro Ala Gln Leu His Phe Met Tyr Val Ala Ala Ala
        35                  40                  45

Ala Phe Val Leu Leu Phe Phe Val Gly Cys Gly Val Leu Leu Ser Arg
 50                  55                  60

```
Lys Arg Arg Arg Gln His Gly Gln Leu Trp Phe Pro Glu Gly Phe Lys
65                  70                  75                  80

Val Ser Glu Ala Ser Lys Lys Arg Arg Glu Pro Leu Gly Glu Asp
                85                  90                  95

Ser Val Gly Leu Lys Pro Leu Lys Asn Ala Ser Asp Gly Ala Leu Met
                100                 105                 110

Asp Asp Asn Gln Asn
            115

<210> SEQ ID NO 13
<211> LENGTH: 87
<212> TYPE: PRT
<213> ORGANISM: artificial
<220> FEATURE:
<223> OTHER INFORMATION: Notch substrate N1Sb7

<400> SEQUENCE: 13

Thr Val Glu Pro Pro Pro Ala Gln Leu His Phe Met Tyr Val Ala
1               5                   10                  15

Ala Ala Ala Phe Val Leu Leu Phe Phe Val Gly Cys Gly Val Leu Leu
                20                  25                  30

Ser Arg Lys Arg Arg Gln His Gly Gln Leu Trp Phe Pro Glu Gly
            35                  40                  45

Phe Lys Val Ser Glu Ala Ser Lys Lys Arg Arg Glu Pro Leu Gly
    50                  55                  60

Glu Asp Ser Val Gly Leu Lys Pro Leu Lys Asn Ala Ser Asp Gly Ala
65                  70                  75                  80

Leu Met Asp Asp Asn Gln Asn
                85

<210> SEQ ID NO 14
<211> LENGTH: 18
<212> TYPE: PRT
<213> ORGANISM: unknown
<220> FEATURE:
<223> OTHER INFORMATION: peptide sequence of APP containing
      gamma-secretase cleavage sites

<400> SEQUENCE: 14

Met Val Gly Gly Val Val Ile Ala Thr Val Ile Val Ile Thr Leu Val
1               5                   10                  15

Met Leu
```